(12) United States Patent
McClurken

(10) Patent No.: US 7,537,595 B2
(45) Date of Patent: May 26, 2009

(54) FLUID-ASSISTED MEDICAL DEVICES, SYSTEMS AND METHODS

(75) Inventor: Michael E. McClurken, Durham, NH (US)

(73) Assignee: TissueLink Medical, Inc., Dover, NH (US)

( * ) Notice: Subject to any disclaimer, the term of this patent is extended or adjusted under 35 U.S.C. 154(b) by 0 days.

(21) Appl. No.: 11/963,209

(22) Filed: Dec. 21, 2007

(65) Prior Publication Data

US 2008/0097429 A1 Apr. 24, 2008

Related U.S. Application Data

(63) Continuation of application No. 10/494,597, filed as application No. PCT/US02/39701 on Dec. 11, 2002, now Pat. No. 7,311,708.

(60) Provisional application No. 60/340,429, filed on Dec. 12, 2001.

(51) Int. Cl.
*A61B 18/14* (2006.01)
(52) U.S. Cl. ............................................. 606/50
(58) Field of Classification Search .................. 606/48, 606/50
See application file for complete search history.

(56) References Cited

U.S. PATENT DOCUMENTS

| 623,022 | A | 4/1899 | Johnson |
|---|---|---|---|
| 1,735,271 | A | 11/1929 | Groff |
| 1,814,791 | A | 7/1931 | Ende |
| 2,002,594 | A | 5/1935 | Wappler et al. |
| 2,031,682 | A | 2/1936 | Wappler et al. |
| 2,102,270 | A | 12/1937 | Hyams |
| 2,275,167 | A | 3/1942 | Bierman |
| 2,888,928 | A | 6/1959 | Seiger |
| 3,163,166 | A | 12/1964 | Brant et al. |
| 3,682,130 | A | 8/1972 | Jeffers |

(Continued)

FOREIGN PATENT DOCUMENTS

DE 1 007 960 5/1957

(Continued)

OTHER PUBLICATIONS

Email from Elson Silva, PhD to Randall A. Hillson titled "Requesting IDS of US 6,766,817 for patents on fluids on porosity by Unsaturated Hydraulic Flow" and dated Apr. 24, 2008.

*Primary Examiner*—Lee S Cohen
(74) *Attorney, Agent, or Firm*—Merchant & Gould P.C.

(57) ABSTRACT

A medical device is provided which comprises a catheter tube having a distal end and a lumen, and configured to assist in applying tamponage to a bleeding source in a gastrointestinal tract when flexed. A catheter tip having a catheter tip outer surface is assembled with the tube adjacent the distal end of the tube. The catheter tip comprises a probe body comprising an electrically insulative material, at least one electrode pair located on the probe body which comprises a first electrode spaced from a second electrode, and a fluid distribution manifold to direct a fluid from inside the probe body towards the tip outer surface. The manifold comprises a central passage within the probe body and a plurality of lateral passages which extend from the central passage towards the tip outer surface. An extendable injection needle is housed within the central passage to provide treatment to tissue.

20 Claims, 66 Drawing Sheets

U.S. PATENT DOCUMENTS

| | | | |
|---|---|---|---|
| 3,750,650 A | 8/1973 | Ruttgers | |
| 3,901,241 A | 8/1975 | Allen, Jr. | |
| 4,037,590 A | 7/1977 | Dohring et al. | |
| 4,060,088 A | 11/1977 | Morrison, Jr. et al. | |
| 4,116,198 A | 9/1978 | Roos | |
| 4,244,371 A | 1/1981 | Farin | |
| 4,276,874 A | 7/1981 | Wolvek et al. | |
| 4,301,802 A | 11/1981 | Poler | |
| 4,307,720 A | 12/1981 | Weber, Jr. | |
| 4,321,931 A | 3/1982 | Hon | |
| 4,326,529 A | 4/1982 | Doss et al. | |
| 4,342,218 A | 8/1982 | Fox | |
| 4,355,642 A | 10/1982 | Alferness | |
| 4,381,007 A | 4/1983 | Doss | |
| 4,532,924 A * | 8/1985 | Auth et al. | 606/50 |
| 4,548,207 A | 10/1985 | Reimels | |
| 4,567,890 A | 2/1986 | Ohta et al. | |
| 4,602,628 A | 7/1986 | Allen, Jr. | |
| 4,671,274 A | 6/1987 | Sorochenko | |
| 4,674,499 A | 6/1987 | Pao | |
| 4,920,982 A | 5/1990 | Goldstein | |
| 4,931,047 A | 6/1990 | Broadwin et al. | |
| 4,932,952 A | 6/1990 | Wojciechowicz, Jr. | |
| 4,943,290 A | 7/1990 | Rexroth et al. | |
| 4,950,232 A | 8/1990 | Ruzicka et al. | |
| 4,976,711 A | 12/1990 | Parins et al. | |
| 4,985,030 A | 1/1991 | Melzer et al. | |
| 4,998,933 A | 3/1991 | Eggers et al. | |
| 5,009,656 A | 4/1991 | Reimels | |
| 5,013,312 A | 5/1991 | Parins et al. | |
| 5,035,696 A | 7/1991 | Rydell | |
| 5,071,419 A | 12/1991 | Rydell et al. | |
| 5,080,660 A | 1/1992 | Buelna | |
| 5,122,138 A | 6/1992 | Manwaring | |
| 5,125,928 A | 6/1992 | Parins et al. | |
| 5,147,357 A | 9/1992 | Rose et al. | |
| 5,151,102 A | 9/1992 | Kamiyama et al. | |
| 5,156,613 A | 10/1992 | Sawyer | |
| 5,167,659 A | 12/1992 | Ohtomo et al. | |
| 5,171,311 A | 12/1992 | Rydell et al. | |
| 5,190,541 A | 3/1993 | Abele et al. | |
| 5,195,959 A | 3/1993 | Smith | |
| 5,197,963 A | 3/1993 | Parins | |
| 5,197,964 A | 3/1993 | Parins | |
| 5,217,460 A | 6/1993 | Knoepfler | |
| 5,234,428 A | 8/1993 | Kaufman | |
| 5,242,441 A | 9/1993 | Avitall | |
| 5,242,442 A | 9/1993 | Hirschfeld | |
| 5,269,780 A | 12/1993 | Roos | |
| 5,269,781 A | 12/1993 | Hewell, III | |
| 5,277,696 A | 1/1994 | Hagen | |
| 5,281,215 A | 1/1994 | Milder | |
| 5,281,216 A | 1/1994 | Klicek | |
| 5,282,799 A | 2/1994 | Rydell | |
| 5,290,286 A | 3/1994 | Parins | |
| 5,300,087 A | 4/1994 | Knoepfler | |
| 5,313,943 A | 5/1994 | Houser et al. | |
| 5,318,589 A | 6/1994 | Lichtman | |
| 5,322,503 A | 6/1994 | Desai | |
| 5,330,521 A | 7/1994 | Cohen | |
| 5,334,193 A | 8/1994 | Nardella | |
| 5,342,357 A | 8/1994 | Nardella | |
| 5,342,359 A | 8/1994 | Rydell | |
| 5,348,554 A | 9/1994 | Imran et al. | |
| 5,364,394 A | 11/1994 | Mehl | |
| 5,383,874 A | 1/1995 | Jackson et al. | |
| 5,383,876 A | 1/1995 | Nardella | |
| 5,395,312 A | 3/1995 | Desai | |
| 5,395,363 A | 3/1995 | Billings et al. | |
| 5,401,272 A | 3/1995 | Perkins | |
| 5,403,311 A | 4/1995 | Abele et al. | |
| 5,403,312 A | 4/1995 | Yates et al. | |
| 5,405,344 A | 4/1995 | Williamson et al. | |
| 5,405,376 A | 4/1995 | Mulier et al. | |
| 5,417,672 A | 5/1995 | Nita et al. | |
| 5,417,709 A | 5/1995 | Slater | |
| 5,431,168 A * | 7/1995 | Webster, Jr. | 600/435 |
| 5,431,649 A | 7/1995 | Mulier et al. | |
| 5,433,708 A | 7/1995 | Nichols et al. | |
| 5,437,662 A | 8/1995 | Nardella | |
| 5,437,664 A | 8/1995 | Cohen et al. | |
| 5,441,498 A | 8/1995 | Perkins | |
| 5,441,503 A | 8/1995 | Considine et al. | |
| 5,445,638 A | 8/1995 | Rydell et al. | |
| 5,456,682 A | 10/1995 | Edwards et al. | |
| 5,456,684 A | 10/1995 | Schmidt et al. | |
| 5,458,596 A | 10/1995 | Lax et al. | |
| 5,458,597 A | 10/1995 | Edwards et al. | |
| 5,458,598 A | 10/1995 | Feinberg et al. | |
| 5,460,629 A | 10/1995 | Shlain et al. | |
| 5,462,521 A | 10/1995 | Brucker et al. | |
| 5,472,441 A | 12/1995 | Edwards et al. | |
| 5,472,443 A | 12/1995 | Cordis et al. | |
| 5,487,385 A | 1/1996 | Avitall | |
| 5,490,819 A | 2/1996 | Nicholas et al. | |
| 5,500,012 A | 3/1996 | Brucker et al. | |
| 5,514,130 A | 5/1996 | Baker | |
| 5,522,815 A * | 6/1996 | Durgin et al. | 606/50 |
| 5,536,267 A | 7/1996 | Edwards et al. | |
| 5,540,562 A | 7/1996 | Giter | |
| 5,542,928 A | 8/1996 | Evans et al. | |
| 5,558,671 A | 9/1996 | Yates | |
| 5,562,503 A | 10/1996 | Ellman et al. | |
| 5,562,703 A | 10/1996 | Desai | |
| 5,564,440 A | 10/1996 | Swartz et al. | |
| 5,569,242 A | 10/1996 | Lax et al. | |
| 5,569,243 A | 10/1996 | Kortenbach et al. | |
| 5,573,424 A | 11/1996 | Poppe | |
| 5,573,533 A | 11/1996 | Strul | |
| 5,575,810 A | 11/1996 | Swanson et al. | |
| 5,584,872 A | 12/1996 | LaFontaine et al. | |
| 5,599,346 A | 2/1997 | Edwards et al. | |
| 5,599,350 A | 2/1997 | Schulze et al. | |
| 5,605,539 A | 2/1997 | Buelna et al. | |
| 5,609,151 A | 3/1997 | Mulier et al. | |
| 5,633,578 A | 5/1997 | Eggers et al. | |
| 5,637,110 A | 6/1997 | Pennybacker et al. | |
| 5,640,955 A | 6/1997 | Ockuly et al. | |
| 5,643,197 A | 7/1997 | Brucker et al. | |
| 5,647,869 A | 7/1997 | Goble et al. | |
| 5,647,871 A | 7/1997 | Levine et al. | |
| 5,653,692 A | 8/1997 | Masterson et al. | |
| 5,660,836 A | 8/1997 | Knowlton | |
| 5,676,662 A | 10/1997 | Fleischhacker et al. | |
| 5,676,693 A | 10/1997 | LaFontaine | |
| 5,681,282 A | 10/1997 | Eggers et al. | |
| 5,683,366 A | 11/1997 | Eggers et al. | |
| 5,683,384 A | 11/1997 | Gough et al. | |
| 5,687,723 A | 11/1997 | Avitall | |
| 5,688,270 A | 11/1997 | Yates et al. | |
| 5,693,045 A | 12/1997 | Eggers | |
| 5,697,281 A | 12/1997 | Eggers et al. | |
| 5,697,536 A | 12/1997 | Eggers et al. | |
| 5,697,882 A | 12/1997 | Eggers et al. | |
| 5,697,909 A | 12/1997 | Eggers et al. | |
| 5,697,927 A | 12/1997 | Imran et al. | |
| 5,702,386 A | 12/1997 | Stern et al. | |
| 5,709,680 A | 1/1998 | Yates et al. | |
| 5,713,896 A | 2/1998 | Nardella | |
| 5,718,241 A | 2/1998 | Ben-Haim et al. | |
| 5,718,701 A | 2/1998 | Shai et al. | |
| 5,718,703 A | 2/1998 | Chin | |
| 5,722,400 A | 3/1998 | Ockuly et al. | |
| 5,725,524 A | 3/1998 | Mulier et al. | |

| Patent | Date | Inventor | | Patent | Date | Inventor |
|---|---|---|---|---|---|---|
| 5,730,127 A | 3/1998 | Avitall | | 6,004,316 A | 12/1999 | Laufer |
| 5,735,846 A | 4/1998 | Panescu et al. | | 6,004,319 A | 12/1999 | Goble et al. |
| 5,743,903 A | 4/1998 | Stern et al. | | 6,007,570 A | 12/1999 | Sharkey et al. |
| 5,746,739 A | 5/1998 | Sutter | | 6,010,500 A | 1/2000 | Sherman et al. |
| 5,749,869 A | 5/1998 | Lindenmeier et al. | | 6,015,391 A | 1/2000 | Rishton et al. |
| 5,755,717 A | 5/1998 | Yates et al. | | 6,015,407 A | 1/2000 | Rieb et al. |
| 5,755,753 A | 5/1998 | Knowlton | | 6,016,809 A | 1/2000 | Mulier et al. |
| 5,766,153 A | 6/1998 | Eggers et al. | | 6,017,338 A * | 1/2000 | Brucker et al. ............... 606/41 |
| 5,766,167 A | 6/1998 | Eggers et al. | | 6,018,676 A | 1/2000 | Davis et al. |
| 5,785,705 A | 7/1998 | Baker | | 6,019,757 A | 2/2000 | Scheldrup |
| 5,785,706 A | 7/1998 | Bednarek | | 6,024,733 A | 2/2000 | Eggers et al. |
| 5,792,140 A | 8/1998 | Tu et al. | | 6,027,501 A | 2/2000 | Goble et al. |
| 5,797,905 A | 8/1998 | Fleischman et al. | | 6,030,379 A | 2/2000 | Panescu et al. |
| 5,797,960 A | 8/1998 | Stevens et al. | | 6,032,077 A | 2/2000 | Pomeranz |
| 5,800,413 A | 9/1998 | Swartz et al. | | 6,032,674 A | 3/2000 | Eggers et al. |
| 5,800,482 A | 9/1998 | Pomeranz | | 6,033,398 A | 3/2000 | Farley et al. |
| 5,807,393 A | 9/1998 | Williamson et al. | | 6,035,238 A | 3/2000 | Ingle et al. |
| 5,807,395 A | 9/1998 | Mulier et al. | | 6,036,687 A | 3/2000 | Laufer et al. |
| 5,810,764 A | 9/1998 | Eggers et al. | | 6,045,532 A | 4/2000 | Eggers et al. |
| 5,810,805 A | 9/1998 | Sutcu et al. | | 6,047,700 A | 4/2000 | Eggers et al. |
| 5,810,811 A | 9/1998 | Yates et al. | | 6,048,333 A | 4/2000 | Lennox et al. |
| 5,817,093 A | 10/1998 | Williamson et al. | | 6,053,172 A | 4/2000 | Hovda et al. |
| 5,823,956 A | 10/1998 | Roth et al. | | 6,053,912 A | 4/2000 | Panescu et al. |
| 5,827,271 A | 10/1998 | Buysse et al. | | 6,056,744 A | 5/2000 | Edwards |
| 5,827,281 A | 10/1998 | Levin | | 6,056,745 A | 5/2000 | Panescu et al. |
| 5,833,703 A | 11/1998 | Manushakian | | 6,056,747 A | 5/2000 | Saadat et al. |
| 5,843,019 A | 12/1998 | Eggers et al. | | 6,059,781 A | 5/2000 | Yamanashi et al. |
| 5,843,021 A | 12/1998 | Edwards et al. | | 6,063,079 A | 5/2000 | Hovda et al. |
| 5,843,078 A | 12/1998 | Sharkey | | 6,063,081 A | 5/2000 | Mulier et al. |
| 5,843,152 A | 12/1998 | Tu et al. | | 6,066,134 A | 5/2000 | Eggers et al. |
| 5,855,614 A | 1/1999 | Stevens et al. | | 6,066,139 A | 5/2000 | Ryan et al. |
| 5,860,951 A | 1/1999 | Eggers et al. | | 6,068,627 A | 5/2000 | Orszulak et al. |
| 5,860,974 A | 1/1999 | Abele | | 6,068,653 A | 5/2000 | LaFontaine |
| 5,861,002 A | 1/1999 | Desai | | 6,071,280 A | 6/2000 | Edwards et al. |
| 5,861,021 A | 1/1999 | Thome et al. | | 6,073,051 A | 6/2000 | Sharkey et al. |
| 5,868,739 A | 2/1999 | Lindenmeier et al. | | 6,074,389 A | 6/2000 | Levine et al. |
| 5,871,469 A | 2/1999 | Eggers et al. | | 6,080,151 A | 6/2000 | Swartz et al. |
| 5,871,524 A | 2/1999 | Knowlton | | 6,081,749 A | 6/2000 | Ingle et al. |
| 5,873,855 A | 2/1999 | Eggers et al. | | 6,083,237 A | 7/2000 | Huitema et al. |
| 5,876,398 A | 3/1999 | Mulier et al. | | 6,086,585 A | 7/2000 | Hovda et al. |
| 5,888,198 A | 3/1999 | Eggers et al. | | 6,086,586 A | 7/2000 | Hooven |
| 5,891,095 A | 4/1999 | Eggers et al. | | 6,091,995 A | 7/2000 | Ingle et al. |
| 5,891,141 A | 4/1999 | Rydell | | 6,093,186 A | 7/2000 | Goble |
| 5,891,142 A | 4/1999 | Eggers et al. | | 6,095,149 A | 8/2000 | Sharkey et al. |
| 5,893,848 A | 4/1999 | Negus et al. | | 6,096,037 A | 8/2000 | Mulier et al. |
| 5,895,355 A | 4/1999 | Schaer | | 6,099,514 A | 8/2000 | Sharkey et al. |
| 5,895,417 A | 4/1999 | Pomeranz et al. | | 6,102,046 A | 8/2000 | Weinstein et al. |
| 5,897,553 A | 4/1999 | Mulier et al. | | 6,105,581 A | 8/2000 | Eggers et al. |
| 5,902,272 A | 5/1999 | Eggers et al. | | 6,109,268 A | 8/2000 | Thapliyal et al. |
| 5,902,328 A | 5/1999 | LaFontaine et al. | | 6,113,596 A | 9/2000 | Hooven et al. |
| 5,904,711 A | 5/1999 | Flom et al. | | 6,113,597 A | 9/2000 | Eggers et al. |
| 5,906,613 A | 5/1999 | Mulier et al. | | 6,117,109 A | 9/2000 | Eggers et al. |
| 5,913,854 A | 6/1999 | Maguire et al. | | 6,122,549 A | 9/2000 | Sharkey et al. |
| 5,913,856 A | 6/1999 | Chia et al. | | H1904 H | 10/2000 | Yates et al. |
| 5,919,191 A | 7/1999 | Lennox et al. | | 6,126,682 A | 10/2000 | Sharkey et al. |
| 5,919,219 A | 7/1999 | Knowlton | | 6,135,999 A | 10/2000 | Fanton et al. |
| 5,921,982 A * | 7/1999 | Lesh et al. ............... 606/41 | | 6,141,576 A | 10/2000 | Littmann et al. |
| 5,921,983 A | 7/1999 | Shannon, Jr. | | 6,142,992 A | 11/2000 | Cheng et al. |
| 5,925,045 A | 7/1999 | Reimels et al. | | 6,149,620 A | 11/2000 | Baker et al. |
| 5,935,123 A | 8/1999 | Edwards et al. | | 6,159,194 A | 12/2000 | Eggers et al. |
| 5,948,011 A | 9/1999 | Knowlton | | 6,159,208 A | 12/2000 | Hovda et al. |
| 5,951,549 A | 9/1999 | Richardson et al. | | 6,165,169 A | 12/2000 | Panescu et al. |
| 5,954,716 A | 9/1999 | Sharkey et al. | | 6,165,175 A | 12/2000 | Wampler et al. |
| 5,957,919 A | 9/1999 | Laufer | | 6,168,594 B1 | 1/2001 | LaFontaine et al. |
| 5,964,755 A | 10/1999 | Edwards | | 6,171,275 B1 * | 1/2001 | Webster, Jr. ............... 604/20 |
| 5,971,983 A | 10/1999 | Lesh | | 6,174,308 B1 | 1/2001 | Goble et al. |
| 5,976,128 A | 11/1999 | Schilling et al. | | 6,174,309 B1 | 1/2001 | Wrubleski et al. |
| 5,980,504 A | 11/1999 | Sharkey et al. | | 6,176,857 B1 | 1/2001 | Ashley |
| 5,980,516 A | 11/1999 | Mulier et al. | | 6,179,824 B1 | 1/2001 | Eggers et al. |
| 5,989,248 A | 11/1999 | Tu et al. | | 6,179,836 B1 | 1/2001 | Eggers et al. |
| 5,992,418 A | 11/1999 | de la Rama et al. | | 6,183,469 B1 | 2/2001 | Thapliyal et al. |
| 5,993,412 A | 11/1999 | Deily et al. | | 6,190,381 B1 | 2/2001 | Olsen et al. |
| 6,003,517 A | 12/1999 | Sheffield et al. | | 6,190,384 B1 | 2/2001 | Ouchi |

| Patent | Kind | Date | Inventor |
|---|---|---|---|
| 6,193,715 | B1 | 2/2001 | Wrubleski et al. |
| 6,193,716 | B1 | 2/2001 | Shannon, Jr. |
| 6,203,542 | B1 | 3/2001 | Ellsberry et al. |
| 6,210,402 | B1 | 4/2001 | Olsen et al. |
| 6,210,410 | B1 | 4/2001 | Farin et al. |
| 6,210,411 | B1 | 4/2001 | Hofmann et al. |
| 6,212,426 | B1 | 4/2001 | Swanson |
| 6,216,704 | B1 | 4/2001 | Ingle et al. |
| 6,217,576 | B1 | 4/2001 | Tu et al. |
| 6,221,039 | B1 | 4/2001 | Durgin et al. |
| 6,221,069 | B1 | 4/2001 | Daikuzono |
| 6,224,592 | B1 | 5/2001 | Eggers et al. |
| 6,224,593 | B1 | 5/2001 | Ryan et al. |
| 6,226,554 | B1 | 5/2001 | Tu et al. |
| 6,228,078 | B1 | 5/2001 | Eggers et al. |
| 6,228,082 | B1 | 5/2001 | Baker et al. |
| 6,231,591 | B1 | 5/2001 | Desai |
| 6,235,020 | B1 | 5/2001 | Cheng et al. |
| 6,236,891 | B1 | 5/2001 | Ingle et al. |
| 6,238,387 | B1 | 5/2001 | Miller, III |
| 6,238,391 | B1 | 5/2001 | Olsen et al. |
| 6,238,393 | B1 | 5/2001 | Mulier et al. |
| 6,241,753 | B1 | 6/2001 | Knowlton |
| 6,241,754 | B1 | 6/2001 | Swanson et al. |
| 6,251,110 | B1 | 6/2001 | Wampler |
| 6,254,600 | B1 | 7/2001 | Willink et al. |
| 6,258,086 | B1 | 7/2001 | Ashley et al. |
| 6,258,087 | B1 | 7/2001 | Edwards et al. |
| 6,261,311 | B1 | 7/2001 | Sharkey et al. |
| 6,264,650 | B1 | 7/2001 | Hovda et al. |
| 6,264,651 | B1 | 7/2001 | Underwood et al. |
| 6,264,652 | B1 | 7/2001 | Eggers et al. |
| 6,264,654 | B1 | 7/2001 | Swartz et al. |
| 6,266,551 | B1 | 7/2001 | Osadchy et al. |
| 6,277,112 | B1 | 8/2001 | Underwood et al. |
| 6,280,440 | B1 | 8/2001 | Gocho |
| 6,283,961 | B1 | 9/2001 | Underwood et al. |
| 6,283,988 | B1 | 9/2001 | Laufer et al. |
| 6,283,989 | B1 | 9/2001 | Laufer et al. |
| 6,290,715 | B1 | 9/2001 | Sharkey et al. |
| 6,293,942 | B1 | 9/2001 | Goble et al. |
| 6,293,945 | B1 | 9/2001 | Parins et al. |
| 6,296,636 | B1 | 10/2001 | Cheng et al. |
| 6,296,638 | B1 | 10/2001 | Davison et al. |
| 6,296,640 | B1 | 10/2001 | Wampler et al. |
| 6,299,633 | B1 | 10/2001 | Laufer |
| 6,302,903 | B1 | 10/2001 | Mulier et al. |
| 6,306,134 | B1 | 10/2001 | Goble et al. |
| 6,309,387 | B1 | 10/2001 | Eggers et al. |
| 6,311,090 | B1 | 10/2001 | Knowlton |
| 6,312,408 | B1 | 11/2001 | Eggers et al. |
| 6,312,430 | B1 | 11/2001 | Wilson et al. |
| 6,315,777 | B1 | 11/2001 | Comben |
| 6,322,549 | B1 | 11/2001 | Eggers et al. |
| 6,322,559 | B1 | 11/2001 | Daulton et al. |
| 6,327,505 | B1 | 12/2001 | Medhkour et al. |
| 6,328,735 | B1 | 12/2001 | Curley et al. |
| 6,328,736 | B1 | 12/2001 | Mulier et al. |
| 6,336,926 | B1 | 1/2002 | Goble |
| 6,350,262 | B1 | 2/2002 | Ashley |
| 6,350,276 | B1 | 2/2002 | Knowlton |
| 6,352,533 | B1 | 3/2002 | Ellman et al. |
| 6,355,032 | B1 | 3/2002 | Hovda et al. |
| 6,358,245 | B1 | 3/2002 | Edwards et al. |
| 6,358,248 | B1 | 3/2002 | Mulier et al. |
| 6,363,937 | B1 | 4/2002 | Hovda et al. |
| 6,371,956 | B1 | 4/2002 | Wilson et al. |
| 6,379,350 | B1 | 4/2002 | Sharkey et al. |
| 6,379,351 | B1 | 4/2002 | Thapliyal et al. |
| 6,391,025 | B1 | 5/2002 | Weinstein et al. |
| 6,391,028 | B1 | 5/2002 | Fanton et al. |
| 6,402,742 | B1 | 6/2002 | Blewett et al. |
| 6,409,722 | B1 | 6/2002 | Hoey et al. |
| 6,409,723 | B1 | 6/2002 | Edwards |
| H2037 | H | 7/2002 | Yates et al. |
| 6,416,507 | B1 | 7/2002 | Eggers et al. |
| 6,416,508 | B1 | 7/2002 | Eggers et al. |
| 6,416,509 | B1 | 7/2002 | Goble et al. |
| 6,425,877 | B1 | 7/2002 | Edwards |
| 6,432,103 | B1 | 8/2002 | Ellsberry et al. |
| 6,440,130 | B1 | 8/2002 | Mulier et al. |
| 6,443,952 | B1 | 9/2002 | Mulier et al. |
| 6,451,017 | B1 | 9/2002 | Moutafis et al. |
| 6,458,123 | B1 | 10/2002 | Brucker et al. |
| 6,458,130 | B1 | 10/2002 | Frazier et al. |
| 6,461,350 | B1 | 10/2002 | Underwood et al. |
| 6,461,354 | B1 | 10/2002 | Olsen et al. |
| 6,461,357 | B1 | 10/2002 | Sharkey et al. |
| 6,464,695 | B2 | 10/2002 | Hovda et al. |
| 6,468,270 | B1 | 10/2002 | Hovda et al. |
| 6,468,274 | B1 | 10/2002 | Alleyne et al. |
| 6,468,275 | B1 | 10/2002 | Wampler et al. |
| 6,471,698 | B1 | 10/2002 | Edwards et al. |
| 6,475,216 | B2 | 11/2002 | Mulier et al. |
| 6,478,793 | B1 | 11/2002 | Cosman et al. |
| 6,482,202 | B1 | 11/2002 | Goble et al. |
| 6,485,490 | B2 | 11/2002 | Wampler et al. |
| 6,488,680 | B1 | 12/2002 | Francischelli et al. |
| 6,493,589 | B1 | 12/2002 | Medhkour et al. |
| 6,494,902 | B2 | 12/2002 | Hoey et al. |
| 6,497,704 | B2 | 12/2002 | Ein-Gal |
| 6,497,705 | B2 | 12/2002 | Comben |
| 6,506,189 | B1 | 1/2003 | Rittman, III et al. |
| 6,508,815 | B1 | 1/2003 | Strul et al. |
| 6,517,536 | B2 | 2/2003 | Hooven et al. |
| 6,526,320 | B2 | 2/2003 | Mitchell |
| 6,537,248 | B2 | 3/2003 | Mulier et al. |
| 6,537,272 | B2 | 3/2003 | Christopherson et al. |
| 6,539,265 | B2 | 3/2003 | Medhkour et al. |
| 6,558,379 | B1 | 5/2003 | Batchelor et al. |
| 6,558,385 | B1 | 5/2003 | McClurken et al. |
| 6,575,969 | B1 | 6/2003 | Rittman, III et al. |
| 6,577,902 | B1 | 6/2003 | Laufer et al. |
| 6,579,288 | B1 | 6/2003 | Swanson et al. |
| 6,585,732 | B2 | 7/2003 | Mulier et al. |
| 6,602,248 | B1 | 8/2003 | Sharps et al. |
| 6,603,988 | B2 | 8/2003 | Dowlatshahi |
| 6,610,060 | B2 | 8/2003 | Mulier et al. |
| 6,613,048 | B2 | 9/2003 | Mulier et al. |
| 6,623,515 | B2 | 9/2003 | Mulier et al. |
| 6,626,899 | B2 | 9/2003 | Houser et al. |
| 6,645,202 | B1 | 11/2003 | Pless et al. |
| 6,666,862 | B2 | 12/2003 | Jain et al. |
| 6,669,692 | B1 | 12/2003 | Nelson et al. |
| 6,676,660 | B2 | 1/2004 | Wampler |
| 6,679,882 | B1 | 1/2004 | Kornerup |
| 6,682,501 | B1 | 1/2004 | Nelson et al. |
| 6,682,527 | B2 | 1/2004 | Strul |
| 6,682,528 | B2 | 1/2004 | Frazier et al. |
| 6,685,700 | B2 | 2/2004 | Behl et al. |
| 6,685,701 | B2 | 2/2004 | Orszulak et al. |
| 6,685,704 | B2 | 2/2004 | Greep |
| 6,689,129 | B2 | 2/2004 | Baker |
| 6,689,131 | B2 | 2/2004 | McClurken |
| 6,692,489 | B1 | 2/2004 | Heim et al. |
| 6,694,984 | B2 | 2/2004 | Habib |
| 6,695,837 | B2 | 2/2004 | Howell |
| 6,695,840 | B2 | 2/2004 | Schulze |
| 6,699,240 | B2 | 3/2004 | Francischelli |
| 6,699,242 | B2 | 3/2004 | Heggeness |
| 6,699,244 | B2 | 3/2004 | Carranza et al. |
| 6,699,268 | B2 | 3/2004 | Kordis et al. |
| 6,702,810 | B2 | 3/2004 | McClurken et al. |
| 6,702,812 | B2 | 3/2004 | Cosmescu |
| 6,706,039 | B2 | 3/2004 | Mulier et al. |
| 6,712,074 | B2 | 3/2004 | Edwards et al. |

| | | | | | | |
|---|---|---|---|---|---|---|
| 6,712,811 B2 | 3/2004 | Underwood et al. | | 6,911,019 B2 | 6/2005 | Mulier et al. |
| 6,712,813 B2 | 3/2004 | Ellman et al. | | 6,915,806 B2 | 7/2005 | Pacek et al. |
| 6,712,816 B2 | 3/2004 | Hung et al. | | 6,918,404 B2 | 7/2005 | Dias da Silva |
| 6,716,211 B2 | 4/2004 | Mulier et al. | | 6,921,398 B2 | 7/2005 | Carmel et al. |
| 6,719,754 B2 | 4/2004 | Underwood et al. | | 6,921,399 B2 | 7/2005 | Carmel et al. |
| 6,723,094 B1 | 4/2004 | Desinger | | 6,923,803 B2 | 8/2005 | Goble |
| 6,726,683 B1 | 4/2004 | Shaw | | 6,923,805 B1 | 8/2005 | LaFontaine et al. |
| 6,726,684 B1 | 4/2004 | Woloszko et al. | | 6,926,706 B1 | 8/2005 | Sealfon |
| 6,726,686 B2 | 4/2004 | Buysse et al. | | 6,926,716 B2 | 8/2005 | Baker et al. |
| 6,730,081 B1 | 5/2004 | Desai | | 6,926,717 B1 | 8/2005 | Garito et al. |
| 6,733,496 B2 | 5/2004 | Sharkey et al. | | 6,929,640 B1 | 8/2005 | Underwood et al. |
| 6,733,498 B2 | 5/2004 | Paton et al. | | 6,929,641 B2 | 8/2005 | Goble et al. |
| 6,733,501 B2 | 5/2004 | Levine | | 6,929,642 B2 | 8/2005 | Xiao et al. |
| 6,736,810 B2 | 5/2004 | Hoey et al. | | 6,929,644 B2 | 8/2005 | Truckai et al. |
| 6,740,058 B2 | 5/2004 | Lal et al. | | 6,929,645 B2 | 8/2005 | Battles et al. |
| 6,740,079 B1 | 5/2004 | Eggers et al. | | 6,932,810 B2 | 8/2005 | Ryan |
| 6,740,082 B2 | 5/2004 | Shadduck | | 6,932,815 B2 | 8/2005 | Sutter |
| 6,740,084 B2 | 5/2004 | Ryan | | 6,942,661 B2 | 9/2005 | Swanson |
| 6,740,102 B2 | 5/2004 | Hess et al. | | 6,949,096 B2 | 9/2005 | Davison et al. |
| 6,743,197 B1 | 6/2004 | Edwards | | 6,949,098 B2 | 9/2005 | Mulier et al. |
| 6,743,229 B2 | 6/2004 | Buysse et al. | | 6,951,559 B1 | 10/2005 | Greep |
| 6,743,230 B2 | 6/2004 | Lutze et al. | | 6,953,461 B2 | 10/2005 | McClurken et al. |
| 6,746,447 B2 | 6/2004 | Davison et al. | | 6,960,204 B2 | 11/2005 | Eggers et al. |
| 6,755,825 B2 | 6/2004 | Shoenman et al. | | 6,960,207 B2 | 11/2005 | Vanney et al. |
| 6,755,827 B2 | 6/2004 | Mulier et al. | | 6,960,210 B2 | 11/2005 | Lands et al. |
| 6,757,565 B2 | 6/2004 | Sharkey et al. | | 6,962,589 B2 | 11/2005 | Mulier et al. |
| 6,758,846 B2 | 7/2004 | Goble et al. | | 6,964,274 B1 | 11/2005 | Ryan et al. |
| 6,761,718 B2 | 7/2004 | Madsen | | 6,964,661 B2 | 11/2005 | Rioux et al. |
| 6,764,487 B2 | 7/2004 | Mulier et al. | | 6,966,907 B2 | 11/2005 | Goble |
| 6,766,817 B2 | 7/2004 | da Silva | | 6,966,909 B2 | 11/2005 | Marshall et al. |
| 6,770,070 B1 | 8/2004 | Balbierz | | 6,971,394 B2 | 12/2005 | Sliwa, Jr. et al. |
| 6,770,071 B2 | 8/2004 | Woloszko et al. | | 6,974,452 B1 | 12/2005 | Gille et al. |
| 6,770,072 B1 | 8/2004 | Truckai et al. | | 6,974,453 B2 | 12/2005 | Woloszko et al. |
| 6,772,012 B2 | 8/2004 | Ricart et al. | | 6,979,332 B2 | 12/2005 | Adams |
| 6,772,013 B1 | 8/2004 | Ingle et al. | | 6,984,231 B2 | 1/2006 | Goble et al. |
| 6,775,575 B2 | 8/2004 | Bommannan et al. | | 6,986,769 B2 | 1/2006 | Nelson et al. |
| 6,776,780 B2 | 8/2004 | Mulier et al. | | 6,991,631 B2 | 1/2006 | Woloszko et al. |
| 6,780,177 B2 | 8/2004 | Shafirstein et al. | | 7,001,380 B2 | 2/2006 | Goble |
| 6,780,180 B1 | 8/2004 | Goble et al. | | 7,001,382 B2 | 2/2006 | Gallo, Sr. |
| 6,786,906 B1 | 9/2004 | Cobb | | 7,004,941 B2 | 2/2006 | Tvinnereim et al. |
| 6,796,981 B2 | 9/2004 | Wham et al. | | 7,004,942 B2 | 2/2006 | Laird et al. |
| 6,800,077 B1 | 10/2004 | Mucko et al. | | 7,008,419 B2 | 3/2006 | Shadduck |
| 6,802,842 B2 | 10/2004 | Ellman et al. | | 7,008,421 B2 | 3/2006 | Daniel et al. |
| 6,802,843 B2 | 10/2004 | Truckai et al. | | 7,033,348 B2 | 4/2006 | Alfano et al. |
| 6,808,525 B2 | 10/2004 | Latterell et al. | | 7,033,356 B2 | 4/2006 | Latterell et al. |
| 6,813,520 B2 | 11/2004 | Truckai et al. | | 7,041,096 B2 | 5/2006 | Malis et al. |
| 6,814,714 B1 | 11/2004 | Novak et al. | | 7,041,101 B2 | 5/2006 | Eggers |
| 6,814,731 B2 | 11/2004 | Swanson | | 7,041,102 B2 | 5/2006 | Truckai et al. |
| 6,821,273 B2 | 11/2004 | Mollenauer | | 7,052,494 B2 | 5/2006 | Goble et al. |
| 6,827,713 B2 | 12/2004 | Bek et al. | | 7,060,064 B2 | 6/2006 | Allen et al. |
| 6,827,725 B2 | 12/2004 | Batchelor et al. | | 7,063,670 B2 | 6/2006 | Sampson et al. |
| 6,832,997 B2 | 12/2004 | Uchida et al. | | 7,066,586 B2 | 6/2006 | da Silva |
| 6,835,195 B2 | 12/2004 | Schulze et al. | | 7,066,932 B1 | 6/2006 | Morgan et al. |
| 6,836,688 B2 | 12/2004 | Ingle et al. | | 7,066,936 B2 | 6/2006 | Ryan |
| 6,843,789 B2 | 1/2005 | Goble | | 7,070,596 B1 | 7/2006 | Woloszko et al. |
| 6,845,264 B1 | 1/2005 | Skladnev et al. | | 7,070,604 B1 | 7/2006 | Garito et al. |
| 6,849,073 B2 | 2/2005 | Hoey et al. | | 7,074,217 B2 | 7/2006 | Strul et al. |
| 6,855,145 B2 | 2/2005 | Ciarrocca | | 7,074,219 B2 | 7/2006 | Levine et al. |
| 6,858,028 B2 | 2/2005 | Mulier et al. | | 7,083,601 B1 | 8/2006 | Cosmescu |
| 6,860,882 B2 | 3/2005 | Battles et al. | | 7,087,051 B2 | 8/2006 | Bourne et al. |
| 6,863,669 B2 | 3/2005 | Spitzer | | 7,087,053 B2 | 8/2006 | Vanney |
| 6,864,686 B2 | 3/2005 | Novak et al. | | 7,094,215 B2 | 8/2006 | Davison et al. |
| 6,881,214 B2 | 4/2005 | Cosman et al. | | 7,101,387 B2 | 9/2006 | Garabedian et al. |
| 6,882,885 B2 | 4/2005 | Levy, Jr. et al. | | 7,104,986 B2 | 9/2006 | Hovda et al. |
| 6,887,237 B2 | 5/2005 | McGaffigan | | 7,112,199 B2 | 9/2006 | Cosmescu |
| 6,887,240 B1 | 5/2005 | Lands et al. | | 7,115,139 B2 | 10/2006 | McClurken et al. |
| 6,893,435 B2 | 5/2005 | Goble | | 7,125,406 B2 | 10/2006 | Given |
| 6,893,440 B2 | 5/2005 | Durgin et al. | | 7,147,634 B2 | 12/2006 | Nesbitt |
| 6,896,672 B1 | 5/2005 | Eggers et al. | | 7,147,635 B2 | 12/2006 | Ciarrocca |
| 6,896,674 B1 | 5/2005 | Woloszko et al. | | 7,147,637 B2 | 12/2006 | Goble |
| 6,899,712 B2 | 5/2005 | Moutafis et al. | | 7,147,638 B2 | 12/2006 | Chapman et al. |
| 6,905,497 B2 | 6/2005 | Truckai et al. | | 7,150,746 B2 | 12/2006 | DeCesare et al. |
| 6,905,499 B1 | 6/2005 | Mucko et al. | | 7,150,747 B1 | 12/2006 | McDonald et al. |

| | | |
|---|---|---|
| 7,150,748 B2 | 12/2006 | Ebbutt et al. |
| 7,153,300 B2 | 12/2006 | Goble |
| 7,156,845 B2 | 1/2007 | Mulier et al. |
| 7,166,105 B2 | 1/2007 | Mulier et al. |
| 7,166,106 B2 | 1/2007 | Bartel et al. |
| 7,169,143 B2 | 1/2007 | Eggers et al. |
| 7,169,144 B2 | 1/2007 | Hoey et al. |
| 7,207,471 B2 | 4/2007 | Heinrich et al. |
| 7,232,440 B2 | 6/2007 | Dumbauld et al. |
| 7,247,155 B2 | 7/2007 | Hoey et al. |
| 7,261,711 B2 | 8/2007 | Mulier et al. |
| 7,309,325 B2 | 12/2007 | Mulier et al. |
| 7,311,708 B2 | 12/2007 | McClurken |
| 7,322,974 B2 | 1/2008 | Swoyer et al. |
| 7,361,175 B2 | 4/2008 | Suslov |
| 7,364,579 B2 | 4/2008 | Mulier et al. |
| 2001/0014819 A1 | 8/2001 | Ingle et al. |
| 2001/0020167 A1 | 9/2001 | Woloszko et al. |
| 2001/0023365 A1 | 9/2001 | Medhkour et al. |
| 2001/0025178 A1 | 9/2001 | Mulier et al. |
| 2001/0032002 A1 | 10/2001 | McClurken et al. |
| 2001/0039419 A1 | 11/2001 | Francischelli et al. |
| 2001/0041921 A1 | 11/2001 | Mulier et al. |
| 2001/0051802 A1 | 12/2001 | Woloszko et al. |
| 2001/0051804 A1 | 12/2001 | Mulier et al. |
| 2002/0002393 A1 | 1/2002 | Mitchell |
| 2002/0010463 A1 | 1/2002 | Mulier et al. |
| 2002/0013582 A1 | 1/2002 | Mulier et al. |
| 2002/0016589 A1 | 2/2002 | Swartz et al. |
| 2002/0019628 A1 | 2/2002 | Comben |
| 2002/0022870 A1 | 2/2002 | Truckai et al. |
| 2002/0026186 A1 | 2/2002 | Woloszko et al. |
| 2002/0026187 A1 | 2/2002 | Swanson |
| 2002/0029036 A1 | 3/2002 | Goble et al. |
| 2002/0035361 A1 | 3/2002 | Houser et al. |
| 2002/0035387 A1 | 3/2002 | Mulier et al. |
| 2002/0049438 A1 | 4/2002 | Sharkey et al. |
| 2002/0049439 A1 | 4/2002 | Mulier et al. |
| 2002/0049483 A1 | 4/2002 | Knowlton |
| 2002/0058933 A1 | 5/2002 | Christopherson et al. |
| 2002/0058935 A1 | 5/2002 | Hoey et al. |
| 2002/0062123 A1 | 5/2002 | McClurken et al. |
| 2002/0095150 A1 | 7/2002 | Goble |
| 2002/0095151 A1 | 7/2002 | Dahla et al. |
| 2002/0095152 A1 | 7/2002 | Ciarrocca et al. |
| 2002/0099366 A1 | 7/2002 | Dahla et al. |
| 2002/0115991 A1 | 8/2002 | Edwards |
| 2002/0115992 A1 | 8/2002 | Utley et al. |
| 2002/0120259 A1 | 8/2002 | Lettice et al. |
| 2002/0120260 A1 | 8/2002 | Morris et al. |
| 2002/0120261 A1 | 8/2002 | Morris et al. |
| 2002/0128650 A1 | 9/2002 | McClurken |
| 2002/0133148 A1 | 9/2002 | Daniel et al. |
| 2002/0151884 A1 | 10/2002 | Hoey et al. |
| 2002/0156511 A1 | 10/2002 | Habib |
| 2002/0161364 A1 | 10/2002 | Mulier et al. |
| 2002/0169446 A1 | 11/2002 | Mulier et al. |
| 2002/0177846 A1 | 11/2002 | Mulier et al. |
| 2002/0183733 A1 | 12/2002 | Mulier et al. |
| 2002/0188284 A1 | 12/2002 | To et al. |
| 2002/0193851 A1* | 12/2002 | Silverman et al. ........... 607/101 |
| 2002/0198524 A1 | 12/2002 | Mulier et al. |
| 2003/0004510 A1 | 1/2003 | Wham et al. |
| 2003/0032955 A1 | 2/2003 | Mulier et al. |
| 2003/0073989 A1 | 4/2003 | Hoey et al. |
| 2003/0114850 A1 | 6/2003 | McClurken et al. |
| 2003/0181902 A1 | 9/2003 | Mulier et al. |
| 2003/0204185 A1 | 10/2003 | Sherman et al. |
| 2003/0216733 A1 | 11/2003 | McClurken et al. |
| 2004/0015162 A1 | 1/2004 | McGaffigan |
| 2004/0015163 A1 | 1/2004 | Buysse et al. |
| 2004/0015215 A1 | 1/2004 | Fredricks et al. |
| 2004/0015216 A1 | 1/2004 | DeSisto |
| 2004/0015218 A1 | 1/2004 | Finch et al. |
| 2004/0019350 A1 | 1/2004 | O'Brien |
| 2004/0024395 A1 | 2/2004 | Ellman et al. |
| 2004/0024396 A1 | 2/2004 | Eggers |
| 2004/0024398 A1 | 2/2004 | Hovda et al. |
| 2004/0024399 A1 | 2/2004 | Sharps et al. |
| 2004/0030327 A1 | 2/2004 | Golan |
| 2004/0030328 A1 | 2/2004 | Eggers et al. |
| 2004/0030330 A1 | 2/2004 | Brassell et al. |
| 2004/0030332 A1 | 2/2004 | Knowlton et al. |
| 2004/0030333 A1 | 2/2004 | Goble |
| 2004/0034340 A1 | 2/2004 | Biscup |
| 2004/0034346 A1 | 2/2004 | Stern et al. |
| 2004/0034349 A1 | 2/2004 | Kirwan, Jr. et al. |
| 2004/0034400 A1 | 2/2004 | Ingle et al. |
| 2004/0039429 A1 | 2/2004 | Daniel et al. |
| 2004/0044341 A1 | 3/2004 | Truckai et al. |
| 2004/0054363 A1 | 3/2004 | Vaska et al. |
| 2004/0054365 A1 | 3/2004 | Goble |
| 2004/0054366 A1 | 3/2004 | Davison et al. |
| 2004/0054369 A1 | 3/2004 | Nelson et al. |
| 2004/0054370 A1 | 3/2004 | Given |
| 2004/0059328 A1 | 3/2004 | Daniel et al. |
| 2004/0059363 A1 | 3/2004 | Alvarez et al. |
| 2004/0064023 A1 | 4/2004 | Ryan et al. |
| 2004/0064137 A1 | 4/2004 | Pellegrino et al. |
| 2004/0068306 A1 | 4/2004 | Shadduck |
| 2004/0068307 A1 | 4/2004 | Goble |
| 2004/0073205 A1 | 4/2004 | Treat et al. |
| 2004/0073208 A1 | 4/2004 | Sutter |
| 2004/0078034 A1 | 4/2004 | Acker et al. |
| 2004/0078037 A1 | 4/2004 | Batchelor et al. |
| 2004/0078038 A1 | 4/2004 | Desinger et al. |
| 2004/0082946 A1 | 4/2004 | Malis et al. |
| 2004/0082952 A1 | 4/2004 | Dycus et al. |
| 2004/0087937 A1 | 5/2004 | Eggers et al. |
| 2004/0087939 A1 | 5/2004 | Eggers et al. |
| 2004/0087940 A1 | 5/2004 | Jahns et al. |
| 2004/0087943 A1 | 5/2004 | Dycus et al. |
| 2004/0088029 A1 | 5/2004 | Yamamoto |
| 2004/0092925 A1 | 5/2004 | Rizoiu et al. |
| 2004/0092926 A1 | 5/2004 | Hoey et al. |
| 2004/0097919 A1 | 5/2004 | Wellman et al. |
| 2004/0102770 A1 | 5/2004 | Goble |
| 2004/0102824 A1 | 5/2004 | Sharkey et al. |
| 2004/0116923 A1 | 6/2004 | Desinger |
| 2004/0122420 A1 | 6/2004 | Amoah |
| 2004/0122423 A1 | 6/2004 | Dycus et al. |
| 2004/0122494 A1 | 6/2004 | Eggers et al. |
| 2004/0138654 A1 | 7/2004 | Goble |
| 2004/0138655 A1 | 7/2004 | McClurken et al. |
| 2004/0138657 A1 | 7/2004 | Bourne et al. |
| 2004/0143257 A1 | 7/2004 | Fuimaono |
| 2004/0143258 A1 | 7/2004 | Fuimaono |
| 2004/0143259 A1 | 7/2004 | Mulier et al. |
| 2004/0143263 A1 | 7/2004 | Schechter et al. |
| 2004/0147902 A1 | 7/2004 | McGuckin, Jr. et al. |
| 2004/0147916 A1 | 7/2004 | Baker |
| 2004/0147922 A1 | 7/2004 | Keppel |
| 2004/0147925 A1 | 7/2004 | Buysse et al. |
| 2004/0162552 A1 | 8/2004 | McClurken |
| 2004/0162554 A1 | 8/2004 | Lee et al. |
| 2004/0162557 A1 | 8/2004 | Tetzlaff et al. |
| 2004/0162572 A1 | 8/2004 | Sauer |
| 2004/0167508 A1 | 8/2004 | Wham et al. |
| 2004/0172111 A1 | 9/2004 | Hijii et al. |
| 2004/0176760 A1 | 9/2004 | Qiu |
| 2004/0176761 A1 | 9/2004 | Desinger |
| 2004/0176762 A1 | 9/2004 | Lawes et al. |
| 2004/0181219 A1 | 9/2004 | Goble et al. |
| 2004/0181250 A1 | 9/2004 | Adams et al. |
| 2004/0186469 A1 | 9/2004 | Woloszko et al. |
| 2004/0186470 A1 | 9/2004 | Goble et al. |

| | | | | | | |
|---|---|---|---|---|---|---|
| 2004/0186535 A1 | 9/2004 | Knowlton | | 2005/0131402 A1 | 6/2005 | Ciarrocca et al. |
| 2004/0193148 A1 | 9/2004 | Wham et al. | | 2005/0137590 A1 | 6/2005 | Lawes et al. |
| 2004/0193150 A1 | 9/2004 | Sharkey et al. | | 2005/0137662 A1 | 6/2005 | Morris et al. |
| 2004/0193152 A1 | 9/2004 | Sutton et al. | | 2005/0143729 A1 | 6/2005 | Francischelli et al. |
| 2004/0193211 A1 | 9/2004 | Voegele et al. | | 2005/0154385 A1 | 7/2005 | Heim et al. |
| 2004/0199156 A1 | 10/2004 | Rioux et al. | | 2005/0154433 A1 | 7/2005 | Levy, Jr. et al. |
| 2004/0199160 A1 | 10/2004 | Slater | | 2005/0159739 A1 | 7/2005 | Paul et al. |
| 2004/0206365 A1 | 10/2004 | Knowlton | | 2005/0159740 A1 | 7/2005 | Paul et al. |
| 2004/0210213 A1 | 10/2004 | Fuimaono et al. | | 2005/0159778 A1 | 7/2005 | Heinrich et al. |
| 2004/0210214 A1 | 10/2004 | Knowlton | | 2005/0159797 A1 | 7/2005 | Chandran et al. |
| 2004/0215181 A1 | 10/2004 | Christopherson et al. | | 2005/0165444 A1 | 7/2005 | Hart et al. |
| 2004/0215182 A1 | 10/2004 | Lee | | 2005/0171524 A1 | 8/2005 | Stern et al. |
| 2004/0215183 A1 | 10/2004 | Hoey et al. | | 2005/0171526 A1 | 8/2005 | Rioux et al. |
| 2004/0215184 A1 | 10/2004 | Eggers et al. | | 2005/0171532 A1 | 8/2005 | Ciarrocca |
| 2004/0215185 A1 | 10/2004 | Truckai et al. | | 2005/0171533 A1 | 8/2005 | Latterell et al. |
| 2004/0215188 A1 | 10/2004 | Mulier et al. | | 2005/0171534 A1 | 8/2005 | Habib |
| 2004/0215235 A1 | 10/2004 | Jackson et al. | | 2005/0171583 A1 | 8/2005 | Mosher et al. |
| 2004/0215296 A1 | 10/2004 | Ganz et al. | | 2005/0177150 A1 | 8/2005 | Amoah et al. |
| 2004/0220561 A1 | 11/2004 | Kirwan, Jr. et al. | | 2005/0177209 A1 | 8/2005 | Leung et al. |
| 2004/0220562 A1 | 11/2004 | Garabedian et al. | | 2005/0187543 A1 | 8/2005 | Underwood et al. |
| 2004/0225288 A1 | 11/2004 | Buysse et al. | | 2005/0187599 A1 | 8/2005 | Sharkey et al. |
| 2004/0230190 A1 | 11/2004 | Dahla et al. | | 2005/0203503 A1 | 9/2005 | Edwards et al. |
| 2004/0236322 A1 | 11/2004 | Mulier et al. | | 2005/0203504 A1 | 9/2005 | Wham et al. |
| 2004/0236324 A1 | 11/2004 | Muller et al. | | 2005/0209591 A1 | 9/2005 | Sutter |
| 2004/0243125 A1 | 12/2004 | Dycus et al. | | 2005/0209621 A1 | 9/2005 | Gordon et al. |
| 2004/0243163 A1 | 12/2004 | Casiano et al. | | 2005/0222602 A1 | 10/2005 | Sutter et al. |
| 2004/0249371 A1 | 12/2004 | Dycus et al. | | 2005/0222611 A1 | 10/2005 | WeitKamp |
| 2004/0249374 A1 | 12/2004 | Tetzlaff et al. | | 2005/0228372 A1 | 10/2005 | Truckai et al. |
| 2004/0249425 A1 | 12/2004 | Roy et al. | | 2005/0245918 A1 | 11/2005 | Sliwa, Jr. et al. |
| 2004/0260279 A1 | 12/2004 | Goble et al. | | 2005/0245921 A1 | 11/2005 | Strul et al. |
| 2004/0260280 A1 | 12/2004 | Sartor | | 2005/0245922 A1 | 11/2005 | Goble |
| 2004/0260368 A1 | 12/2004 | Ingle et al. | | 2005/0245923 A1 | 11/2005 | Christopherson et al. |
| 2005/0010205 A1 | 1/2005 | Hovda et al. | | 2005/0250477 A1 | 11/2005 | Eastwood et al. |
| 2005/0010212 A1 | 1/2005 | McClurken et al. | | 2005/0251128 A1 | 11/2005 | Amoah |
| 2005/0015085 A1 | 1/2005 | McClurken et al. | | 2005/0251134 A1 | 11/2005 | Woloszko et al. |
| 2005/0015086 A1 | 1/2005 | Platt | | 2005/0256519 A1 | 11/2005 | Goble et al. |
| 2005/0015130 A1 | 1/2005 | Gill | | 2005/0261676 A1 | 11/2005 | Hall et al. |
| 2005/0021025 A1 | 1/2005 | Buysse et al. | | 2005/0261677 A1 | 11/2005 | Hall et al. |
| 2005/0021026 A1 | 1/2005 | Baily | | 2005/0267465 A1 | 12/2005 | Hillier et al. |
| 2005/0021027 A1 | 1/2005 | Shields et al. | | 2005/0267467 A1 | 12/2005 | Paul et al. |
| 2005/0033278 A1 | 2/2005 | McClurken et al. | | 2005/0267468 A1 | 12/2005 | Truckai et al. |
| 2005/0033292 A1 | 2/2005 | Teitelbaum et al. | | 2005/0267469 A1 | 12/2005 | Blocher |
| 2005/0038471 A1 | 2/2005 | Chan et al. | | 2005/0273092 A1 | 12/2005 | G. et al. |
| 2005/0043728 A1 | 2/2005 | Ciarrocca | | 2005/0273097 A1 | 12/2005 | Ryan |
| 2005/0049583 A1 | 3/2005 | Swanson | | 2005/0277915 A1 | 12/2005 | DeCesare et al. |
| 2005/0049586 A1 | 3/2005 | Daniel et al. | | 2005/0277916 A1 | 12/2005 | DeCesare et al. |
| 2005/0055019 A1 | 3/2005 | Skarda | | 2005/0277917 A1 | 12/2005 | Garito et al. |
| 2005/0055020 A1 | 3/2005 | Skarda | | 2005/0283147 A1 | 12/2005 | Yachi |
| 2005/0059966 A1 | 3/2005 | McClurken et al. | | 2005/0283148 A1 | 12/2005 | Janssen et al. |
| 2005/0070888 A1 | 3/2005 | Dimatteo et al. | | 2005/0283149 A1 | 12/2005 | Thorne et al. |
| 2005/0070891 A1 | 3/2005 | DeSisto | | 2005/0283150 A1 | 12/2005 | Moutafis et al. |
| 2005/0070894 A1 | 3/2005 | McClurken | | 2005/0283151 A1 | 12/2005 | Ebbutt et al. |
| 2005/0070896 A1 | 3/2005 | Daniel et al. | | 2005/0288661 A1 | 12/2005 | Sauvageau et al. |
| 2005/0080410 A1 | 4/2005 | Rioux et al. | | 2005/0288665 A1 | 12/2005 | Woloszko |
| 2005/0080413 A1 | 4/2005 | Canady | | 2006/0004356 A1 | 1/2006 | Bilski et al. |
| 2005/0085804 A1 | 4/2005 | McGaffigan | | 2006/0009760 A1 | 1/2006 | Mulier et al. |
| 2005/0085809 A1 | 4/2005 | Mucko et al. | | 2006/0009762 A1 | 1/2006 | Whayne |
| 2005/0085880 A1 | 4/2005 | Truckai et al. | | 2006/0015097 A1 | 1/2006 | Mulier et al. |
| 2005/0090816 A1 | 4/2005 | McClurken et al. | | 2006/0020265 A1 | 1/2006 | Ryan |
| 2005/0090819 A1 | 4/2005 | Goble | | 2006/0025765 A1 | 2/2006 | Landman et al. |
| 2005/0096649 A1 | 5/2005 | Adams | | 2006/0025766 A1 | 2/2006 | Heinrich et al. |
| 2005/0096651 A1 | 5/2005 | Truckai et al. | | 2006/0030912 A1 | 2/2006 | Eggers et al. |
| 2005/0101951 A1 | 5/2005 | Wham et al. | | 2006/0036235 A1 | 2/2006 | Swoyer et al. |
| 2005/0101952 A1 | 5/2005 | Lands et al. | | 2006/0036237 A1 | 2/2006 | Davison et al. |
| 2005/0101965 A1 | 5/2005 | Ryan | | 2006/0036239 A1 | 2/2006 | Canady |
| 2005/0107778 A1 | 5/2005 | Rioux et al. | | 2006/0041254 A1 | 2/2006 | Francischelli et al. |
| 2005/0107779 A1 | 5/2005 | Ellman et al. | | 2006/0041255 A1 | 2/2006 | Eggers et al. |
| 2005/0107784 A1 | 5/2005 | Moses et al. | | 2006/0047275 A1 | 3/2006 | Goble |
| 2005/0107786 A1 | 5/2005 | Canady | | 2006/0047280 A1 | 3/2006 | Goble et al. |
| 2005/0113820 A1 | 5/2005 | Goble et al. | | 2006/0047331 A1 | 3/2006 | Lax et al. |
| 2005/0113825 A1 | 5/2005 | Cosmescu | | 2006/0052770 A1 | 3/2006 | Mulier et al. |
| 2005/0124987 A1 | 6/2005 | Goble | | 2006/0064085 A1 | 3/2006 | Schechter et al. |
| 2005/0130929 A1 | 6/2005 | Boyd | | 2006/0064101 A1 | 3/2006 | Arramon |

| | | | | | | |
|---|---|---|---|---|---|---|
| 2006/0074411 A1 | 4/2006 | Carmel et al. | | 2006/0241577 A1 | 10/2006 | Balbierz et al. |
| 2006/0074414 A1 | 4/2006 | Mulier et al. | | 2006/0241587 A1 | 10/2006 | Heim et al. |
| 2006/0079872 A1 | 4/2006 | Eggleston | | 2006/0241588 A1 | 10/2006 | Heim et al. |
| 2006/0079888 A1 | 4/2006 | Mulier et al. | | 2006/0241589 A1 | 10/2006 | Heim et al. |
| 2006/0084968 A1 | 4/2006 | Truckai et al. | | 2006/0247614 A1 | 11/2006 | Sampson et al. |
| 2006/0095026 A1 | 5/2006 | Ricart et al. | | 2006/0259025 A1 | 11/2006 | Dahla |
| 2006/0095031 A1 | 5/2006 | Ormsby | | 2006/0259031 A1 | 11/2006 | Carmel et al. |
| 2006/0095034 A1 | 5/2006 | Garito et al. | | 2006/0259070 A1 | 11/2006 | Livneh |
| 2006/0095075 A1 | 5/2006 | Burkinshaw et al. | | 2006/0264927 A1 | 11/2006 | Ryan |
| 2006/0095103 A1 | 5/2006 | Eggers et al. | | 2006/0264929 A1 | 11/2006 | Goble et al. |
| 2006/0100619 A1 | 5/2006 | McClurken et al. | | 2006/0264931 A1 | 11/2006 | Chapman et al. |
| 2006/0106376 A1 | 5/2006 | Godara et al. | | 2006/0271033 A1 | 11/2006 | Ein-Gal |
| 2006/0106379 A1 | 5/2006 | O'Brien et al. | | 2006/0271036 A1 | 11/2006 | Garabedian et al. |
| 2006/0111705 A1 | 5/2006 | Janzen et al. | | 2006/0271042 A1 | 11/2006 | Latterell et al. |
| 2006/0111709 A1 | 5/2006 | Goble et al. | | 2006/0276783 A1 | 12/2006 | Cosmescu |
| 2006/0111710 A1 | 5/2006 | Goble et al. | | 2006/0276785 A1 | 12/2006 | Asahara et al. |
| 2006/0111711 A1 | 5/2006 | Goble | | 2007/0000501 A1 | 1/2007 | Wert et al. |
| 2006/0111741 A1 | 5/2006 | Nardella | | 2007/0010812 A1 | 1/2007 | Mittelstein et al. |
| 2006/0116675 A1 | 6/2006 | McClurken et al. | | 2007/0016182 A1 | 1/2007 | Lipson et al. |
| 2006/0122593 A1 | 6/2006 | Jun et al. | | 2007/0049920 A1 | 3/2007 | McClurken et al. |
| 2006/0129145 A1 | 6/2006 | Woloszko et al. | | 2007/0093808 A1 | 4/2007 | Mulier et al. |
| 2006/0129185 A1 | 6/2006 | Paternuosto | | 2007/0118114 A1 | 5/2007 | Mulier et al. |
| 2006/0142757 A1 | 6/2006 | Daniel et al. | | 2007/0208332 A1 | 9/2007 | Mulier et al. |
| 2006/0149225 A1 | 7/2006 | McClurken | | 2008/0015563 A1 | 1/2008 | Hoey et al. |
| 2006/0167446 A1 | 7/2006 | Pozzato | | 2008/0066752 A1 | 3/2008 | Baker et al. |
| 2006/0167449 A1 | 7/2006 | Mulier et al. | | | | |
| 2006/0167451 A1 | 7/2006 | Cropper | | | | |
| 2006/0178667 A1 | 8/2006 | Sartor et al. | | | | |
| 2006/0178668 A1 | 8/2006 | Albritton et al. | | | | |
| 2006/0178670 A1 | 8/2006 | Woloszko et al. | | | | |
| 2006/0178699 A1 | 8/2006 | Surti | | | | |
| 2006/0184164 A1 | 8/2006 | Malis et al. | | | | |
| 2006/0184167 A1 | 8/2006 | Vaska et al. | | | | |
| 2006/0189977 A1 | 8/2006 | Allen et al. | | | | |
| 2006/0189979 A1 | 8/2006 | Esch et al. | | | | |
| 2006/0195079 A1 | 8/2006 | Eberl | | | | |
| 2006/0200123 A1 | 9/2006 | Ryan | | | | |
| 2006/0217700 A1 | 9/2006 | Garito et al. | | | | |
| 2006/0217701 A1 | 9/2006 | Young et al. | | | | |
| 2006/0217707 A1 | 9/2006 | Daniel et al. | | | | |
| 2006/0224154 A1 | 10/2006 | Shadduck et al. | | | | |
| 2006/0235286 A1 | 10/2006 | Stone et al. | | | | |
| 2006/0235377 A1 | 10/2006 | Earley et al. | | | | |
| 2006/0235379 A1 | 10/2006 | McClurken et al. | | | | |

FOREIGN PATENT DOCUMENTS

| | | |
|---|---|---|
| EP | 0 175 595 | 3/1986 |
| EP | 1 095 627 A1 | 5/2001 |
| FR | 2 235 669 | 1/1975 |
| JP | 57-117843 | 7/1982 |
| JP | 5-092009 | 4/1993 |
| JP | 7-124245 | 5/1995 |
| WO | WO 97/05829 A1 | 2/1997 |
| WO | WO 98/38932 A1 | 9/1998 |
| WO | WO 99/66850 A1 | 12/1999 |
| WO | WO 00/78240 A1 | 12/2000 |
| WO | WO 01/28444 A1 | 4/2001 |
| WO | WO 01/80757 A2 | 11/2001 |
| WO | WO 2005/122938 A1 | 12/2005 |
| WO | WO 2006/062916 A2 | 6/2006 |
| WO | WO 2006/062939 A2 | 6/2006 |

* cited by examiner

FLUID-ASSISTED MEDICAL DEVICES, SYSTEMS AND METHODS

This application is a continuation of U.S. patent application Ser. No. 10/494,597 filed May 4, 2004, now U.S. Pat. No. 7,311,708, which is a 371 application of PCT application PCT/US02/39701, filed Dec. 11, 2002 which claims priority to U.S. Provisional application No. 60/340,429, filed Dec. 12, 2001, the entire disclosures of which are incorporated herein by reference.

FIELD OF THE INVENTION

This invention relates generally to the field of medical devices, methods and systems for use upon a body during surgery. More particularly, the invention relates to electrosurgical devices, methods and systems for use upon tissues of a human body during therapeutic endoscopy.

BACKGROUND

Electrosurgical devices configured for use with a dry tip use electrical energy, most commonly radio frequency (RF) energy, to cut tissue or to cauterize blood vessels. During use, a voltage gradient is created at the tip of the device, thereby inducing current flow and related heat generation in the tissue. With sufficiently high levels of electrical energy, the heat generated is sufficient to cut the tissue and, advantageously, to stop the bleeding from severed blood vessels.

Current dry tip electrosurgical devices can cause the temperature of tissue being treated to rise significantly higher than 100° C., resulting in tissue desiccation, tissue sticking to the electrodes, tissue perforation, char formation and smoke generation. Peak tissue temperatures as a result of RF treatment of target tissue can be as high as 320° C., and such high temperatures can be transmitted to adjacent tissue via thermal diffusion. Undesirable results of such transmission to adjacent tissue include unintended thermal damage to the tissue.

Using saline to couple RF electrical energy to tissue inhibits such undesirable effects as sticking, desiccation, smoke production and char formation. One key factor is inhibiting tissue desiccation, which occurs if tissue temperature exceeds 100° C. and all of the intracellular water boils away, leaving the tissue extremely dry and much less electrically conductive. However, an uncontrolled or abundant flow rate of saline can provide too much cooling at the electrode/tissue interface. This cooling reduces the temperature of the target tissue being treated, and the rate at which tissue thermal coagulation occurs is determined by tissue temperature. This, in turn, can result in longer treatment time to achieve the desired tissue temperature for treatment of the tissue. Long treatment times are undesirable for surgeons since it is in the best interest of the patient, physician and hospital to perform surgical procedures as quickly as possible.

RF energy delivered to tissue can be unpredictable and often not optimal when using general-purpose generators. Most general-purpose RF generators have modes for different waveforms (e.g. cut, coagulation, or a blend of these two) and device types (e.g. monopolar, bipolar), as well as power levels that can be set in watts. However, once these settings are chosen, the actual power delivered to tissue and associated heat generated can vary dramatically over time as tissue impedance changes over the course of RF treatment. This is because the power delivered by most generators is a function of tissue impedance, with the power ramping down as impedance either decreases toward zero or increases significantly to several thousand ohms. Current dry tip electrosurgical devices are not configured to address a change in power provided by the generator as tissue impedance changes or the associated effect on tissue and rely on the surgeon's expertise to overcome this limitation.

One medical condition which employs RF energy in treatment is gastrointestinal (GI) bleeding, with such treatment typically administered via gastrointestinal endoscopy. Bleeding in the upper gastrointestinal tract may result from, for example, peptic ulcers, gastritis, gastric cancer, vascular malformations such as varices (e.g. esophageal) and other lesions. Bleeding in the lower gastrointestinal tract may result from, for example, vascular malformations such as hemorrhoidal varices.

Peptic ulcer bleeding is one of the most common types of non-variceal upper gastrointestinal bleeding. Peptic ulcer bleeding results from the combined action of pepsin and hydrochloric acid in the gastric or digestive juices of the stomach. Peptic ulcers further include, for example, gastric ulcers, an eroded area in the lining (gastric mucosa) of the stomach, and duodenal ulcers, an eroded area in the lining (duodenal mucosa) of the duodenum. Peptic ulcers may also be found in Meckel's diverticulum.

Endoscopic modalities for the treatment of upper gastrointestinal bleeding include injection therapy (e.g. diluted epinephrine, sclerosants, thrombogenic substances, fibrin sealant), mechanical clips and so called thermal (heating) methods. Thermal methods are often divided into so called non-contact thermal methods and contact thermal methods. Non-contact thermal methods include laser treatment and, more recently, argon plasma coagulation (APC). Thermal contact methods include multipolar electrocoagulation and thermal coagulation probes.

Non-contact thermal probe methods depend on the heating of tissue protein, contraction of the arterial wall and vessel shrinkage. One drawback of non-contact thermal methods is the "heat sink effect" where flowing arterial blood leads to dissipation of the thermal energy. Because of the greater tissue penetration, the neodymium: yttrium aluminum garnet (Nd:YAG) laser is generally superior to the argon laser for ulcer hemostasis. In any event, laser units are expensive, bulky and generally not portable. They are also difficult to use as an en face view of the bleeding ulcer is often required. For these reasons, laser photocoagulation has generally fallen out of favor for the treatment of ulcer bleeding. The argon plasma coagulator uses a flowing stream of argon gas as the conductor for electrocoagulation. This method is generally effective for mucosal bleeding but may not be effective in coagulating an eroded artery in a bleeding ulcer. Also, as flowing gas is required, care must be taken to avoid overdistention of the stomach during treatment.

Contact thermal probes utilize the principle of "coaptive coagulation". First, mechanical pressure is applied to the bleeding vessel to compress the vessel before heat or electrical energy is applied to seal the bleeding vessel. Compression of the blood vessel also reduces the blood flow and reduces the heat sink effect. Multiple pulses of energy are given to coagulate the bleeding vessel to achieve hemostasis. These methods are effective in hemostasis but carry a potential risk of inducing bleeding when an adherent probe is pulled off a bleeding vessel. Furthermore, contact devices require accurate targeting of the bleeding vessel for successful ulcer hemostasis.

Multipolar electrocoagulation devices include the BICAP® Hemostasis Probe from ACMI Circon (300 Stillwater Avenue, Stamford, Conn. 06902) and the Gold Probe™ from Microvasive (480 Pleasant Street, Watertown, Mass. 02172). A third multipolar electrocoagulation device is the Injector-Gold Probe™, also from Microvasive, which incorporates an injection needle for use with epinephrine.

According to Dr. Joseph Leung's publication entitled "Endoscopic Management of Peptic Ulcer Bleeding", an "ideal" endoscopic hemostatic device should have the following properties. It should be effective in hemostasis, safe, inexpensive, easy to apply and portable. Thus, cost and non-portability issues associated with laser therapy have generally made it a less favorable treatment for ulcer hemostasis. Consequently, electrocoagulation or thermal coagulation have largely replaced laser therapy as a more routine treatment. Injection therapy generally has an advantage over the above contact thermal devices in that the injection does not need to be very accurate and can be performed through a pool of blood, but the cost of the medication is a disadvantage.

Turning to the argon plasma coagulator, according to in the publication "A Randomized Prospective Study of Endoscopic Hemostasis with Argon Plasma Coagulator (APC) Compared to Gold Probe™ (GP) for Bleeding GI Angiomas", Jutabha and colleagues compared the efficacy and safety of APC and GP for hemostasis of bleeding GI angiomas and describe the advantages and disadvantages of each type of treatment for angioma patients. Thirty-four patients with angiomas as the cause of acute or chronic GI bleeding, not responsive to iron supplementation alone, were stratified by syndrome (i.e., UGI, LGI angiomas; watermelon stomach; jejunal angiomas; radiation telangiectasia) and randomized to treatment in a prospective study: 16 to APC and 18 to GP.

According to the publication, there were 2 major complications of APC. While there were no significant differences between most clinical outcomes of APC versus GP patients, investigators observed that APC was significantly slower than GP and more difficult to use because of several features of APC: it could not coagulate through blood or water, smoke was common which interfered with visualization and increased gut motility, tamponade of bleeders was not possible, and tangential coagulation was difficult or often blind.

The differences between APC and GP were more marked with multiple angioma syndromes. Although APC is a "no touch technique," the catheter was difficult to hold 2-3 mm off the mucosa, which affords the best coagulation of a dry field. These features resulted in 6 failures and crossovers with APC and none with GP. There were no major disadvantages of GP except that coagulum needed to be cleaned off the tip after treatment of multiple angiomas. The authors concluded that for hemostasis of bleeding angiomas, both the APC and GP were effective, but there were substantial problems with the newer APC device, and overall the GP performed better.

In light of the above, what is needed is a endoscopic hemostatic device which offers advantages of both the so called non-contact and contact devices and methods without associated disadvantages. Thus, for example, what is needed is an endoscopic hemostatic device which is preferably portable and inexpensive. Furthermore, preferably the device should be capable of tissue contact and tamponage associated with coaptive coagulation to reduce the heat sink effect and facilitate treatment of an eroded artery, but be less likely to induce bleeding when the device is removed from a treated vessel. Furthermore, preferably the device should be capable of coagulation through blood or water (i.e. without contact) as well as tangential coagulation, without generating smoke which raises possible problems of visualization, gut motility or stomach overdistenation. Furthermore, preferably the device should be capable of generating tissue hemostasis at a temperature high enough to result in tissue shrinkage, but at a temperature low enough not to necessarily create char (e.g. dried blood) formation or produce scabs, which maybe subsequently dissolved by digestive juices a result in rebleeding. Furthermore, preferably the device should be capable of use on any surface of the GI tract without regard for orientation. In other words, for example, preferably the device may be used to treat any surface of the stomach, whether above, below or to the side.

SUMMARY OF THE INVENTION

According to one aspect of the invention, an electrosurgical device and methods for use are provided which comprises an electrosurgical device outer surface and includes a probe body, at least one conductor pair comprising a first electrode separated by a gap from a second electrode, and means in fluid communication with the lumen of a tube for distributing a fluid provided from the lumen of the tube to at least a portion of the surface of the electrosurgical device.

Also according to the invention, a catheter assembly is provided which comprises a catheter having a distal end and a lumen, and an electrosurgical device assembled with the catheter adjacent the distal end thereof. The electrosurgical device comprises an electrosurgical device outer surface and includes a probe body, at least one conductor pair comprising a first electrode separated by a gap from a second electrode, and means in fluid communication with the lumen of the catheter for distributing a fluid provided from the lumen of the catheter to at least a portion of the surface of the electrosurgical device.

According to another embodiment of the invention, a catheter assembly is provided which comprises a catheter having a distal end and a lumen, and an electrosurgical device assembled with the catheter adjacent the distal end thereof. The electrosurgical device comprises an electrosurgical device outer surface and includes a probe body, at least one conductor pair comprising a first electrode separated by a gap from a second electrode, and a fluid flow manifold located within the probe body. The fluid flow manifold includes at least one flow passage extending longitudinally within the probe body and at least one flow passage lateral to the longitudinal flow passage. The longitudinal flow passage comprises a longitudinal flow passage fluid entrance opening in fluid communication with the lumen of the catheter and is at least partially defined distally by an occlusion. The lateral flow passage is in fluid communication with the longitudinal flow passage and extends through the probe body from the longitudinal flow passage towards the electrosurgical device outer surface.

According to another embodiment of the invention, a catheter assembly is provided which comprises a catheter, the catheter having a distal end and a lumen, and an electrosurgical device assembled with the catheter adjacent the distal end thereof. The electrosurgical device comprises an electrosurgical device outer surface and includes a probe body, at least one conductor pair, the conductor pair comprising a first electrode separated by a gap from a second electrode, and means in fluid communication with the lumen of the catheter for distributing a fluid provided from the lumen of the catheter to at least a portion of the surface of the electrosurgical device.

According to another embodiment of the invention, a medical device is provided which comprises a catheter tube having a distal end and a lumen, and configured to assist in applying tamponage to a bleeding source in a gastrointestinal tract when flexed. A catheter tip having a catheter tip outer surface is assembled with the tube adjacent the distal end of the tube. The catheter tip comprises a probe body comprising an electrically insulative material, at least one electrode pair located on the probe body which comprises a first electrode spaced from a second electrode, and a fluid distribution manifold to direct a fluid from inside the probe body towards the tip outer surface. The manifold comprises a central passage within the probe body and a plurality of lateral passages which extend from the central passage towards the tip outer surface. An extendable injection needle is housed within the central passage to provide treatment to tissue.

DETAILED DESCRIPTION

Figure 1:
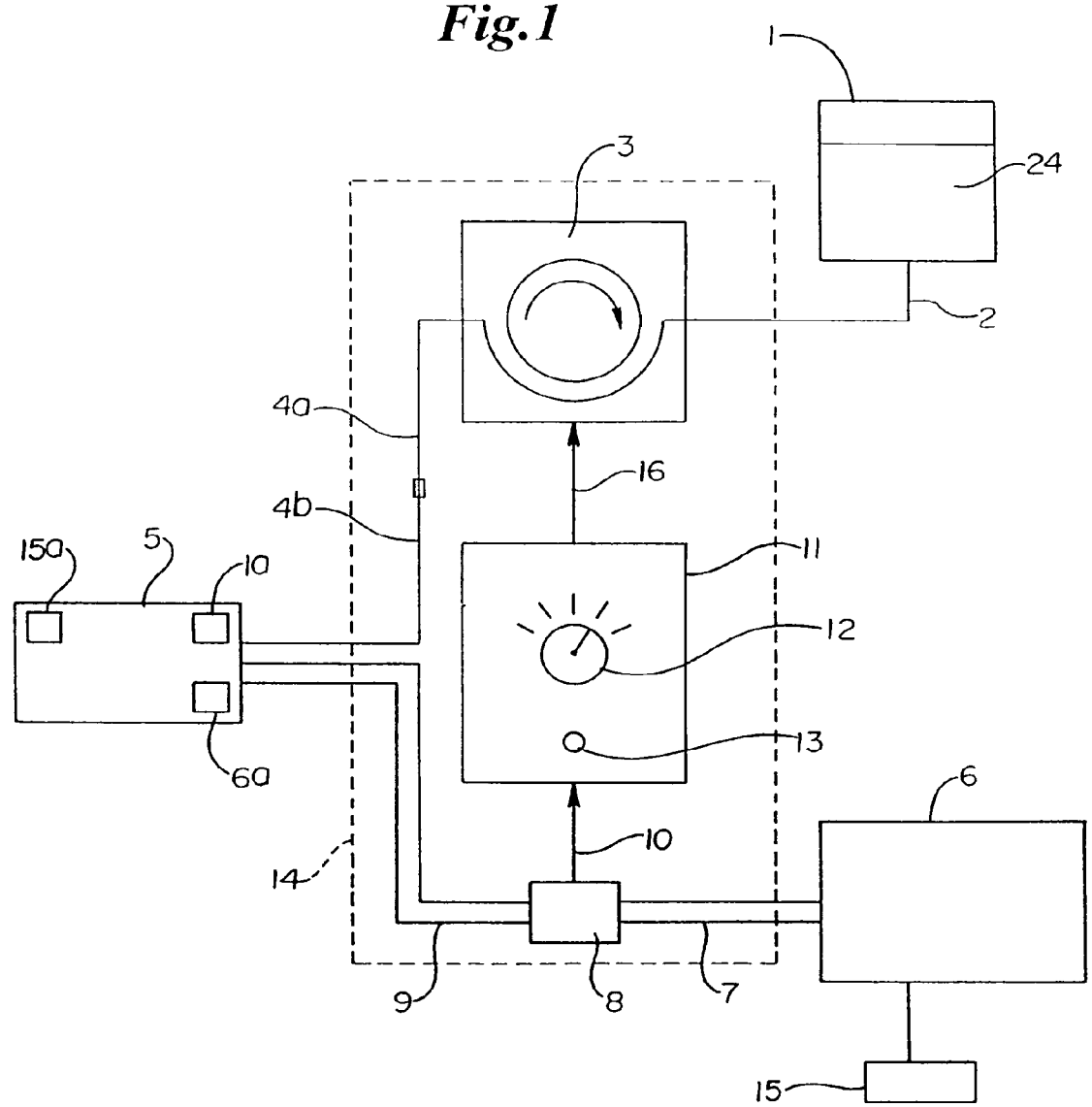
FIG. 1 is a block diagram showing one embodiment of a control system of the invention, and an electrosurgical device.

Throughout the present description, like reference numerals and letters indicate corresponding structure throughout the several views, and such corresponding structure need not be separately discussed. Furthermore, any particular feature(s) of a particular exemplary embodiment may be equally applied to any other exemplary embodiment(s) of this specification as suitable. In other words, features between the various exemplary embodiments described herein are interchangeable as suitable, and not exclusive.

The invention provides systems, devices and methods that preferably improve control of tissue temperature at a tissue treatment site during a medical procedure. The invention is particularly useful during surgical procedures upon tissues of the body, where it is desirable to shrink tissue, coagulate fluids (e.g. oozing blood), and at least partially occlude lumens, vessels (e.g. lumen of blood vessels (e.g. arteries, veins), intestines (e.g. absorbent vessels)) and airways (e.g. trachea, bronchi, bronchiole)).

The invention preferably involves the use of electrosurgical procedures, which preferably utilize RF power and electrically conductive fluid to treat tissue. Preferably, a desired tissue temperature range is achieved through adjusting parameters, such as conductive fluid flow rate, that affect the temperature at the tissue/electrode interface. Preferably, the device achieves a desired tissue temperature utilizing a desired percentage boiling of the conductive solution at the tissue/electrode interface.

In one embodiment, the invention provides a control device, the device comprising a flow rate controller that receives a signal indicating power applied to the system, and adjusts the flow rate of conductive fluid from a fluid source to an electrosurgical device. The invention also contemplates a control system comprising a flow rate controller, a measurement device that measures power applied to the system, and a pump that provides fluid at a selected flow rate.

The invention will be discussed generally with reference to FIG. 1. FIG. 1 shows a block diagram of one exemplary embodiment of a system of the invention. Preferably, as shown in FIG. 1, an electrically conductive fluid is provided from a fluid source 1, through a fluid line 2, to a pump 3, which has an outlet fluid line 4a that is connected as an input fluid line 4b to electrosurgical device 5. In a preferred embodiment, the outlet fluid line 4a and the input fluid line 4b are flexible and comprise a polymer, such as polyvinylchloride (PVC), while the conductive fluid comprises a saline solution. More preferably, the saline comprises sterile, and even more preferably, normal saline. Although the description herein will specifically describe the use of saline as the fluid, other electrically conductive fluids, as well as non-conductive fluids, can be used in accordance with the invention.

For example, in addition to the conductive fluid comprising physiologic saline (also known as "normal" saline, isotonic saline or 0.9% sodium chloride (NaCl) solution), the conductive fluid may comprise hypertonic saline solution, hypotonic saline solution, Ringers solution (a physiologic solution of distilled water containing specified amounts of sodium chloride, calcium chloride, and potassium chloride), lactated Ringer's solution (a crystalloid electrolyte sterile solution of distilled water containing specified amounts of calcium chloride, potassium chloride, sodium chloride, and sodium lactate), Locke-Ringer's solution (a buffered isotonic solution of distilled water containing specified amounts of sodium chloride, potassium chloride, calcium chloride, sodium bicarbonate, magnesium chloride, and dextrose), or any other electrolyte solution. In other words, a solution that conducts electricity via an electrolyte, a substance (salt, acid or base) that dissociates into electrically charged ions when dissolved in a solvent, such as water, resulting solution comprising an ionic conductor.

While a conductive fluid is preferred, as will become more apparent with further reading of this specification, the fluid may also comprise an electrically non-conductive fluid. The use of a non-conductive fluid is less preferred to that of a conductive fluid as the non-conductive fluid does not conduct electricity. However, the use of a non-conductive fluid still provides certain advantages over the use of a dry electrode including, for example, reduced occurrence of tissue sticking to the electrode. Therefore, it is also within the scope of the invention to include the use of a non-conducting fluid, such as, for example, dionized water.

Energy to heat tissue is provided from energy source, such as an electrical generator 6 which preferably provides RF alternating current energy via a cable 7 to energy source output measurement device, such as a power measurement device 8 that measures the RF alternating current electrical power. In one exemplary embodiment, preferably the power measurement device 8 does not turn the power off or on, or alter the power in any way. A power switch 15 connected to the generator 6 is preferably provided by the generator manufacturer and is used to turn the generator 6 on and off. The power switch 15 can comprise any switch to turn the power on and off, and is commonly provided in the form of a footswitch or other easily operated switch, such as a switch 15a mounted on the electrosurgical device 5. The power switch 15 or 15a may also function as a manually activated device for increasing or decreasing the rate of energy provided from the surgical device 5. Alternatively, internal circuitry and other components of the generator 6 may be used for automatically increasing or decreasing the rate of energy provided from the surgical device 5. A cable 9 preferably carries RF energy from the power measurement device 8 to the electrosurgical device 5. Power, or any other energy source output, is preferably measured before it reaches the electrosurgical device 5.

For the situation where capacitation and induction effects are negligibly small, from Ohm's law, power P, or the rate of energy delivery (e.g. joules/sec), may be expressed by the product of current times voltage (i.e. I×V), the current squared times resistance (i.e. $I^2 \times R$), or the voltage squared divided by the resistance (i.e. $V^2/R$); where the current I may be measured in amperes, the voltage V may be measured in volts, the electrical resistance R may be measured in ohms, and the power P may be measured in watts (joules/sec). Given that power P is a function of current I, voltage V, and resistance R as indicated above, it should be understood, that a change in power P is reflective of a change in at least one of the input variables. Thus, one may alternatively measure changes in such input variables themselves, rather than power P directly, with such changes in the input variables mathematically corresponding to a changes in power P as indicated above.

As to the frequency of the RF electrical energy, it is preferably provided within a frequency band (i.e. a continuous range of frequencies extending between two limiting frequencies) in the range between and including about 9 kHz (kilohertz) to 300 GHz (gigahertz). More preferably, the RF energy is provided within a frequency band in the range between and including about 50 kHz (kilohertz) to 50 MHz (megahertz). Even more preferably, the RF energy is provided within a frequency band in the range between and including about 200 kHz (kilohertz) to 2 MHz (megahertz). Most preferably, RF energy is provided within a frequency band in the range between and including about 400 kHz (kilohertz) to 600 kHz (kilohertz). Further, it should also be understood that, for any frequency band identified above, the range of frequencies may be further narrowed in increments of 1 (one) hertz anywhere between the lower and upper limiting frequencies.

While RF electrical energy is preferred, it should be understood that the electrical energy (i.e., energy made available by the flow of electric charge, typically through a conductor or by self-propagating waves) may comprise any frequency of the electromagnetic spectrum (i.e. the entire range of radiation extending in frequency from $10^{23}$ hertz to 0 hertz) and including, but not limited to, gamma rays, x-rays, ultraviolet radiation, visible light, infrared radiation, microwaves, and any combinations thereof.

With respect to the use of electrical energy, heating of the tissue is preferably performed by means of resistance heating. In other words, increasing the temperature of the tissue as a result of electric current flow through the tissue, with the electrical energy being absorbed from the voltage and transformed into thermal energy (i.e. heat) via accelerated movement of ions as a function of the tissue's electrical resistance.

Heating with electrical energy may also be performed by means of dielectric heating (capacitation). In other words, increasing the temperature of the tissue through the dissipation of electrical energy as a result of internal dielectric loss when the tissue is placed in a varying electric field, such as a high-frequency (e.g. microwave), alternating electromagnetic field. Dielectric loss is the electrical energy lost as heat in the polarization process in the presence of the applied electric field. In the case of an alternating current field, the energy is absorbed from the alternating current voltage and converted to heat during the polarization of the molecules.

However, it should be understood that energy provided to heat the tissue may comprise surgical devices other than electrosurgical devices, energy sources other than generators, energy forms other than electrical energy and mechanisms other than resistance heating. For example, providing thermal energy to the tissue from energy source with a difference (e.g. higher) in temperature. Such may be provided, for example, to the tissue from a heated device, which heats tissue through direct contact with the energy source (conduction), heats through contact with a flowing fluid (convection), or from a remote heat source (radiation).

Also, for example, providing energy to the tissue may be provided via mechanical energy which is transformed into thermal energy via accelerated movement of the molecules, such as by mechanical vibration provided, for example, by energy source such as a transducer containing a piezoelectric substance (e.g., a quartz-crystal oscillator) that converts high-frequency electric current into vibrating ultrasonic waves which may be used by, for example, an ultrasonic surgical device.

Also, for example, providing energy to the tissue may be provided via radiant energy (i.e. energy which is transmitted by radiation/waves) which is transformed into thermal energy via absorption of the radiant energy by the tissue. Preferably the radiation/waves comprise electromagnetic radiation/waves which include, but is not limited to, radio waves, microwaves, infrared radiation, visible light radiation, ultraviolet radiation, x-rays and gamma rays. More preferably, such radiant energy comprises energy with a frequency of $3 \times 10^{11}$ hertz to $3 \times 10^{16}$ hertz (i.e. the infrared, visible, and ultraviolet frequency bands of the electromagnetic spectrum). Also preferably the electromagnetic waves are coherent and the electromagnetic radiation is emitted from energy source such as a laser device. A flow rate controller 11 preferably includes a selection switch 12 that can be set to achieve desired levels of percentage fluid boiling (for example, 100%, 98%, 80% boiling). Preferably, the flow rate controller 11 receives an input signal 10 from the power measurement device 8 and calculates an appropriate mathematically predetermined fluid flow rate based on percentage boiling indicated by the selection switch 12. In a preferred embodiment, a fluid switch 13 is provided so that the fluid system can be primed (e.g. air eliminated) before turning the generator 6 on. The output signal 16 of the flow rate controller 11 is preferably sent to the pump 3 motor to regulate the flow rate of conductive fluid, and thereby provide an appropriate fluid flow rate which corresponds to the amount of power being delivered.

In one exemplary embodiment, the invention comprises a flow rate controller that is configured and arranged to be connected to a source of RF power, and a source of fluid, for example, a source of conductive fluid. The device of the invention receives information about the level of RF power applied to an electrosurgical device, and adjusts the flow rate of the fluid to the electrosurgical device, thereby controlling temperature at the tissue treatment site.

In another exemplary embodiment, elements of the system are physically included together in one electronic enclosure. One such embodiment is shown by enclosure within the outline box 14 of FIG. 1. In the illustrated embodiment, the pump 3, flow rate controller 11, and power measurement device 8 are enclosed within an enclosure, and these elements are connected through electrical connections to allow signal 10 to pass from the power measurement device 8 to the flow rate controller 11, and signal 16 to pass from the flow rate controller 11 to the pump 3. Other elements of a system can also be included within one enclosure, depending upon such factors as the desired application of the system, and the requirements of the user.

The pump 3 can be any suitable pump used in surgical procedures to provide saline or other fluid at a desired flow rate. Preferably, the pump 3 comprises a peristaltic pump. With a rotary peristaltic pump, typically a fluid is conveyed within the confines of a flexible tube by waves of contraction placed externally on the tube which are produced mechanically, typically by rotating rollers which squeeze the flexible tubing against a support intermittently. Alternatively, with a linear peristaltic pump, typically a fluid is conveyed within the confines of a flexible tube by waves of contraction placed externally on the tube which are produced mechanically, typically by a series of compression fingers or pads which squeeze the flexible tubing against a support sequentially. Peristaltic pumps are generally preferred for use as the electro-mechanical force mechanism (e.g. rollers driven by electric motor) does not make contact the fluid, thus reducing the likelihood of inadvertent contamination.

Alternatively, pump 3 can be a "syringe pump", with a built-in fluid supply. With such a pump, typically a filled syringe is located on an electro-mechanical force mechanism (e.g. ram driven by electric motor) which acts on the plunger of the syringe to force delivery of the fluid contained therein. Alternatively, the syringe pump may comprise a double-acting syringe pump with two syringes such that they can draw saline from a reservoir, either simultaneously or intermittently. With a double acting syringe pump, the pumping mechanism is generally capable of both infusion and withdrawal. Typically, while fluid is being expelled from one syringe, the other syringe is receiving fluid therein from a separate reservoir. In this manner, the delivery of fluid remains continuous and uninterrupted as the syringes function in series. Alternatively, it should be understood that a multiple syringe pump with two syringes, or any number of syringes, may be used in accordance with the invention.

Furthermore, fluid, such as conductive fluid, can also be provided from an intravenous (IV) bag full of saline that flows under the influence (i.e. force) of gravity. In such a manner, the fluid may flow directly to the electrosurgical device 5, or first to the pump 3 located there between. Alternatively, fluid from a fluid source such as an IV bag can be provided through an IV flow controller that may provide a desired flow rate by adjusting the cross sectional area of a flow orifice (e.g. lumen of the connective tubing with the electrosurgical device) while sensing the flow rate with a sensor such as an optical drop counter. Furthermore, fluid from a fluid source such as an IV bag an be provided through a manually or automatically activated device such as a flow controller, such as a roller clamp, which also adjusts the cross sectional area of a flow orifice and may be adjusted manually by, for example, the user of the device in response to their visual observation (e.g. fluid boiling) at the tissue treatment site or a pump.

Similar pumps can be used in connection with the invention, and the illustrated embodiments are exemplary only. The precise configuration of the pump 3 is not critical to the invention. For example, pump 3 may include other types of infusion and withdrawal pumps. Furthermore, pump 3 may comprise pumps which may be categorized as piston pumps, rotary vane pumps (e.g. blower, axial impeller, centrifugal impeller), cartridge pumps and diaphragm pumps. In some embodiments, the pump can be substituted with any type of flow controller, such as a manual roller clamp used in conjunction with an IV bag, or combined with the flow controller to allow the user to control the flow rate of conductive fluid to the device. Alternatively, a valve configuration can be substituted for pump 3.

Furthermore, similar configurations of the system can be used in connection with the invention, and the illustrated embodiments are exemplary only. For example, the fluid source 1 pump 3, generator 6, power measurement device 8 or flow rate controller 11, or any other components of the system not expressly recited above, may comprise a portion of the electrosurgical device 5. For example, in one exemplary embodiment the fluid source may comprise a compartment of the electrosurgical device 5 which contains fluid, as indicated at reference character 1a. In another exemplary embodiment, the compartment may be detachably connected to the electrosurgical device 5, such as a canister which may be attached via threaded engagement with the device 5. In yet another exemplary embodiment, the compartment may be configured to hold a pre-filled cartridge of fluid, rather than the fluid directly.

Also for example, with regards to the generator, energy source, such as a direct current (DC) battery used in conjunction with inverter circuitry and a transformer to produce alternating current at a particular frequency, may comprise a portion of the electrosurgical device 5, as indicated at reference character 6a. In one embodiment the battery element of the energy source may comprise a rechargeable battery. In yet another exemplary embodiment, the battery element may be detachably connected to the electrosurgical device 5, such as for recharging. The components of the system will now be described in further detail. From the specification, it should be clear that any use of the terms "distal" and "proximal" are made in reference from the user of the device, and not the patient.

Figure 2:
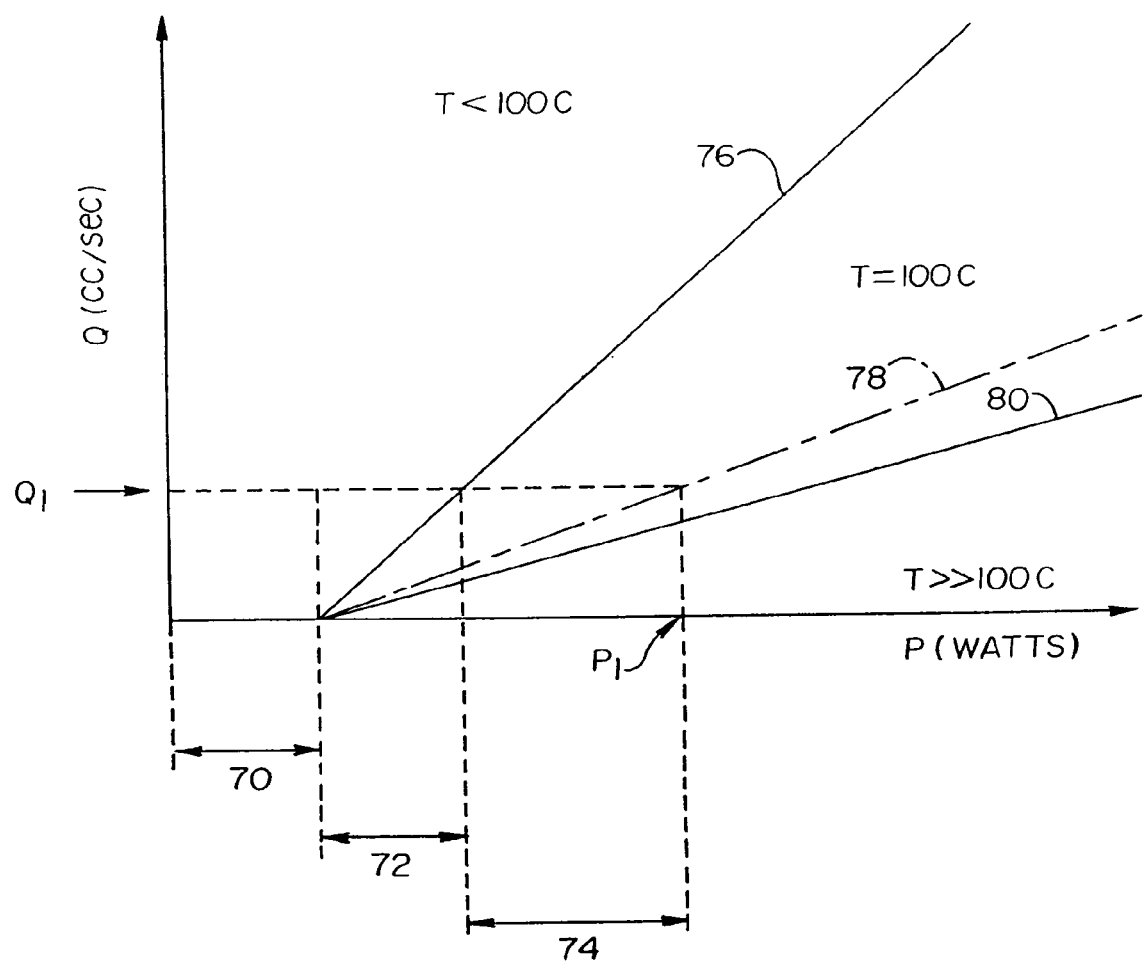
FIG. 2 is a schematic graph that describes the relationship between RF power to tissue (P), flow rate of saline (Q), and tissue temperature (T) when heat conduction to adjacent tissue is considered.

The flow rate controller 11 controls the rate of flow from the fluid source 1. Preferably, the rate of fluid flow from the fluid source 1 is based upon the amount of RF power provided from the generator 6 to the electrosurgical device 5. In other words, as shown in FIG. 2, preferably there is a relationship between the rate of fluid flow and the RF power as indicated by the X- and Y-axes of the schematic graph. More precisely, as shown in FIG. 2, the relationship between the rate of fluid flow and RF power may be expressed as a direct, linear relationship. The flow rate of conductive fluid, such as saline, interacts with the RF power and various modes of heat transfer away from the target tissue, as described herein.

Throughout this disclosure, when the terms "boiling point of saline", "vaporization point of saline", and variations thereof are used, what is intended is the boiling point of the water in the saline solution.

FIG. 2 shows a schematic graph that describes the relationship between the flow rate of saline, RF power to tissue, and regimes of boiling as detailed below. Based on a simple one-dimensional lumped parameter model of the heat transfer, the peak tissue temperature can be estimated, and once tissue temperature is estimated, it follows directly whether it is hot enough to boil saline.

$$P = \Delta T/R + \rho c_p Q_1 \Delta T + \rho Q_b h_v \quad (1)$$

where P=the total RF electrical power that is converted into heat.

Conduction. The first term $[\Delta T/R]$ in equation (1) is heat conducted to adjacent tissue, represented as 70 in FIG. 2, where:

$\Delta T = (T - T_\infty)$ the difference in temperature between the peak tissue temperature (T) and the normal temperature ($T_\infty$) of the body tissue (° C.). Normal temperature of the body tissue is generally 37° C.; and R=Thermal resistance of surrounding tissue, the ratio of the temperature difference to the heat flow (° C./watt).

This thermal resistance can be estimated from published data gathered in experiments on human tissue (Phipps, J. H., "Thermometry studies with bipolar diathermy during hysterectomy," *Gynaecological Endoscopy*, 3:5-7 (1994)). As described by Phipps, Kleppinger bipolar forceps were used with an RF power of 50 watts, and the peak tissue temperature reached 320° C. For example, using the energy balance of equation (1), and assuming all the RF heat put into tissue is conducted away, then R can be estimated:

$$R = \Delta T/P = (320-37)/50 = 5.7 \approx 6° \text{ C./watt}$$

However, it is undesirable to allow the tissue temperature to reach 320° C., since tissue will become desiccated. At a temperature of 320° C., the fluid contained in the tissue is typically boiled away, resulting in the undesirable tissue effects described herein. Rather, it is preferred to keep the peak tissue temperature at no more than about 100° C. to inhibit desiccation of the tissue. Assuming that saline boils at about 100° C., the first term in equation (1) ($\Delta T/R$) is equal to (100-37)/6=10.5 watts. Thus, based on this example, the maximum amount of heat conducted to adjacent tissue without any significant risk of tissue desiccation is 10.5 watts.

Referring to FIG. 2, RF power to tissue is represented on the X-axis as P (watts) and flow rate of saline (cc/min) is represented on the Y-axis as Q. When the flow rate of saline equals zero (Q=0), there is an "offset" RF power that shifts the origin of the sloped lines 76, 78, and 80 to the right. This offset is the heat conducted to adjacent tissue. For example, using the calculation above for bipolar forceps, this offset RF power is about 10.5 watts. If the power is increased above this level with no saline flow, the peak tissue temperature can rise well above 100° C., resulting in tissue desiccation from the boiling off of water in the cells of the tissue.

Convection. The second term $[\rho c_p Q_1 \Delta T]$ in equation (1) is heat used to warm up the flow of saline without boiling the saline, represented as 72 in FIG. 2, where:

$\rho$=Density of the saline fluid that gets hot but does not boil (approximately 1.0 gm/cm³);

$c_p$=Specific heat of the saline (approximately 4.1 watt-sec/gm-° C.);

$Q_1$=Flow rate of the saline that is heated (cm³/sec); and $\Delta T$=Temperature rise of the saline. Assuming that the saline is heated to body temperature before it gets to the electrode, and that the peak saline temperature is similar to the peak tissue temperature, this is the same $\Delta T$ as for the conduction calculation above.

The onset of boiling can be predicted using equation (1) with the last term on the right set to zero (no boiling) ($\rho Q_b h_v = 0$), and solving equation (1) for $Q_1$ leads to:

$$Q_1 = [P - \Delta T/R]/\rho c_p \Delta T \quad (2)$$

This equation defines the line shown in FIG. 2 as the line of onset of boiling 76.

Boiling. The third term $[\rho Q_b h_v]$ in equation (1) relates to heat that goes into converting the water in liquid saline to water vapor, and is represented as 74 in FIG. 2, where:

$Q_b$=Flow rate of saline that boils (cm³/sec); and $h_v$=Heat of vaporization of saline (approximately 2,000 watt-sec/gm).

A flow rate of only 1 cc/min will absorb a significant amount of heat if it is completely boiled, or about $\rho Q_b h_v = (1)(1/60)(2,000) = 33.3$ watts. The heat needed to warm this flow rate from body temperature to 100° C. is much less, or $\rho c_p Q_1 \Delta T = (1)(4.1)(1/60)(100-37) = 4.3$ watts. In other words, the most significant factor contributing to heat transfer from a wet electrode device can be fractional boiling. The present invention recognizes this fact and exploits it.

Fractional boiling can be described by equation (3) below:

$$Q_1 = \frac{\{P - \Delta T/R\}}{\{\rho c_p \Delta T + \rho h_v Q_b/Q_l\}} \quad (3)$$

If the ratio of $Q_b/Q_1$ is 0.50 this is the 50% boiling line 78 shown in FIG. 2. If the ratio is 1.0 this is the 100% boiling line 80 shown in FIG. 2.

As indicated previously in the specification, using a fluid to couple energy to tissue inhibits such undesirable effects as sticking, desiccation, smoke production and char formation, and that one key factor is inhibiting tissue desiccation, which occur if the tissue temperature exceeds 100° C. and all the intracellular water boils away, leaving the tissue extremely dry and much less electrically conductive.

As shown in FIG. 2, one control strategy or mechanism which can be employed for the electrosurgical device 5 is to adjust the power P and flow rate Q such that the power P used at a corresponding flow rate Q is equal to or less than the power P required to boil 100% of the fluid and does not exceed the power P required to boil 100% of the fluid. In other words, this control strategy targets using the electrosurgical device 5 in the regions of FIG. 2 identified as T<100° C. and T=100° C., and includes the 100% boiling line 80. Stated another way, this control strategy targets not using the electrosurgical device 5 only in the region of FIG. 2 identified as T>>100° C.

Another control strategy that can be used for the electrosurgical device 5 is to operate the device 5 in the region T<100° C., but at high enough temperature to shrink tissue containing Type I collagen (e.g., walls of blood vessels, bronchi, bile ducts, etc.), which shrinks when exposed to about 85° C. for an exposure time of 0.01 seconds, or when exposed to about 65° C. for an exposure time of 15 minutes. An exemplary target temperature/time for tissue shrinkage is about 75° C. with an exposure time of about 1 second. As discussed herein, a determination of the high end of the scale (i.e., when the fluid reaches 100° C.) can be made by the phase change in the fluid from liquid to vapor. However, a determination at the low end of the scale (e.g., when the fluid reaches, for example, 75° C. for 1 second) requires a different mechanism as the temperature of the fluid is below the boiling temperature and no such phase change is apparent. In order to determine when the fluid reaches a temperature that will facilitate tissue shrinkage, for example 75° C., a thermochromic material, such as a thermochromic dye (e.g., leuco dye), may be added to the fluid. The dye can be formulated to provide a first predetermined color to the fluid at temperatures below a threshold temperature, such as 75° C., then, upon heating above 75° C., the dye provides a second color, such as clear, thus turning the fluid clear (i.e. no color or reduction in color). This color change may be gradual, incremental, or instant. Thus, a change in the color of the fluid, from a first color to a second color (or lack thereof) provides a visual indication to the user of the electrosurgical device 5 as to when a threshold fluid temperature below boiling has been achieved. Thermochromic dyes are available, for example, from Color Change Corporation, 1740 Cortland Court, Unit A, Addison, Ill. 60101.

It is also noted that the above mechanism (i.e., a change in the color of the fluid due to a dye) may also be used to detect when the fluid reaches a temperature which will facilitate tissue necrosis; this generally varies from about 60° C. for an exposure time of 0.01 seconds and decreasing to about 45° C. for an exposure time of 15 minutes. An exemplary target temperature/time for tissue necrosis is about 55° C. for an exposure time of about 1 second.

In order to reduce coagulation time, use of the electrosurgical device 5 in the region T=100° C. of FIG. 2 is preferable to use of the electrosurgical device 5 in the region T<100° C. Consequently, as shown in FIG. 2, another control strategy which may be employed for the electrosurgical device 5 is to adjust the power P and flow rate Q such that the power P used at a corresponding flow rate Q is equal to or more than the power P required to initiate boiling of the fluid, but still less than the power P required to boil 100% of the fluid. In other words, this control strategy targets using the electrosurgical device 5 in the region of FIG. 2 identified as T=100° C., and includes the lines of the onset of boiling 76 and 100% boiling line 80. Stated another way, this control strategy targets use using the electrosurgical device 5 on or between the lines of the onset of boiling 76 and 100% boiling line 80, and not using the electrosurgical device 5 in the regions of FIG. 2 identified as T<100° C. and T>>100° C.

For consistent tissue effect, it is desirable to control the saline flow rate so that it is always on a "line of constant % boiling" as, for example, the line of the onset of boiling 76 or the 100% boiling line 80 or any line of constant % boiling located in between (e.g. 50% boiling line 78) as shown in FIG. 2. Consequently, another control strategy that can be used for the electrosurgical device 5 is to adjust power P and flow rate Q such that the power P used at a corresponding flow rate Q targets a line of constant % boiling.

It should be noted, from the preceding equations, that the slope of any line of constant % boiling is known. For example, for the line of the onset of boiling 76, the slope of the line is given by $(\rho c_p \Delta T)$, while the slope of the 100% boiling line 80 is given by $1/(\rho c_p \Delta T + \rho h_v)$. As for the 50% boiling line 78, for example, the slope is given by $1/(\rho c_p \Delta T + \rho h_v 0.5)$.

If, upon application of the electrosurgical device 5 to the tissue, boiling of the fluid is not detected, such indicates that the temperature is less than 100° C. as indicated in the area of FIG. 2, and the flow rate Q must be decreased to initiate boiling. The flow rate Q may then decreased until boiling of the fluid is first detected, at which time the line of the onset of boiling 76 is transgressed and the point of transgression on the line 76 is determined. From the determination of a point on the line of the onset of boiling 76 for a particular power P and flow rate Q, and the known slope of the line 76 as outlined above (i.e. $1/\rho c_p \Delta T$), it is also possible to determine the heat conducted to adjacent tissue 70.

Conversely, if upon application of the electrosurgical device 5 to the tissue, boiling of the fluid is detected, such indicates that the temperature is approximately equal to 100° C. as indicated in the areas of FIG. 2, and the flow rate Q must be increased to reduce boiling until boiling stops, at which time the line of the onset of boiling 76 is transgressed and the point of transgression on the line 76 determined. As with above, from the determination of a point on the line of the onset of boiling 76 for a particular power P and flow rate Q, and the known slope of the line 76, it is also possible to determine the heat conducted to adjacent tissue 70.

With regards to the detection of boiling of the fluid, such may be physically detected by the user (e.g. visually by the naked eye) of the electrosurgical device 5 in the form of either bubbles or steam evolving from the fluid coupling at the electrode/tissue interface. Alternatively, such a phase change (i.e. from liquid to vapor or vice-versa) may be measured by a sensor which preferably senses either an absolute change (e.g. existence or non-existence of boiling with binary response such as yes or no) or a change in a physical quantity or intensity and converts the change into a useful input signal for an information-gathering system. For example, the phase change associated with the onset of boiling may be detected by a pressure sensor, such as a pressure transducer, located on the electrosurgical device 5. Alternatively, the phase change associated with the onset of boiling may be detected by a temperature sensor, such as a thermistor or thermocouple, located on the electrosurgical device 5, such as adjacent to the electrode. Also alternatively, the phase change associated with the onset of boiling may be detected by a change in the electric properties of the fluid itself. For example, a change in the electrical resistance of the fluid may be detected by an ohm meter; a change in the amperage may be measured by an amp meter; as change in the voltage may be detected by a volt meter; and a change in the power may be determined by a power meter.

Figure 3:
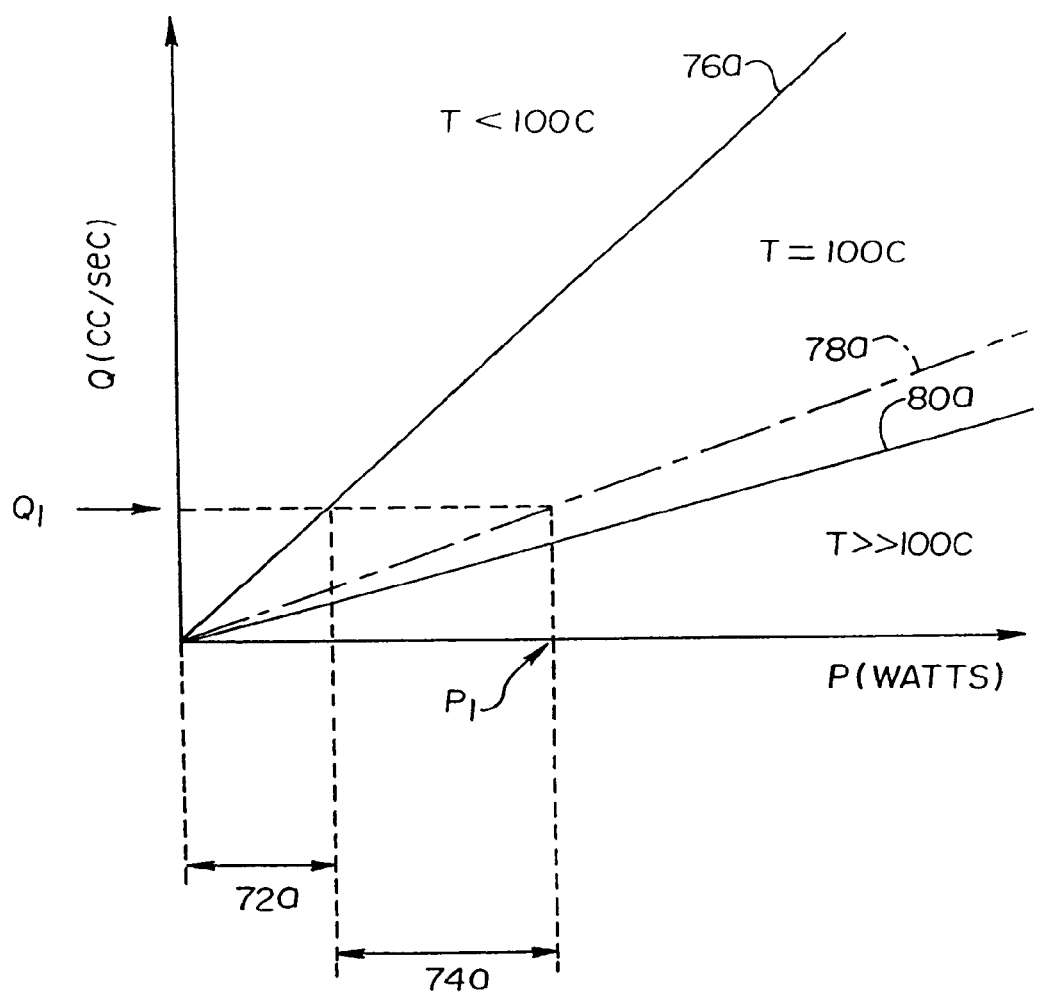
FIG. 3 is schematic graph that describes the relationship between RF power to tissue (P), flow rate of saline (Q), and tissue temperature (T) when heat conduction to adjacent tissue is neglected.

Yet another control strategy which may be employed for the electrosurgical device 5 is to eliminate the heat conduction term of equation (1) (i.e. $\Delta T/R$). Since the amount of heat conducted away to adjacent tissue can be difficult to precisely predict, as it may vary, for example, by tissue type, it may be preferable, from a control point of view, to assume the worst case situation of zero heat conduction, and provide enough saline so that if necessary, all the RF power could be used to heat up and boil the saline, thus providing that the peak tissue temperature will not go over 100° C. a significant amount. This situation is shown in the schematic graph of FIG. 3.

Stated another way, if the heat conducted to adjacent tissue 70 is overestimated, the power P required to intersect the 100% boiling line 80 will, in turn, be overestimated and the 100% boiling line 80 will be transgressed into the T>>100° C. region of FIG. 2, which is undesirable as established above. Thus, assuming the worse case situation of zero heat conduction provides a "safety factor" to avoid transgressing the 100% boiling line 80. Assuming heat conduction to adjacent tissue 70 to be zero also provides the advantage of eliminating the only term from equation (1) which is tissue dependent, i.e., depends on tissue type. Thus, provided $\rho$, $c_p$, $\Delta T$, and $h_v$ are known as indicated above, the equation of the line for any line of constant % boiling is known. Thus, for example, the 98% boiling line, 80% boiling line, etc. can be determined in response to a corresponding input from the selection switch 12. In order to promote flexibility, it should be understood that the input from the selection switch preferably may comprise any percentage of boiling. Preferably the percentage of boiling may be selected in single percent increments (i.e. 100%, 99%, 98%, etc.).

Upon determination of the line of the onset of boiling 76, the 100% boiling line 80 or any line of constant % boiling there between, it is generally desirable to control the flow rate Q so that it is always on a particular line of constant % boiling for consistent tissue effect. In such a situation, the flow rate controller 11 will adjust the flow rate Q of the fluid to reflect changes in power P provided by the generator 6, as discussed in greater detail below. For such a use the flow rate controller may be set in a line of constant boiling mode, upon which the % boiling is then correspondingly selected.

As indicated above, it is desirable to control the saline flow rate Q so that it is always on a line of constant % boiling for consistent tissue effect. However, the preferred line of constant % boiling may vary based on the type of electrosurgical device 5. For example, if the device is a monopolar stasis device and shunting through saline is not an issue, then it can be preferable to operate close to or directly on, but not over the line of the onset of boiling, such as 76a in FIG. 3. This preferably keeps tissue as hot as possible without causing desiccation. Alternatively, if the device has coaptive bipolar opposing jaws and shunting of electrical energy from one jaw to the other jaw through excess saline is an issue, then it can be preferable to operate along a line of constant boiling, such as line 78a in FIG. 3, the 50% line. This simple proportional control will have the flow rate determined by equation (4), where K is the proportionality constant:

$$Q_1 = K \times P \qquad (4)$$

In essence, when power P goes up, the flow rate Q will be proportionately increased. Conversely, when power P goes down, the flow rate Q will be proportionately decreased.

The proportionality constant K is primarily dependent on the fraction of saline that boils, as shown in equation (5), which is equation (3) solved for K after eliminating P using equation (4), and neglecting the conduction term ($\Delta T/R$):

$$K = \frac{1}{\{\rho c_p \Delta T + \rho h_v Q_b / Q_l\}} \qquad (5)$$

Thus, the present invention provides a method of controlling boiling of fluid, such as a conductive fluid, at the tissue/electrode interface. In a preferred embodiment, this provides a method of treating tissue without use of tissue sensors, such as temperature or impedance sensors. Preferably, the invention can control boiling of conductive fluid at the tissue/electrode interface and thereby control tissue temperature without the use of feedback loops.

In describing the control strategy of the present invention described thus far, focus has been drawn to a steady state condition. However, the heat required to warm the tissue to the peak temperature (T) may be incorporated into equation (1) as follows:

$$P = \Delta T/R + \rho c_p Q_1 \Delta T + \rho Q_b h_v + \rho c_p V \Delta T/\Delta t \qquad (6)$$

where $\rho c_p V \Delta T/\Delta t$ represents the heat required to warm the tissue to the peak temperature (T) 68 and where:
  $\rho$=Density of the saline fluid that gets hot but does not boil (approximately 1.0 gm/cm$^3$);
  $c_p$=Specific heat of the saline (approximately 4.1 watt-sec/gm-° C.);
  V=Volume of treated tissue
  $\Delta T = (T - T_\infty)$ the difference in temperature between the peak tissue temperature (T) and the normal temperature ($T_\infty$) of the body tissue (° C.). Normal temperature of the body tissue is generally 37° C.; and
  $\Delta t = (t - t_\infty)$ the difference in time to achieve peak tissue temperature (T) and the normal temperature ($T_\infty$) of the body tissue (° C.).

Figure 2A:
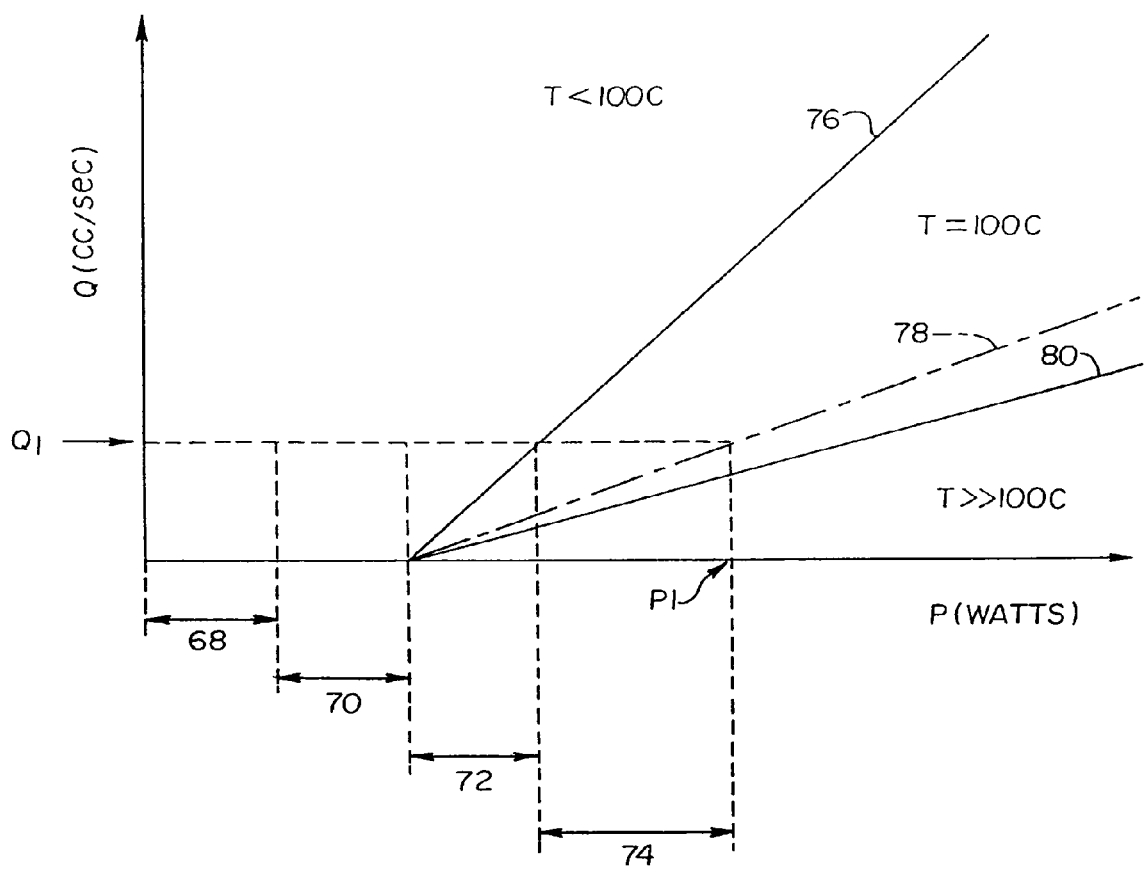
FIG. 2A is a schematic graph that describes the relationship between RF power to tissue (P), flow rate of saline (Q), and tissue temperature (T) when the heat required to warm the tissue to the peak temperature (T) 68 is considered.

The inclusion of the heat required to warm the tissue to the peak temperature (T) in the control strategy is graphically represented at 68 in FIG. 2A. With respect to the control strategy, the effects of the heat required to warm the tissue to the peak temperature (T) 68 should be taken into account before flow rate Q adjustment being undertaken to detect the location of the line of onset of boiling 76. In other words, the flow rate Q should not be decreased in response to a lack of boiling before at least a quasi-steady state has been achieved as the location of the line of onset of boiling 76 will continue to move during the transitory period. Otherwise, if the flow rate Q is decreased during the transitory period, it may be possible to decrease the flow Q to a point past the line of onset of boiling 76 and continue past the 100% boiling line 80 which is undesirable. In other words, as temperature (T) is approached the heat 68 diminishes towards zero such that the lines of constant boiling shift to the left towards the Y-axis.

Figure 4:
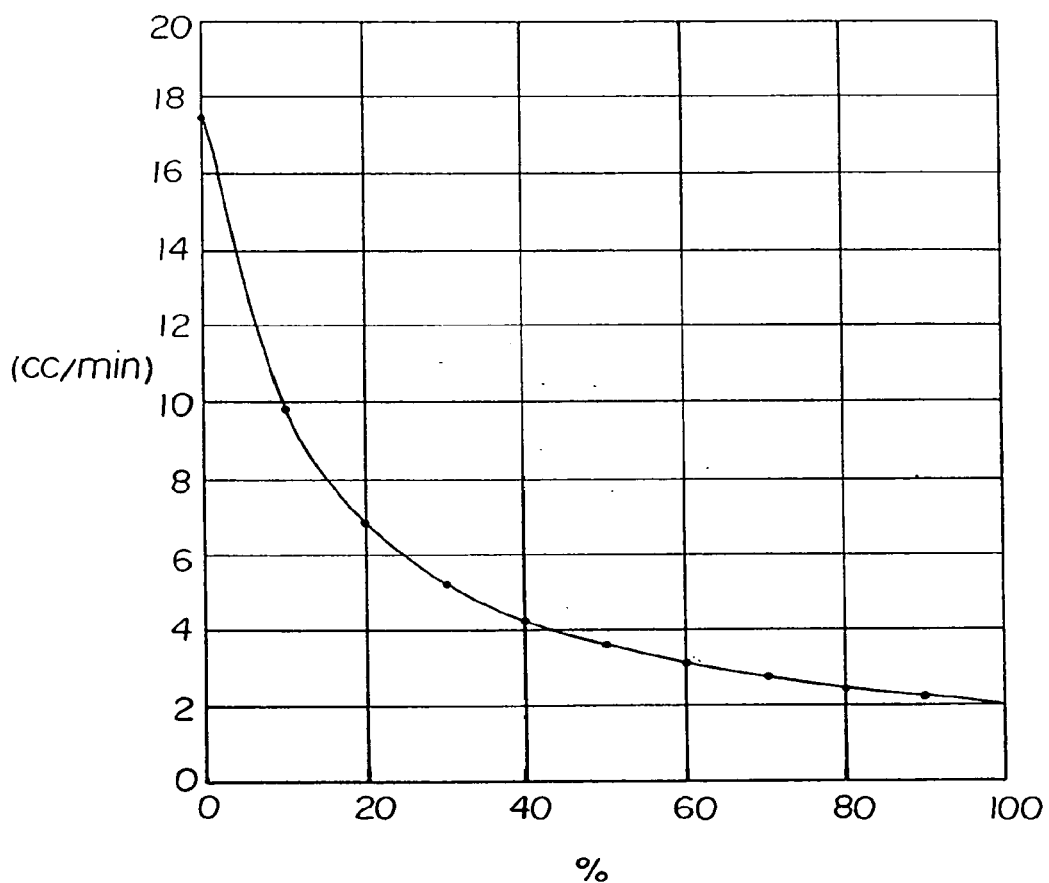
FIG. 4 is a graph showing the relationship of percentage saline boiling and saline flow rate (cc/min) for an exemplary RF generator output of 75 watts.

FIG. 4 shows an exemplary graph of flow rate Q versus % boiling for a situation where the RF power P is 75 watts. The percent boiling is represented on the X-axis, and the saline flow rate Q (cc/min) is represented on the Y-axis. According to this example, at 100% boiling the most desirable predetermined saline flow rate Q is 2 cc/min. Also according to this example, flow rate Q versus % boiling at the remaining points of the graft illustrates a non-linear relationship as follows:

TABLE 1

| % Boiling and Flow Rate Q (cc/min) at RF Power P of 75 watts | |
|---|---|
| 0% | 17.4 |
| 10% | 9.8 |

TABLE 1-continued

| % Boiling and Flow Rate Q (cc/min) at RF Power P of 75 watts | |
| --- | --- |
| 20% | 6.8 |
| 30% | 5.2 |
| 40% | 4.3 |
| 50% | 3.6 |
| 60% | 3.1 |
| 70% | 2.7 |
| 80% | 2.4 |
| 90% | 2.2 |
| 100% | 2.0 |

Typical RF generators used in the field have a power selector switch to 300 watts of power, and on occasion some have been found to be selectable up to 400 watts of power. In conformance with the above methodology, at 0% boiling with a corresponding power of 300 watts, the calculated flow rate Q is 69.7 cc/min and with a corresponding power of 400 watts the calculated flow rate Q is 92.9 cc/min. Thus, when used with typical RF generators in the field, a fluid flow rate Q of about 100 cc/min or less with the present invention is expected to suffice for the vast majority of applications.

Figure 5:
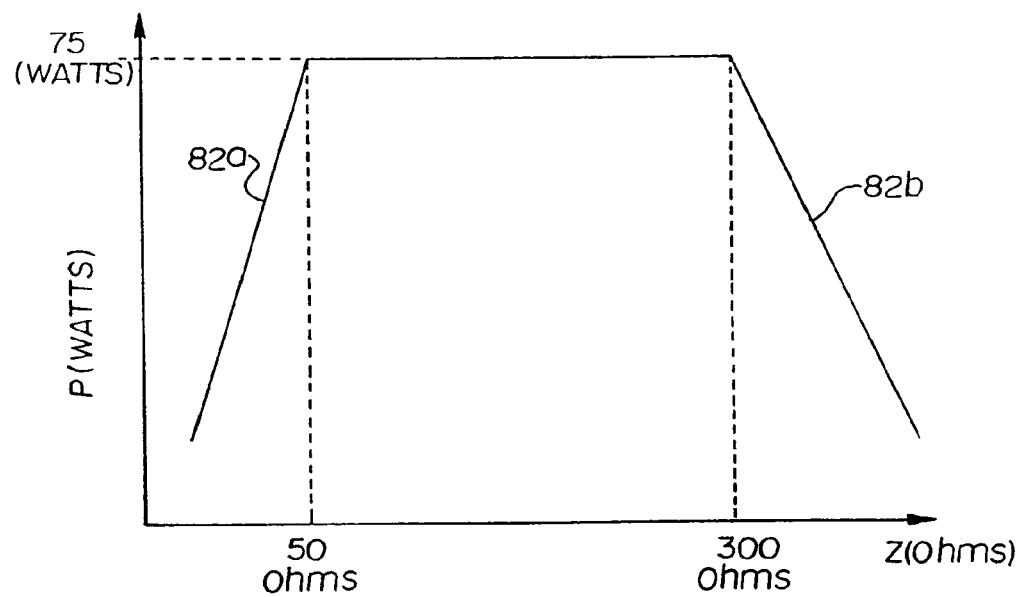
FIG. 5 is a schematic graph that describes the relationship of load impedance (Z, in ohms) and generator output power (P, in watts), for an exemplary generator output of 75 watts in a bipolar mode.

As discussed herein, RF energy delivery to tissue can be unpredictable and vary with time, even though the generator has been "set" to a fixed wattage. The schematic graph of FIG. 5 shows the general trends of the output curve of a typical general-purpose generator, with the output power changing as load (tissue plus cables) impedance Z changes. Load impedance Z (in ohms) is represented on the X-axis, and generator output power P (in watts) is represented on the Y-axis. In the illustrated embodiment, the electrosurgical power (RF) is set to 75 watts in a bipolar mode. As shown in the figure, the power will remain constant as it was set as long as the impedance Z stays between two cut-offs, low and high, of impedance, that is, for example, between 50 ohms and 300 ohms in the illustrated embodiment. Below load impedance Z of 50 ohms, the power P will decrease, as shown by the low impedance ramp 82a. Above load impedance Z of 300 ohms, the power P will decrease, as shown by the high impedance ramp 82b. Of particular interest to saline-enhanced electrosurgery is the low impedance cut-off (low impedance ramp 82a), where power starts to ramp down as impedance Z drops further. This change in output is invisible to the user of the generator and not evident when the generator is in use, such as in an operating room.

Figure 6:
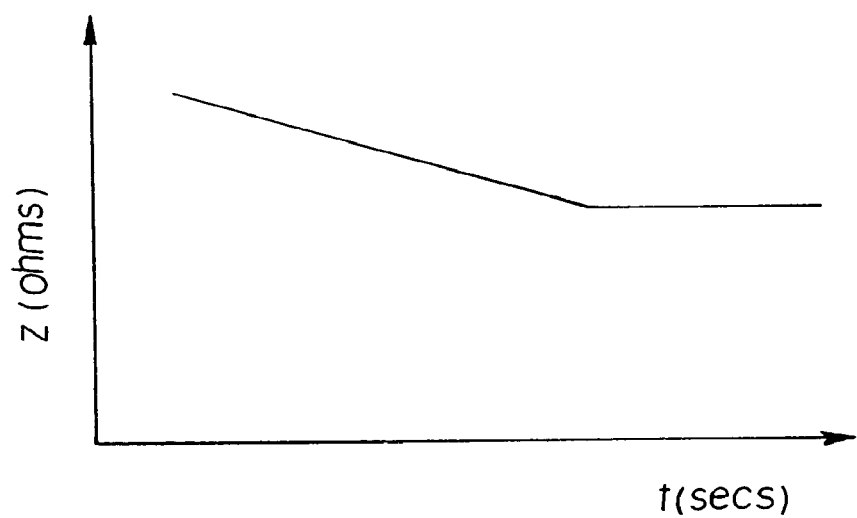
FIG. 6 is a schematic graph that describes the relationship of time (t, in seconds) and tissue impedance (Z, in ohms) after RF activation.

FIG. 6 shows the general trend of how tissue impedance generally changes with time for saline-enhanced electrosurgery. As tissue heats up, the temperature coefficient of the tissue and saline in the cells is such that the tissue impedance decreases until a steady-state temperature is reached upon which time the impedance remains constant. Thus, as tissue heats up, the load impedance Z decreases, potentially approaching the impedance Z cut-off of 50 ohms. If tissue is sufficiently heated, such that the low impedance cut-off is passed, the power P decreases along the lines of the low impedance ramp 82a of FIG. 5.

Combining the effects shown in FIG. 5 and FIG. 6, it becomes clear that when using a general-purpose generator set to a "fixed" power, the actual power delivered can change dramatically over time as tissue heats up and impedance drops. Looking at FIG. 5, if the impedance Z drops from 100 to 75 ohms over time, the power output would not change because the curve is "flat" in that region of impedances. If, however, the impedance Z drops from 75 to 30 ohms one would transgress the low impedance cut-off and "turn the corner" onto the low impedance ramp 82a portion of the curve and the power output would decrease dramatically.

According to one exemplary embodiment of the invention, the control device, such as flow rate controller 11, receives a signal indicating the drop in actual power delivered to the tissue and adjusts the flow rate Q of saline to maintain the tissue/electrode interface at a desired temperature. In a preferred embodiment, the drop in actual power P delivered is sensed by the power measurement device 8 (shown in FIG. 1), and the flow rate Q of saline is decreased by the flow rate controller 11 (also shown in FIG. 1). Preferably, this reduction in saline flow rate Q allows the tissue temperature to stay as hot as possible without desiccation. If the control device was not in operation and the flow rate Q allowed to remain higher, the tissue would be over-cooled at the lower power input. This would result in decreasing the temperature of the tissue at the treatment site.

The flow rate controller 11 of FIG. 1 can be a simple "hard-wired" analog or digital device that requires no programming by the user or the manufacturer. The flow rate controller 11 can alternatively include a processor, with or without a storage medium, in which the determination procedure is performed by software, hardware, or a combination thereof. In another embodiment, the flow rate controller 11 can include semi-programmable hardware configured, for example, using a hardware descriptive language, such as Verilog. In another embodiment, the flow rate controller 11 of FIG. 1 is a computer, microprocessor-driven controller with software embedded. In yet another embodiment, the flow rate controller 11 can include additional features, such as a delay mechanism, such as a timer, to automatically keep the saline flow on for several seconds after the RF is turned off to provide a post-coagulation cooling of the tissue or "quench," which can increase the strength of the tissue seal. Also, in another embodiment, the flow rate controller 11 can include a delay mechanism, such as a timer, to automatically turn on the saline flow several seconds before the RF is turned on to inhibit the possibility of undesirable effects as sticking, desiccation, smoke production and char formation. Also in another embodiment, the flow rate controller 11 can include a low level flow standby mechanism, such as a valve, which continues the saline flow at a standby flow level (which prevents the flow rate from going to zero when the RF power is turned off) below the surgical flow level ordinarily encountered during use of the electrosurgical device 5.

Figure 7:
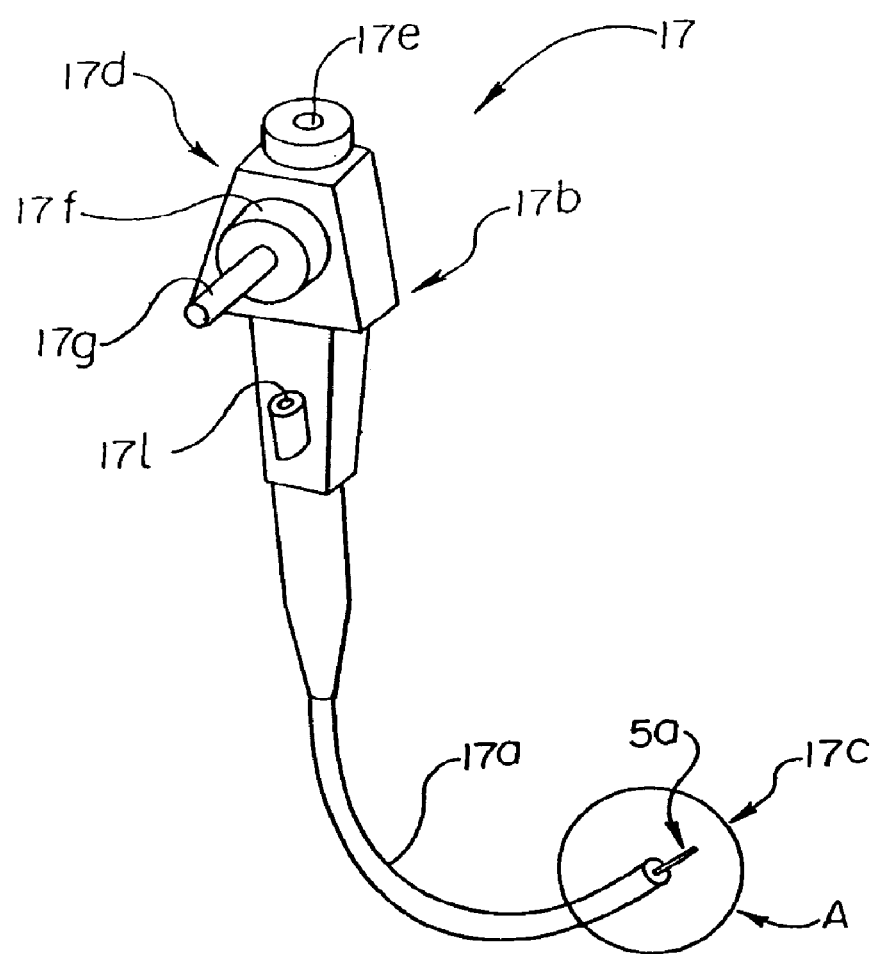
FIG. 7 is a schematic perspective view of a viewing scope with an electrosurgical device according to one embodiment of the invention.
Figure 8:
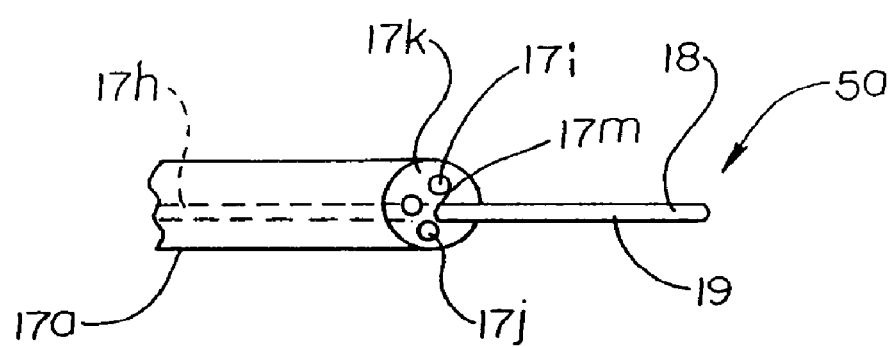
FIG. 8 is a schematic close-up view of the distal end portion of the viewing scope of FIG. 7 bounded by circle A with an electrosurgical device according to one embodiment of the invention.
Figure 9:
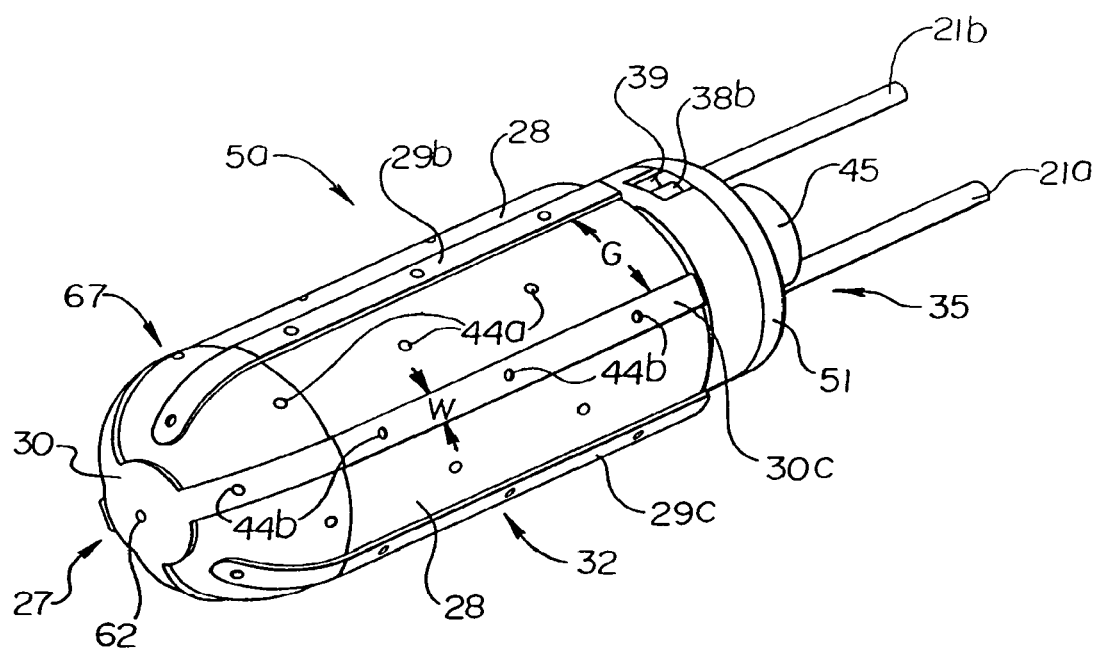
FIG. 9 is a schematic close-up front perspective view of an electrosurgical device according to one embodiment of the invention.

An exemplary electrosurgical device of the present invention which may be used in conjunction with the system of the present invention is shown at reference character 5a in FIG. 9, and more particularly in FIGS. 7-16. While various electrosurgical devices of the present invention are described with reference to use with the remainder of the system of the invention, it should be understood that the description of the combination is for purposes of illustrating the remainder of the system of the invention only. Consequently, it should be understood that the electrosurgical devices of the present invention can be used alone, or in conjunction with the remainder of the system of the invention, or that a wide variety of electrosurgical devices can be used in connection with the remainder of the system of the invention.

As shown in FIGS. 7 and 8, electrosurgical device 5a is preferably used in conjunction with a viewing scope, shown as an endoscope as illustrated at reference character 17, during a minimally invasive procedure such flexible endoscopic gastro-intestinal surgery. The endoscope 17 preferably comprises an elongated flexible shaft portion 17a, though device 5a may be used with rigid shaft viewing scopes, for example, during laparoscopic surgery.

Endoscope 17 also comprises a proximal portion 17b separated from a distal portion 17c by shaft portion 17a. Proximal portion 17b of endoscope 17 preferably comprises a control head portion 17d. Control head portion 17d preferably comprises a tissue treatment site viewer 17e and one or more directional control knobs 17f and 17g to control the movement of the flexible distal portion 17c of flexible shaft 17a. Control knob 17f preferably comprises a right/left angulation control knob while control knob 17g preferably comprises an up/down angulation control knob.

As shown in FIG. 8, flexible shaft 17a houses at least one device channel 17h through which surgical device 5a may be passed. Also as shown, flexible shaft 17a also preferably contains at least one viewing channel 17i to enable viewing through the distal portion 17c. Flexible shaft 17a also preferably contains at least one fluid flow channel 17j for providing liquid (e.g. water) or gas (e.g. air) to a tissue treatment site. Also preferably, electrosurgical device 5a is configured to extend from the distal end portion 17c, and more preferably, the distal end surface 17k of endoscope 17, as shown in FIG. 8.

Figure 11:
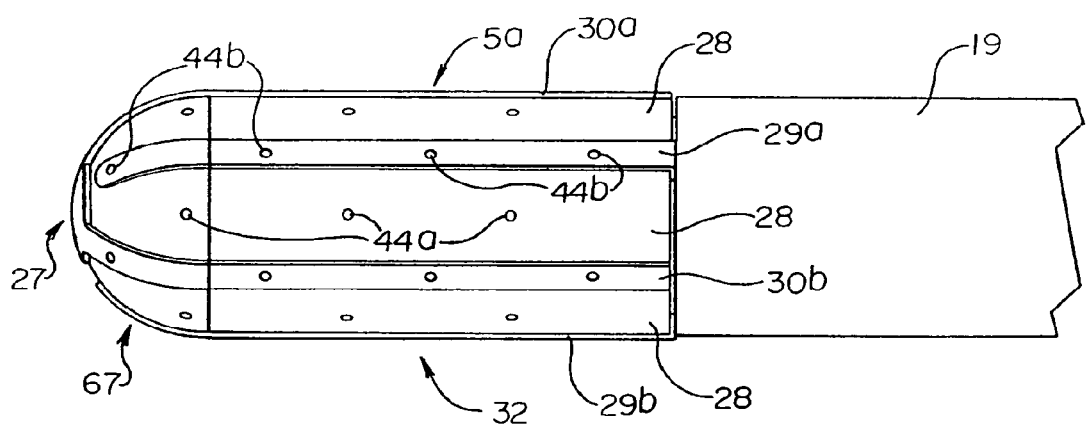
FIG. 11 is a schematic close-up side view of the electrosurgical device of FIG. 9 as part of a medical device assembly.
Figure 12:
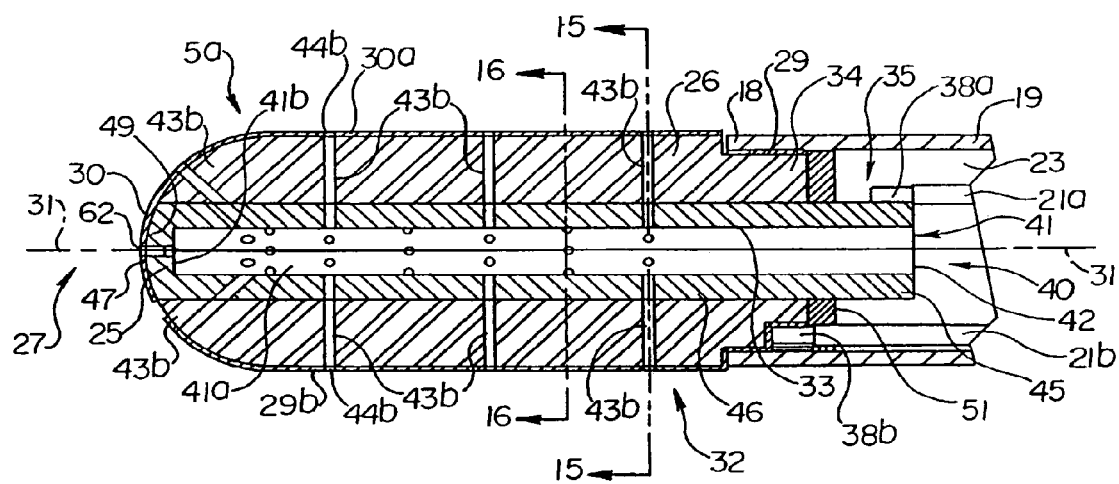
FIG. 12 is a schematic close-up cross-sectional view of the assembly of FIG. 11 taken in accordance with line 12-12 of FIG. 13.
Figure 13:
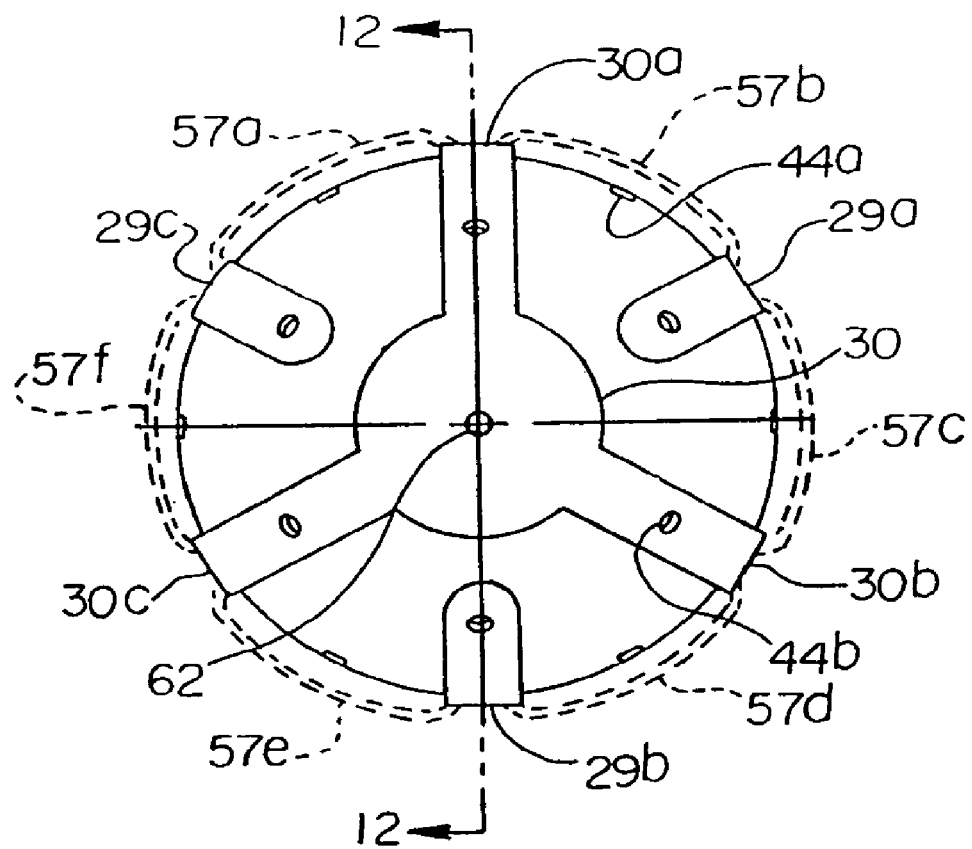
FIG. 13 is a schematic close-up front view of the electrosurgical device of FIG. 9.

As shown in FIGS. 11 and 12, electrosurgical device 5a is preferably assembled (e.g. mechanically connected via press-fit, mechanical connector, welded, adhesively bonded) adjacent the distal end 18 of a long, hollow, tube 19 to preferably form a medical device assembly. Tube 19 is preferably self-supporting and flexible, and more preferably comprises a catheter which may be flexed to apply tamponade (e.g. compressive force) through the electrosurgical device 5a to a bleeding source in the gastrointestinal tract. Electrosurgical device 5a, in combination with a catheter, may be referred to as a catheter assembly.

Figure 10:
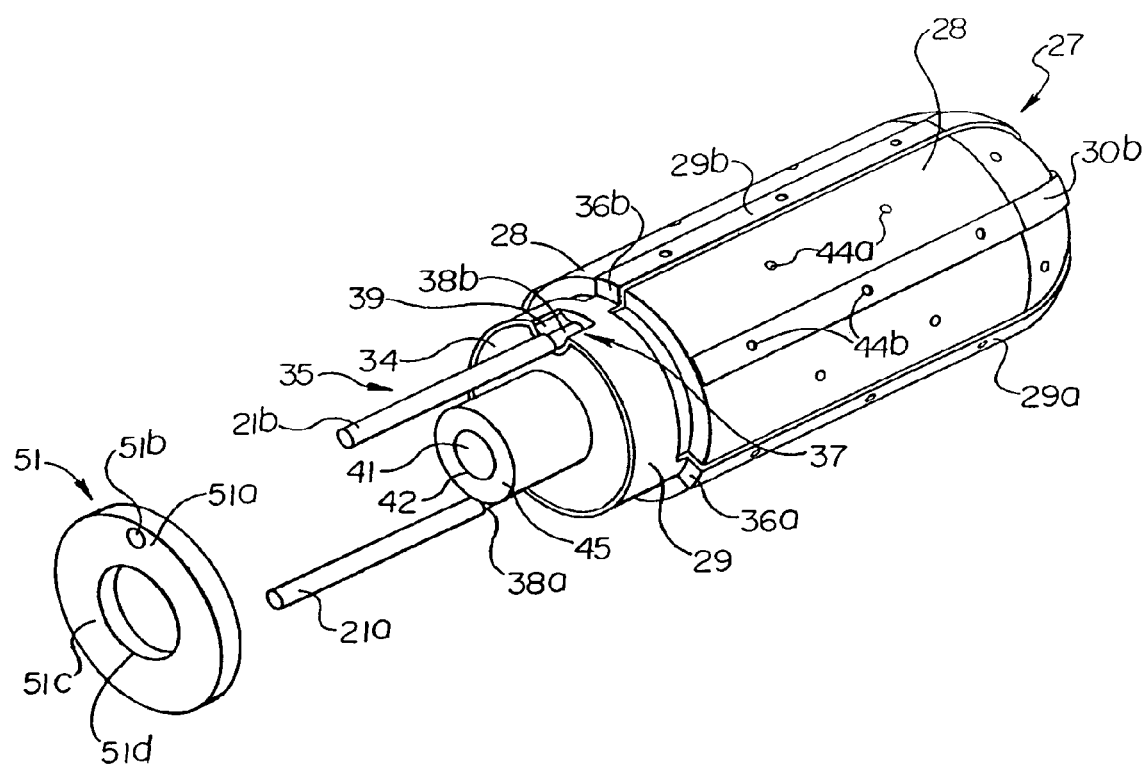
FIG. 10 is a schematic partially exploded close-up rear perspective view of the electrosurgical device of FIG. 9.

As best shown in FIGS. 10 and 12, electrosurgical device 5a is also preferably electrically connected to the conductors 38a, 38b of insulated electrical wires 21a, 21b, respectively, which have been passed through lumen 23 of tube 19 as branches of cable 9 which is connected to generator 6. However, in alternative embodiments, the tube 19 may incorporate the conductors 38a, 38b of wires 21a, 21b in the tube wall (in essence creating a multi-lumen tube comprising three lumens where two of the lumens are occupied exclusively by the conductors 38a, 38b of wires 21a, 21b) to reduce the complexity of items being passed down lumen 23. Thereafter, electrosurgical device 5a along with the flexible tube 19 and wires 21a, 21b contained therein may enter channel entrance opening 17l of device channel 17h and are thereafter passed through and along at least a portion of the length of device channel 17h until exiting from channel exit opening 17m.

Figure 14:
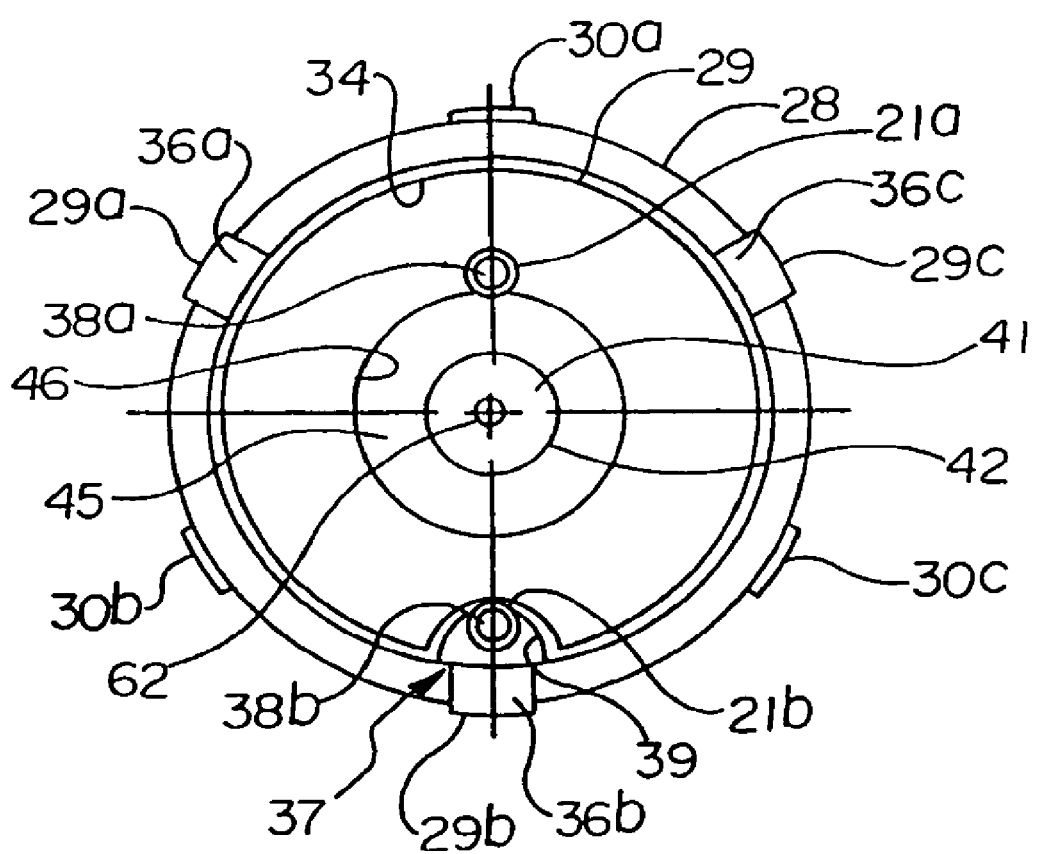
FIG. 14 is a schematic close-up rear view of the electrosurgical device of FIG. 9 with member 51 removed.
Figure 15:
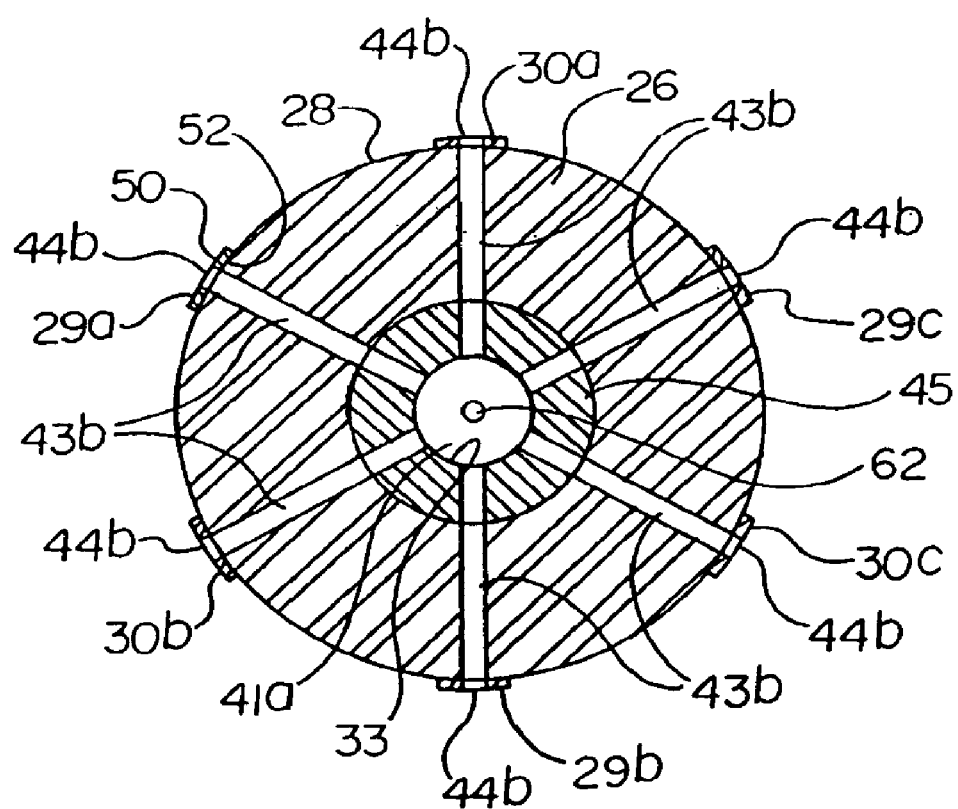
FIG. 15 is a schematic close-up cross-sectional view of the electrosurgical device of FIG. 9 taken in accordance with line 15-15 of FIG. 12.

As shown throughout FIGS. 9-16, and particularly FIGS. 12 and 15, electrosurgical device 5a comprises a probe body 26. Probe body 26 is preferably sized to pass from entrance 17l to the exit 17m of device channel 17h of scope 17. Probe body 26 may comprise a solid, electrically non-conductive, insulative material impervious to the flow of fluid 24 therethrough including, but not limited to, ceramic or polymer materials. Examples of non-conductive polymer materials include, but are not limited to, polyamide (a/k/a nylon), polyphthalamide (PPA), polyamideimide (PAI), polyetherimide (PEI), polyetheretherketone (PEEK), polyphenylenesulfide (PPS), polysulfone (PSO), polyethersulfone (PES), syndiotactic polystyrene (SPS), polyimide (PI) or any other non-conductive polymer, thermoplastic or thermoset. Probe body 26 may also comprise a liquid crystal polymer and, more particularly, an aromatic liquid crystal polyester which is reinforced with glass fiber, such as Vectra® A130 from Ticona, 90 Morris Avenue, Summit, N.J. 07901-3914. Where probe body 26 comprises a ceramic, it may comprise a machinable ceramic material such as sold under the tradename MACOR. In other embodiments, the non-conductive material of the probe body 26 may be coated with a non-conductive, lubricating or non-stick coating, such as polytetrafluoroethylene (PTFE).

As shown throughout FIGS. 9-16, electrosurgical device 5a is greatly enlarged since, for example, in one exemplary embodiment the cross-sectional dimension of device 5a, specifically its diameter, is about 7 French (about 2.4 mm or 0.095 inches). In another embodiment, the cross-sectional dimension of electrosurgical device 5a may be about 10 French (about 3.2 mm or 0.126 inches). In still other embodiments, electrosurgical device 5a may be configured with any cross-sectional dimension suitable to pass through the working channel of a viewing scope or of a trocar (also known as a cannula) where such a device is required.

As shown in FIGS. 9-12, for interacting with tissue, electrosurgical device 5a and, in particular, probe body 26, preferably comprise a generally cylindrical shape 32 with the distal end portion of the electrosurgical device 5a and probe body 26 preferably comprising a generally domed, hemispherical shape 67, such as that of a semi-circle, which provides a smooth, blunt contour outer surface.

As best shown in FIG. 12, electrosurgical device 5a preferably comprises a fluid flow manifold 40 located within probe body 26. Manifold 40 preferably comprises a discrete, rectilinear, longitudinally directed, central fluid flow passage 41, preferably located on-center about longitudinal axis 31 of electrosurgical device 5a. For device 5a, central flow passage 41 preferably extends between proximal end 35 and distal end 27 of electrosurgical device 5a through probe body 26 and has a central flow passage fluid entrance opening 42 located adjacent the proximal end 35 of probe body 26. As shown in FIG. 12, central flow passage 41 preferably extends into and is fluidly coupled with lumen 23 of flexible tube 19.

Figure 16:
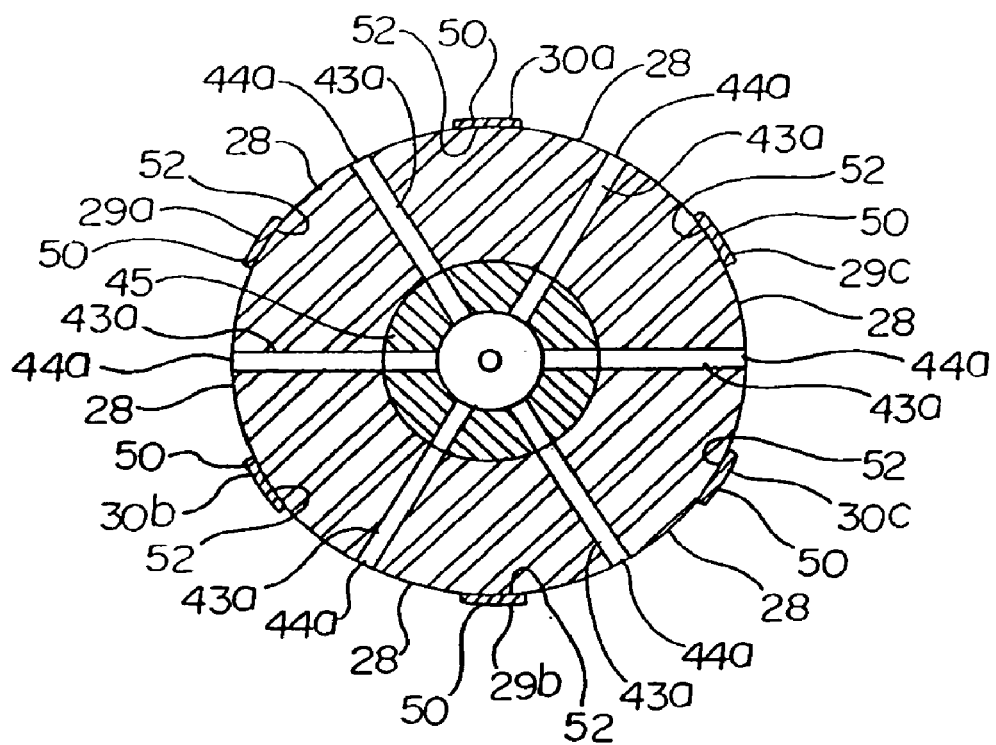
FIG. 16 is a schematic close-up cross-sectional view of the electrosurgical device of FIG. 9 taken in accordance with line 16-16 of FIG. 12.

As best shown in FIGS. 12, 15 and 16, manifold 40 preferably comprises at least one discrete, rectilinear, lateral fluid flow passage 43 which is fluidly coupled to central fluid flow passage 41. As shown, preferably manifold 40 comprises a plurality of discrete, rectilinear, lateral fluid flow passages 43a, 43b which are defined and spaced both longitudinally along and circumferentially around the probe body 26 and central fluid flow passage 41. More preferably the lateral fluid flow passages 43a, 43b are defined and spaced from proximal end 35 of electrosurgical device 5a through probe body 26 to the distal end 27 of electrosurgical device 5a through probe body 26.

Also as best shown in FIGS. 15 and 16, for device 5a lateral fluid flow passages 43a, 43b preferably each have a cross-sectional dimension, more specifically diameter, and corresponding cross-sectional area, less than the portion of central fluid flow passage 41 from which fluid 24 is provided. Also, as best shown in FIGS. 12, 15 and 16, the lateral fluid flow passages 43a, 43b which preferably extend through the cylindrical portion 32 of probe body 26 are preferably formed substantially at a right angle (e.g. within about 10 degrees of a right angle) to the central fluid flow passage 41, both longitudinally and circumferentially. Also as shown in FIGS. 12, 15 and 16, the lateral fluid flow passages 43a, 43b are preferably formed substantially at a right angle to the outer tissue interacting/treating surfaces 28, 50 of the electrosurgical device 5a.

Preferably, lateral fluid flow passages 43a, 43b extend from central fluid flow passage 41 to lateral flow passage fluid exit openings 44a, 44b located on surfaces of electrosurgical device 5a configured for interacting with and treating tissue.

As shown in FIGS. 12, 15 and 16, lateral flow passage fluid exit openings 44a, 44b are located on exposed outer surface 28 of probe body 26, or an exposed outer surface 50 of electrode 29a-c, 30a-c, which are discussed in greater detail later in this specification. More preferably, lateral fluid flow passages 43a, 43b preferably are configured to extend from central fluid flow passage 41 to lateral flow passage fluid exit openings 44a, 44b located on the outer surface 28 of probe body 26 and outer surface 50 of electrodes 29a-c, 30a-c, respectively, such that lateral flow passages 43a, 43b and associated fluid exit openings 44a, 44b are defined and spaced both longitudinally along and circumferentially around the outer surfaces 28 and 50 of electrosurgical device 5a, preferably between proximal end 35 of electrosurgical device 5a and the distal end 27 of electrosurgical device 5a and probe body 26.

As best shown in FIGS. 12, 15 and 16, central flow passage 41 may be lined by a liner 45, preferably comprising a non-corrosive, impervious (to fluid 24), metal tube (e.g. stainless steel tubing) located within a through bore 46 of probe body 26 which extends from proximal end 35 to distal end 27 of electrosurgical device 5a and probe body 26. Also as best shown in FIGS. 12, 15 and 16, preferably the outer wall surface of liner 45 contacts the inner surface of bore 46 of probe body 26 and discrete lateral fluid flow passages 43a, 43b extend through the wall thereof. Alternatively, liner 45 may comprise a cylindrical coil spring with the lateral openings provided between the coils of the spring.

As best shown in FIG. 12, distal wall section 25 of liner 45 adjacent distal end 27 of the electrosurgical device 5a and probe body 26 partially defines the distal end of the wide proximal portion 41a of the central flow passage 41 (with the proximal end of the distal narrow portion 41b of the central flow passage 41 defining the remainder of the distal end of the wide portion 41a of the central flow passage 41 in this embodiment). Distal wall section 25 of liner 45 also narrows the central flow passage 41 from wide portion 41a to narrow portion 41b and defines a narrow central fluid passage exit opening 62. As shown, in this manner, preferably, the distal portion of the central flow passage 41 comprises a counterbore configuration. In other words, two adjacent circular openings about the same axis, but of different diameter. More particularly, wide portion 41a and narrow portion 41b of central flow passage 41 preferably comprise the configuration of a counterbore adjacent the distal end 27 of electrosurgical device 5a.

During use of electrosurgical device 5a, the distal wall section 25 inhibits fluid flow from wide portion 41a through the narrow portion 41b of the central flow passage 41. In other words, distal wall 25 inhibits fluid 24 from exiting from the central fluid passage exit opening 62 as compared to a situation where distal wall 25 would not be used and the central flow passage 41 only would consist of wide portion 41a. In the above manner, at least a portion of the distal end of the central flow passage 41 is defined by an occlusion (i.e. wall section 25) formed by a portion of the electrosurgical device 5a.

More preferably, wall section 25 substantially occludes and inhibits fluid 24 from exiting from the central flow passage exit opening 62. Throughout this specification, occlusion of central flow passage 41 and the corresponding inhibiting of flow from exiting from the central fluid passage exit opening 62 of the central flow passage 41 can be considered substantial when the occlusion and corresponding inhibiting of flow results in increased flow from the lateral flow passages 43a, 43b. In other words, the occlusion functions as a fluid flow diverter and redirects fluid coming in contact therewith from flowing parallel with the longitudinal axis 31 of central flow passage 41 to flowing radially from the longitudinal axis 31 through lateral flow passages 43a, 43b.

As best shown in FIGS. 12, 15 and 16, preferably the probe body 26 has an outer surface 52 on which at least a portion of one energy providing member is located, overlies and is connected. As shown in FIGS. 9 and 10, the energy providing member preferably comprises a pair of electrical conductors 29, 30 which are respectively electrically connected to insulated wires 21a, 21b which are ultimately connected to generator 6. Conductors 29, 30 preferably comprise an electrically conductive metal, which is preferably non-corrosive, such as stainless steel or titanium.

The conductors 29, 30 are preferably configured to provide energy to tissue for hemostatic therapy and/or for tissue treatment of the wall of an anatomical tube. Each conductor 29, 30 may be branched into, for example, additional sub-conductors, such as comprising three elongated longitudinally directed strip electrodes 29a, 29b, 29c and 30a, 30b, 30c which will provide energy to treat tissue. As shown, the electrodes may be aligned generally parallel with the longitudinal axis 31 on the peripheral surface of the probe body 26 (comprising exposed probe body surfaces 28 and covered probe body surfaces 52) and are preferably angularly uniformly distributed, in this embodiment at angular intervals of 60 degrees. The electrodes 29a-c, 30a-c of conductors 29 and 30 are respectively successively spaced from each other by gaps, G. In one embodiment, the gaps G are generally at least about twice the widths W of the electrodes at the cylindrical portion 32 of the probe body 26. For a probe body 26 of a 2.4 mm diameter, the gaps G are about 0.8 mm and the widths W are about 0.4 mm. Generally, the wider the gap G between the electrodes the deeper the effect on tissue being treated.

Preferably, the electrodes 29a-c, 30a-c are provided alternating electrical current, so that the electrodes alternate polarity between positive and negative charges, and adjacent electrodes comprises opposite polarities at any given time to create an electrical field with current flow from the positive to negative charge. In other words, for example, preferably while electrodes 29a-c comprise a first polarity (e.g. positive), electrodes 30a-c comprise a second opposite polarity (e.g. negative). In the above manner, the plurality of uniformly distributed opposite electrode pairs formed around the longitudinal axis 31 create one or more bipolar electrical circuits, with the number of electrode poles generally equal to the number of circuits. For example, with the six electrode poles described above, an electrical array which extends circumferentially around longitudinal axis 31 and device 5a comprising six bipolar circuits is created between adjacent successive poles as shown by electrical field lines 57a-f in FIG. 13.

Conductors 29, 30, including electrodes 29a-c, 30a-c may comprise preformed metal which is then placed on probe body 26, or formed-in-place metal which comprises a metallic compound which is formed-in-place on the probe body 26, typically via painting or spraying. In one particular embodiment, conductors 29, 30 and electrodes 29a-c, 30a-c may be formed by first applying metal completely to the outer surfaces 28 and 52 of probe body 26 (such as by dip coating the outer surface in a liquid metal bath) then removing metal in excess of the conductors 29, 30 and electrodes 29a-c, 30a-c from the surface 28 to define the conductors 29, 30 and electrodes 29a-c, 30a-c, such as by the use of a laser.

Also as shown in FIGS. 9 and 10, where elongated, longitudinally directed electrodes are utilized (e.g. from the proximal end 35 to the distal end 27 of the electrosurgical device 5a and probe body 26), such as with electrosurgical device 5a, preferably at least three sets of opposite electrode poles are provided. In this manner, at least bipolar, and frequently greater, polar tissue contact and electrocoagulation can be achieved substantially independent of the orientation of the probe body 26 relative to the tissue treatment site. This is advantageous when the device 5a is used through endoscope 17 so that front end use (e.g. domed portion 67), sideways use (e.g. cylindrical portion 32) or oblique use (e.g. combination of domed portion 67 and cylindrical portion 32) of the electrosurgical device 5a results in at least a bipolar contact with the tissue treatment site.

As best shown in FIGS. 10 and 14, electrodes 29a-c of conductor 29 are preferably electrically coupled to each other at the proximal end 35 of the probe body 26. Preferably, electrodes 29a-c of conductor 29 are electrically coupled via a conductor 29 which comprises an electrically conductive radial band, preferably located on a radially recessed shoulder 34 of probe body 26 located at the proximal end 35 of probe body 26. The electrical coupling between electrodes 29a-c and conductor 29 is preferably made via radially displaced localized conductive tabs 36a-c. In turn, conductor 38b of insulated wire 21b is preferably connected to band preferably in a notch 37 formed in the band and in shoulder 34, where notch 37 is sized to receive conductor 38b of wire 21b. Conductor 38b of insulated wire 21b is preferably connected to a surface 39 of notch 37 via an electrical connector comprising solder (e.g. silver) from soldering.

As best shown in FIGS. 9 and 12, electrodes 30a-c of conductor 30 are preferably electrically coupled to each other at the distal end 27 of the electrosurgical device 5a and probe body 26. Preferably, electrodes 30a-c of conductor 30 are electrically coupled via a conductor 30 comprising an electrically conductive hub preferably located at the distal end 27 of the electrosurgical device 5a and probe body 26. A wall section 47 of the conductor 30 overlying wall section 25 of liner 45 may also function an occlusion which either partially defines the distal portion of the central flow passage 41 (i.e. where central flow passage 41 comprises a narrow portion 41b and a central fluid passage exit opening 62) or completely defines the distal end of the central flow passage 41 (i.e. where the central flow passage does not continue through the wall section 47 of conductor 30), particularly when liner 45 is not occluded at its distal end (i.e. does not include wall section 25).

Conductor 30 is preferably electrically coupled to hollow conductive metal liner 45 to which, in turn, conductor 38a of insulated wire 21a is preferably connected to a surface of hollow metal liner 45 at the proximal end 35 of probe body 26 via an electrical connector comprising solder (e.g. silver) from soldering. Alternatively where, for example, liner 45 is not utilized, conductor 38a of insulated wire 21a may be connected to an inner surface 49 of conductor 30.

As shown in FIGS. 9 and 16, preferably the plurality of lateral flow passages 43a which extend through probe body 26 to fluid exit openings 44a are defined and spaced along the outer surface 28 of probe body 26 between at least one pair of adjacent electrodes. As shown, preferably the plurality of lateral flow passage fluid exit openings 44a are configured to form both longitudinal and circumferential straight rows, and are preferably uniformly spaced relative to one another. Also, preferably lateral flow passages 43a are configured to distribute fluid flow exiting from fluid exit openings 44a substantially uniformly. Lateral flow passages 43a of this exemplary embodiment preferably have a cross-sectional dimension (e.g. diameter) in the range between and including about 0.1 mm to 2 mm and more preferably have a diameter in the range between and including about 0.15 mm to 0.2 mm.

Also as shown in FIGS. 9 and 15, preferably the plurality of lateral flow passages 43b which extend through probe body 26 and at least one electrode 29a-c, 30 a-c to fluid exit openings 44b are defined and spaced along the outer surface 50 of electrodes 29a-c, 30a-c. As shown, preferably the plurality of lateral flow passage fluid exit openings 44b are configured to form both longitudinal and circumferential straight rows, and are preferably uniformly spaced relative to one another. Also, preferably lateral flow passages 43b are configured to distribute fluid flow exiting from fluid exit openings 44b substantially uniformly. Lateral flow passages 44b of this exemplary embodiment preferably have a cross-sectional dimension (e.g. diameter) in the range between and including about 0.1 mm to 2 mm and more preferably have a diameter in the range between and including about 0.15 mm to 0.2 mm.

As best shown in FIG. 10, electrical device 5a preferably further comprises a member 51 which comprises a gasket portion 51a configured to electrically insulate conductors 38a, 38b from one another and inhibit a short circuit (i.e. a low resistance, alternate path through which current will flow, often resulting in damage, rather than through the load circuit) from forming between conductors of different electrical potential (e.g. conductors 29/38b with conductors 30/38a) in the presence of electrically conductive fluid, which would cause electrical current to flow between conductors (e.g. 29/38b and 30/38a) prior to the current reaching electrodes 29a-c and 30a-c, thus bypassing or detouring away from the electrodes. Member 51 preferably comprises an insulative flexible polymer material, such as an elastomer and, in this embodiment, preferably comprises the geometry of a thin, flat circular member, such as that of a washer. As shown in FIG. 10, gasket portion 51a surrounds aperture 51b through which wire 21b extends. Thereafter, gasket portion 51a preferably forms a gasket with the insulator of wire 21b to inhibits fluid 24 from lumen 23 of tube 19 from contacting conductors 38b and 29.

Member 51 also preferably includes a second gasket portion 51c which surrounds aperture 51d through which liner 45 extends and thereafter forms a gasket with the outer surface of liner 45 to also inhibit fluid 24 from lumen 23 of tube 19 from contacting conductor 38b or 29.

In other embodiments, electrical device 5a may further comprise a sensor, such as probe body 26 itself, for sensing, for example, temperature, pressure or saline impedance sensor for sensing the phase change associated with the onset of boiling, or which may be located in or on probe body 26, adjacent an electrode and/or the tissue.

As best shown in FIGS. 12, 15 and 16, probe body 26 preferably comprises a circular shape with a uniform diameter along the longitudinal length of the cylindrical portion 32. As best shown in FIGS. 15 and 16, the outer surface 50 of at least a portion of at least one of the electrodes 29a-c, 30a-c is stepped up or otherwise protruding relative to an adjacent exposed outer surface 28 of the probe body 26 by the thickness of the electrodes, preferably in a thickness range between and including about 0.01 mm to 2.0 mm and, more preferably, in the range between and including about 0.1 mm to 0.5 mm. As shown in FIGS. 15 and 16, the outer surface 50 of all of the electrodes 29a-c, 30a-c is stepped up relative to an adjacent exposed outer surface 28 of the probe body 26 by the thickness of the electrodes.

Figure 17:
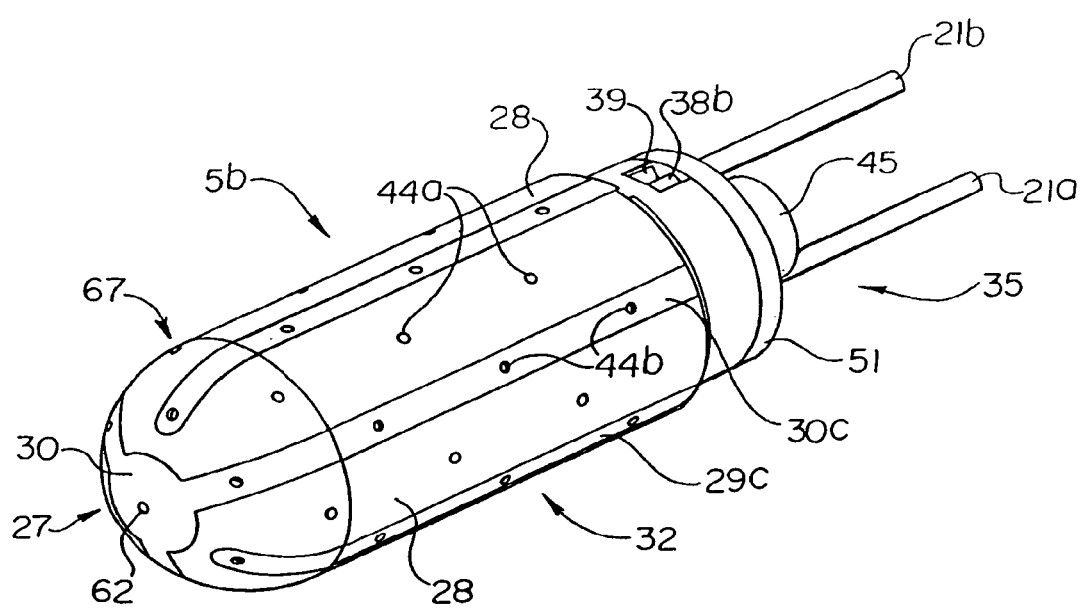
FIG. 17 is a schematic close-up front perspective view of an electrosurgical device according to another embodiment of the invention.
Figure 18:
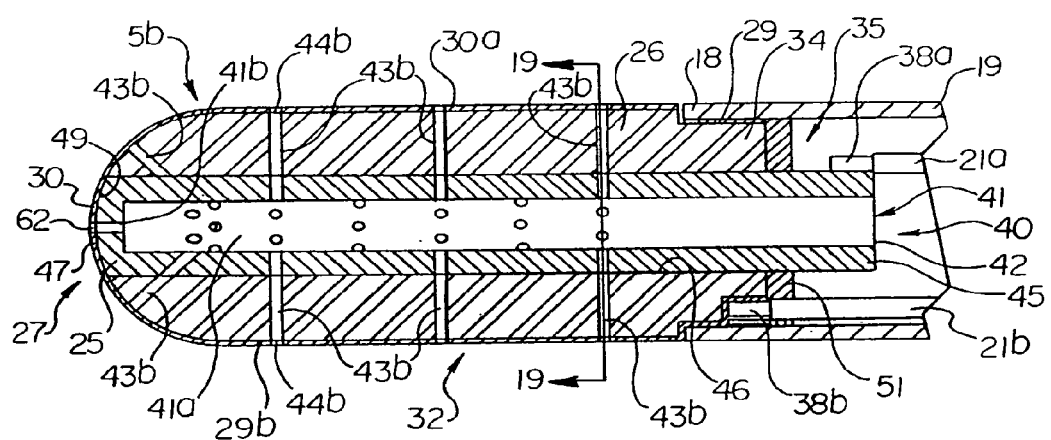
FIG. 18 is a schematic close-up cross-sectional view of the assembly of the electrosurgical device of FIG. 17 and tube 19 taken in accordance with line 12-12 of FIG. 13.
Figure 19:
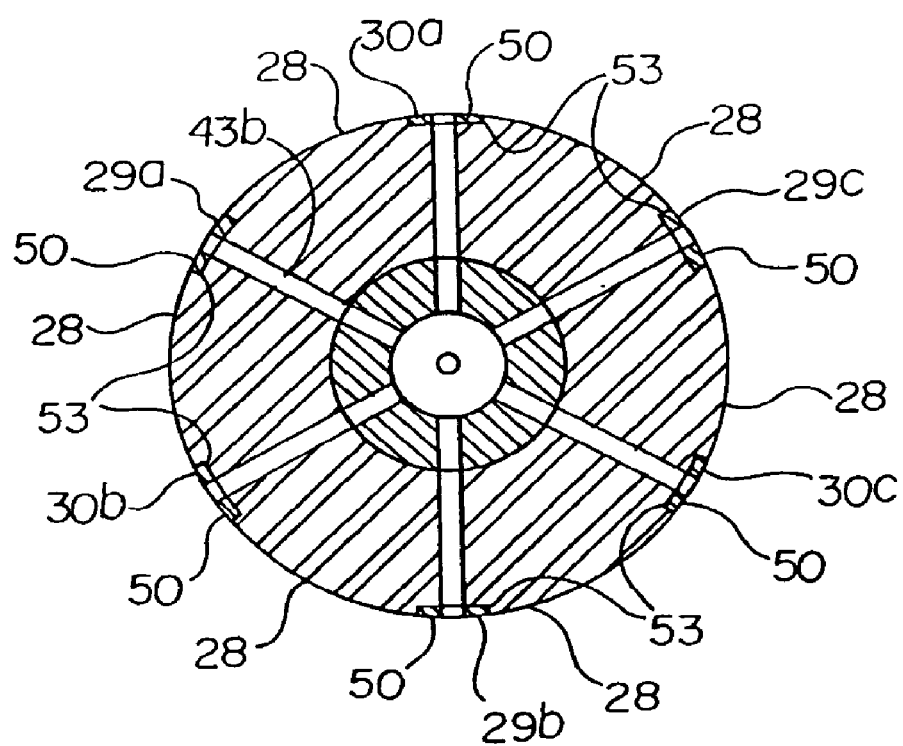
FIG. 19 is a schematic close-up cross-sectional view of the electrosurgical device of FIG. 17 taken in accordance with line 19-19 of FIG. 18.

Another exemplary electrosurgical device of the present invention which may be used in conjunction with the system of the present invention is shown at reference character 5b in FIG. 17, and more particularly in FIGS. 17-19. As best shown in FIG. 19, at least a portion of at least one of the electrodes 29a-c, 30a-c is located in a recess such that the outer surface 50 of the electrodes is flush relative to an adjacent exposed outer surface 28 of the probe body 26. As shown in FIG. 19, all the electrodes 29*a-c*, 30*a-c* are located in recesses 53 with the depth of the recesses 53 equal to the thickness of the electrodes such that the outer surface 50 of the electrodes 29*a-c*, 30*a-c* is flush relative to an adjacent exposed outer surface 28 of the probe body 26. In this manner, device 5*b* may tend to move along the surface of the tissue more easily than 5*a* as the surface roughness associated with protruding electrodes is eliminated.

Figure 20:
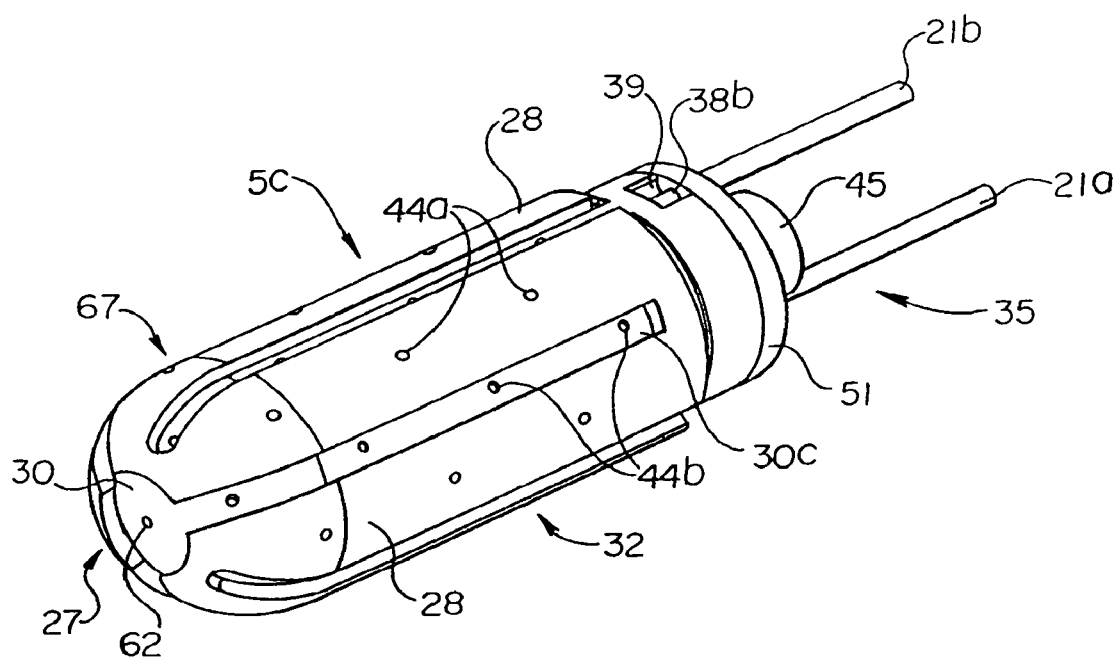
FIG. 20 is a schematic close-up front perspective view of an electrosurgical device according to another embodiment of the invention.
Figure 21:
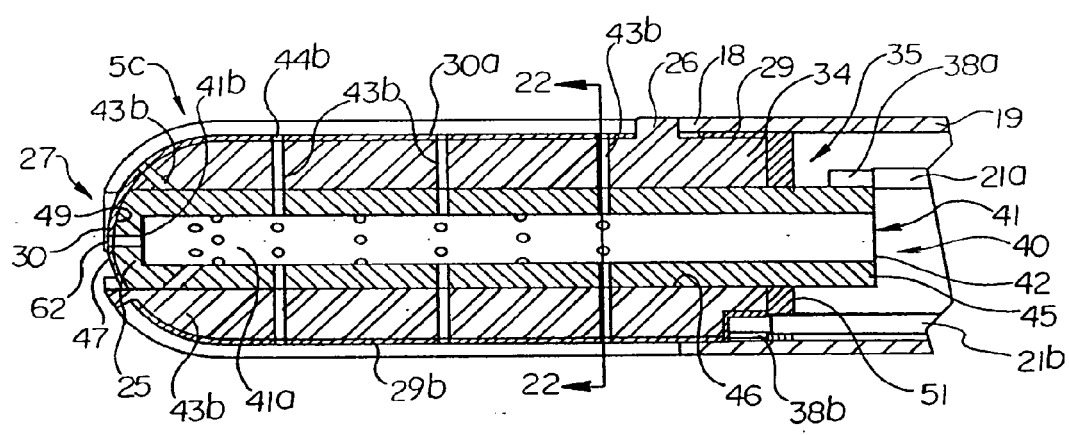
FIG. 21 is a schematic close-up cross-sectional view of the assembly of the electrosurgical device of FIG. 20 and tube 19 taken in accordance with line 12-12 of FIG. 13.
Figure 22:
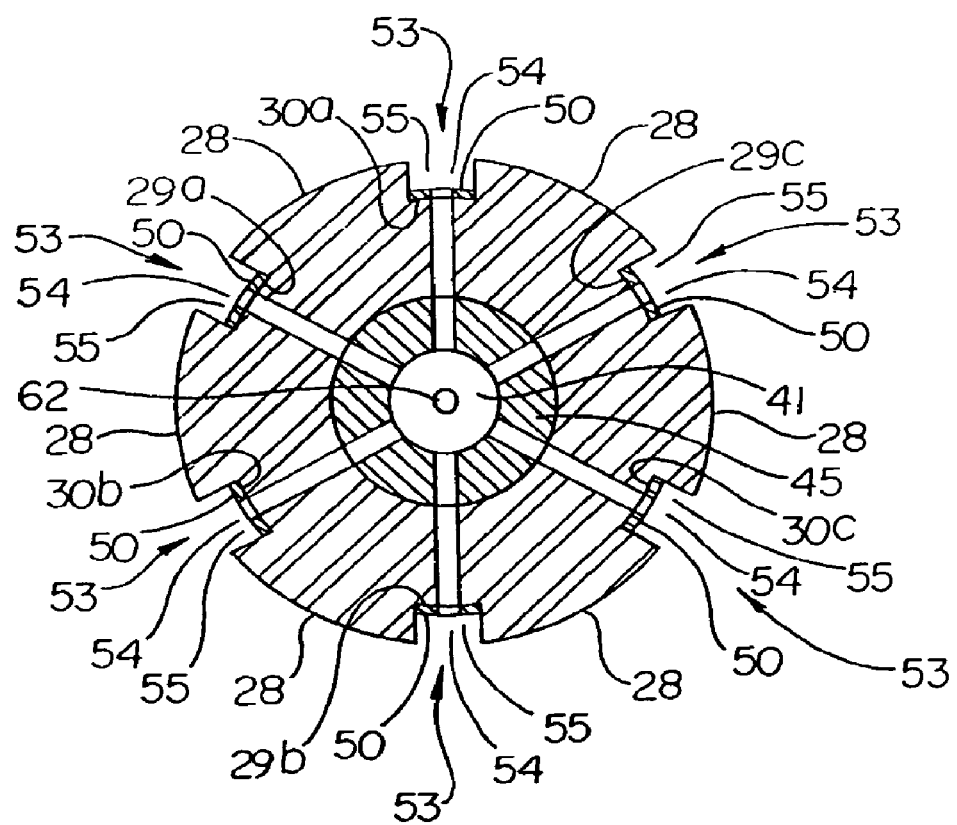
FIG. 22 is a schematic close-up cross-sectional view of the electrosurgical device of FIG. 20 taken in accordance with line 22-22 of FIG. 21.

Another exemplary electrosurgical device of the present invention which may be used in conjunction with the system of the present invention is shown at reference character 5*c* in FIG. 20, and more particularly in FIGS. 20-22. As best shown in FIG. 22, recess 53 provides, at least in part, at least one elongated fluid flow channel 54 for fluid 24. Also as shown in FIG. 22, preferably at least a portion of at least one of the electrodes 29*a-c*, 30*a-c* is located in the recess 53, and preferably such that the outer surface 50 of the electrodes is stepped down or otherwise recessed relative to an adjacent exposed outer surface 28 of the probe body 26. As shown in FIG. 22, all the electrodes 29*a-c*, 30*a-c* are located in recesses 53, with the depth of the recesses 53 greater than the thickness of the electrodes such that the outer surface 50 of the electrodes 29*a-c*, 30*a-c* is stepped down relative to an adjacent exposed outer surface 28 of the probe body 26. Also as shown in FIG. 22, the fluid flow channel 54 is preferably provided in the portion of the recess 53 overlying the outer surface 50 of the electrodes 29*a-c*, 30*a-c*.

Preferably the configuration of the fluid flow channel 54 as provided by geometry (e.g. width, depth), the material and/or surface treatment of the probe body 26, and/or the material and/or surface treatment of the electrodes 29*a-c*, 30*a-c*, and may be arranged such that surface tension will act to retain fluid collected in the channel 54 where the force of gravity is acting to remove the fluid from the channel 54. However, while it is desirable that a certain predetermined amount of surface tension act to retain fluid collected in the channel 54 in the presence of gravity, the surface tension must be balanced against the inhibition of fluid flow from lateral flow passages 43*b*. While partial inhibition from lateral flow passages 43*b* is acceptable, fluid flow channel 54 should not be configured and arranged such that surface tension will act to completely inhibit or prevent fluid from flowing out of lateral flow passages 43*b*.

Among other things, fluid flow channel 54 provides a distribution conduit for distributing fluid contained therein, which has passed through lateral fluid flow passages 43*b* from central flow passage 41, more uniformly on the outer surface 50 of the electrodes 29*a-c*, 30*a-c* as compared to the situation where fluid flow channel 54 is not used. In other words, the use of fluid flow channel 54 will generally increase the surface area 50 of the electrodes 29*a-c*, 30*a-c* covered with fluid from lateral fluid flow passages 43*b* as compared to the situation where fluid flow channel 54 is not used.

Among other things, fluid flow channel 54 also provides a distribution conduit for distributing fluid contained therein, which has passed through lateral fluid flow passages 43*b* from central flow passage 41, more uniformly on the adjacent exposed outer surfaces 28 of the probe body 26 as compared to the situation where fluid flow channel 54 is not used. For example, the use of fluid flow channel 54 will generally increase the surface area 28 of the probe body 26 covered with fluid from lateral fluid flow passages 43*b* as a result of fluid overflowing out of the channel 54 along the longitudinal length of the channel 54 and flowing over the surface 28 of the probe body 26 as compared to the situation where fluid flow channel 54 is not used.

In use, when tissue 20 overlies and occludes the opening 55 of fluid flow channel 54 for a portion of its longitudinal length, thus inhibiting fluid flow exiting therefrom, fluid from channel 54 may still be expelled from the electrosurgical device 5*c* after flowing longitudinally in the channel 54 to a remote location, typically at distal end 27 of electrosurgical device 5*c* and probe body 26, where the channel 54 is unoccluded and uninhibited to fluid flow exiting therefrom.

Figure 23:
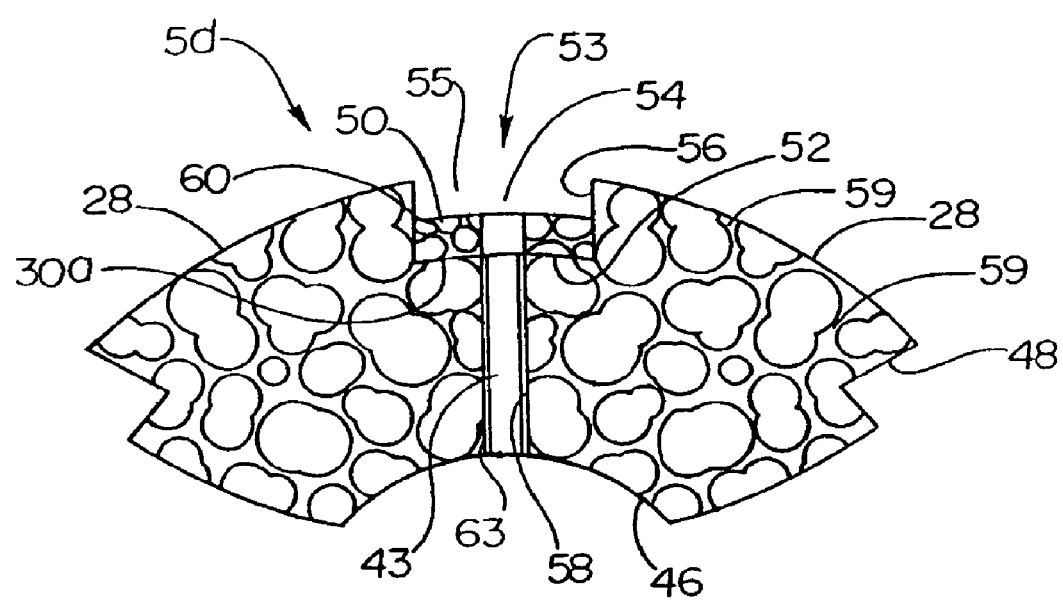
FIG. 23 is a schematic close-up partial cross-sectional view of an electrosurgical device according to another embodiment of the invention taken in accordance with line 22-22 of FIG. 21.

However, in certain instances, it may be possible that fluid flow channel 54 may be occluded by tissue 20 completely along its longitudinal length, thus completely inhibiting fluid flow from exiting through opening 55. In order to overcome this problem, at least a portion of probe body 26 may comprise a material pervious to the passage of fluid 24, therethrough, such as a porous material. As shown in FIG. 23, in another embodiment of the electrosurgical device of the present invention, as shown at reference character 5*d* in FIG. 23, the wall 56 of channel 54, as well as exposed outer surface 28 of probe body 26 are porous and connected by a plurality of tortuous paths 59 in the porous material. Consequently, rather than flowing out of channel 54 from a direct opening 55, which may be occluded by tissue 20, the fluid may exit indirectly from the flow channel 54 by first flowing through tortuous paths 59 of probe body 26 from side walls 56 of the channel and then exit the probe body 26 from surface 28, which may be in unoccluded by tissue 20. Alternatively, if adjacent surface 28 of the probe body 26 is also occluded by tissue 20, the fluid may continue to flow through tortuous paths 59 of probe body 26 and exit the probe body 26 from a surface 48 of a remote flow channel 54 or surface 28, 50, which may be in unoccluded by tissue 20.

As also shown in FIG. 23, in addition to the probe body 26 comprising a porous material, at least one of the electrodes 29*a-c*, 30*a-c* may also comprise a porous material. Consequently, fluid flowing through the tortuous paths 59 of the probe body 26 may exit from surface 52 of the probe body 26 covered by an electrode 29*a-c*, 30*a-c*, flow though the tortuous paths 60 of the electrode 29*a-c*, 30*a-c* and then exit from outer surface 50 of the electrode 29*a-c*, 30*a-c* to provide similar advantages as the porous probe body 26.

Where the probe body 26 and/or electrodes 29*a-c*, 30*a-c* comprise a porous material, the discrete, rectilinear lateral fluid flow passages 43*a*, 43*b* may be either supplemented with or replaced by the plurality of tortuous, interconnected passages 59 and/or 60 formed in the porous material with a porous surface 28 and/or 50 to more evenly distribute fluid flow and allow infusion of the conductive solution to the tissue treatment site. Also alternatively, the lateral fluid flow passages 43*a*, 43*b* may extend towards surfaces 28 and/or 50, but terminate prior to surfaces 28 and/or 50 and not extend thereto, with passages 59 and/or 60 in fluid communication with lateral flow passages 43*a*, 43*b* thereafter providing fluid 24 to surfaces 28 and/or 50.

Where the probe body 26 comprises a porous non-electrically conductive material, the conductors 38*a*, 38*b* and corresponding electrodes 29*a-c*, 30*a-c*, respectively, may still be further insulated from one another to reduce power losses associated with any short circuit which may develop through the probe body 26 and, more particularly, through the conductive fluid flowing through the tortuous paths 59 of the probe body 26. As shown also in FIG. 23, in order to further insulate the respective poles from one another, a water resistant or water proof coating 58 may be located between surfaces of probe body 26 adjoining portions of the electrical circuit (e.g. conductors 38a, 38b and electrodes 29a-c, 30a-c), such as surface 33 of liner 45, surface 63 of lateral flow passage 43, the surface if the central flow passage 41, the surface of bore 46 of probe body 26 and/or notch surface 39.

With regards to porous electrodes 29a-c, 30a-c porous sintered metal is available in many materials (such as, for example, 316L stainless steel, titanium, Ni-Chrome) and shapes from companies such as Porvair, located in Henderson, N.C.

Porous metal components can be formed by a sintered metal powder process or by injection molding a two-part combination of metal and a material that can be burned off to form pores that connect (open cell) to each other. With sintering, for example, typically solid particles of material are placed in a mold under heat and pressure such that the outer surface of the particles soften and bond to one another with the pores comprising the interstices between the particles. Alternatively, when porosity is formed by burning off material, it is not the interstice between the particles which provides the porosity as with sintering, but rather a partial evisceration of the material generally provided by the removal of a component with a lower melt temperature than the burn off temperature.

With regards to a non-electrically conductive porous probe body 26, porous polymers and ceramics can be used to replace non-porous polymers and ceramics, respectively. Suitable polymer materials include high temperature open cell silicone foam and porous polycarbonates, among others. Different from sintering or evisceration of material, formation of porosity in open cell polymer foams is typically accomplished by the introduction of gas bubbles, either chemically or physically, into the polymer during its formation or melt phase which form a cellular structure. However, sintering or evisceration of material may also be used with polymer materials. While the porous polymers themselves are generally non-conductive, they may also be used to conduct the RF energy through the porous polymer thickness and surface to the tissue to be treated by virtue of conductive fluid contained within the plurality of interconnected tortuous passages.

Porous ceramics also generally fall into the category of being non-conductive, since they could distribute conductive fluid flow, withstand high temperatures and be machinable or moldable for manufacturing purposes. Preferably, the material used transmits both fluid flow and electrical energy; thus, materials with properties between high-electrical conductivity metals and low electrical conductivity polymers are also contemplated, such as porous carbon-filled polymers. In these embodiments, conductive fluid flow is distributed along the length of the electrodes, where porous material is used to fabricate the electrodes. All or a portion of the electrodes can be porous according to the invention.

Preferably the tortuous passages 59 and 60 in the porous materials have a pore size (cross-sectional dimension) in the range between and including about 2.5 micrometers (0.0025 mm) to 500 micrometers (0.5 mm) and more preferably has pore size in the range between and including about 10 micrometers (0.01 mm) to 120 micrometers (0.12 mm). Even more preferably, the porous material has a pore size in the range between and including about 20 micrometers (0.02 mm) to 80 micrometers (0.08 mm).

In addition to providing a more uniform distribution of fluid exiting from channel 54, the porous materials also provides other advantages. For example, lateral fluid flow passages 43a, 43b are difficult to mold or machine below a size of 0.276 millimeters (0.007 inches). Conversely, the porous material may provide passages of a smaller dimension. Furthermore, in addition to providing smaller fluid passages, when the probe surface 28 and/or electrode surface 50 in contact with tissue 20 are porous and dissipate fluid, tissue 20 is less apt to stick to the surfaces 28 and/or 50 as compared to the situation where the surfaces 28 and/or 50 are not porous. In addition, by providing fluid to surfaces 28 through tortuous paths 59, heated and/or electrified fluid can now be provided more uniformly to surface 28, which results in a wider tissue treatment region as compared to when the surfaces 28 is not porous.

Preferably the porous material provides for the wicking (i.e. drawing in of fluid by capillary action or capillarity) of the fluid into the pores of the porous material. In order to promote wicking of the fluid into the pores of the porous material, preferably the porous material also comprises a hydrophilic material, which may be provided, for example, by the porous material itself with or without post treating (e.g. plasma surface treatment such as hypercleaning, etching or micro-roughening, plasma surface modification of the molecular structure, surface chemical activation or crosslinking), or by a coating provided thereto, such as a surfactant.

As shown in embodiments 5c and 5d, and more specifically in FIGS. 22 and 23, recess 53 comprises a rectangular cross section formed in part by a first side wall, a second opposing side wall and a bottom wall. Furthermore, electrodes 29a-c, 30a-c also comprise a rectangular cross-sections, and lateral flow passages 43b extend through the electrodes. However, in other embodiments of the invention, recess 53 and electrodes 29a-c, 30a-c may comprises features and cross-sectional shapes other than that of a rectangle. These various electrosurgical devices are discussed particularly in embodiments 5e-5h in the following paragraphs. Discussion of embodiments 5e-5h focuses on one particular electrode of the group 29a-c, 30a-c, recess 53, flow channel 54 and lateral flow passage 43, as the case may be. However, it should be understood that the features discussed for each embodiment 5e-5h may equally apply to all the electrodes of the group 29a-c, 30a-c, recesses 53, flow channels 54 and lateral flow passages 43 of the respective embodiment.

Figure 24:
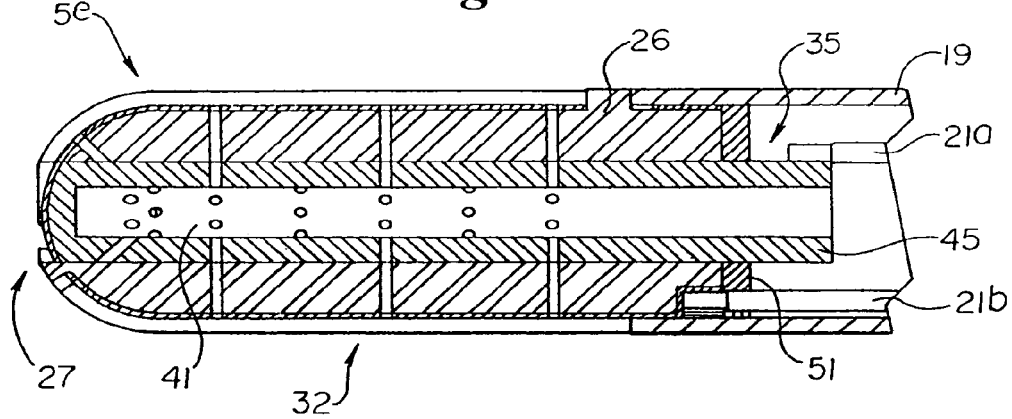
FIG. 24 is a schematic close-up cross-sectional view of the assembly of an electrosurgical device according to another embodiment of the invention and tube 19 taken in accordance with line 12-12 of FIG. 13.

In an alternative embodiment, rather than an occlusion formed by a portion of the electrosurgical device 5a defining at least a portion of the distal end of the central flow passage 41, an occlusion may completely define the distal end of the central flow passage 41. As shown in FIG. 24, for device 5e distal wall section 25 of liner 45 completely defines the end of the central flow passage 41. In other words, central flow passage 41 only comprises wide portion 41a and does not comprise narrow portion 41b or a central fluid passage exit opening 62. In this manner, the distal end of the central flow passage 41 comprises a blind end. In other words, the central flow passage 41 does not continue through electrosurgical device 5e. The distal end of the central flow passage terminates within the confines of the electrosurgical device 5e and is closed by a portion of the electrosurgical device structure, in this embodiment wall section 25 of liner 45, forming the distal end of the central flow passage 41.

Figure 25:
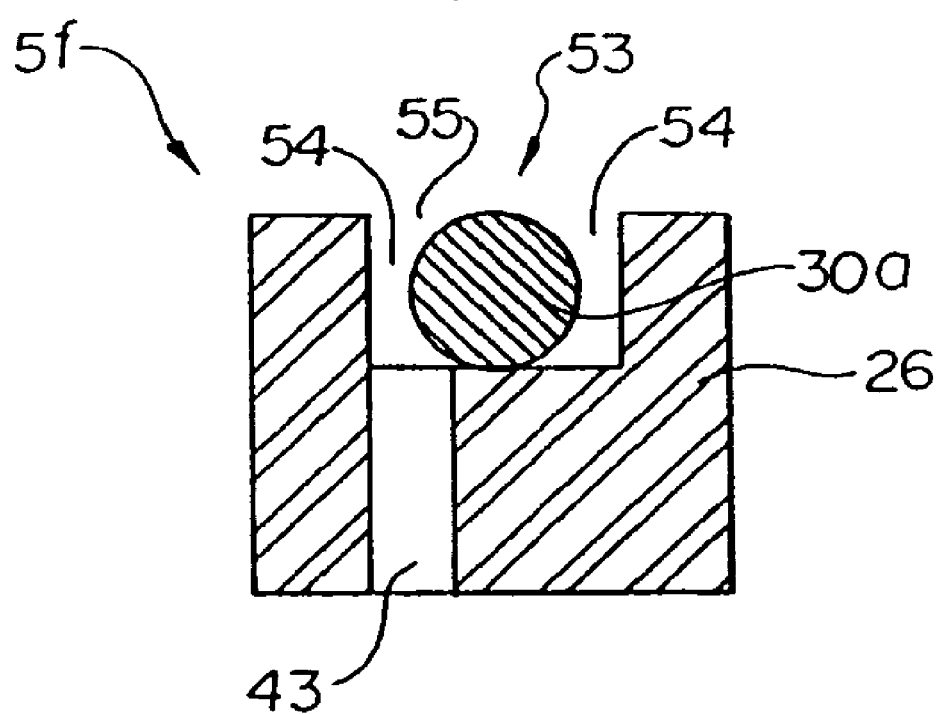
FIG. 25 is a schematic close-up partial cross-sectional view of an electrosurgical device according to another embodiment of the invention taken in accordance with line 22-22 of FIG. 21.

As shown in FIG. 25, electrode 30a of electrosurgical device 5f comprises a circular cross-sectional shape, preferably with a constant diameter. More particularly, preferably wire conductor 38a of wire 21a comprises electrode 30a. In this manner, conductor 38a and electrode 30a comprise a unitarily formed piece which reduces complexity. In this embodiment, it should be understood that the thickness of the electrode is equal to the width of the electrode, with both equal to the diameter of the electrode. Furthermore, electrosurgical device 5f comprises a number of important distinctions from embodiments 5a-5e disclosed thusfar.

As shown in FIG. 25, lateral flow passage 43 does not extend through electrode 30a, and does not have to extend through electrode 30a before having fluid communication with fluid flow channel 54, which reduces complexity. As shown, lateral flow passage 43 is located directly beneath fluid flow channel 54, rather than having electrode 30c in between. Also as shown, lateral flow passage 43 is at least partially located beneath overlying electrode 30c with a portion of fluid flow channel 54 located in between.

Also as shown in FIG. 25, in addition to a portion of fluid flow channel 54 overlying a portion of the electrode 30a in recess 53, at least a portion of fluid flow channel 54 underlies a portion of the electrode 30a and at least a portion of fluid flow channel 54 is located on at least one longitudinal side of a portion of the electrode 30a in recess 53. More particularly, as shown in FIG. 25, a portion of fluid flow channel 54 is located on two longitudinal sides of the electrode 30a in recess 53. Thus, with the configuration of electrosurgical device 5f, fluid flow channel 54 is not limited to only overlying electrode 30a, but rather can take on a number of different localities within recess 53, depending on the application.

Figure 26:
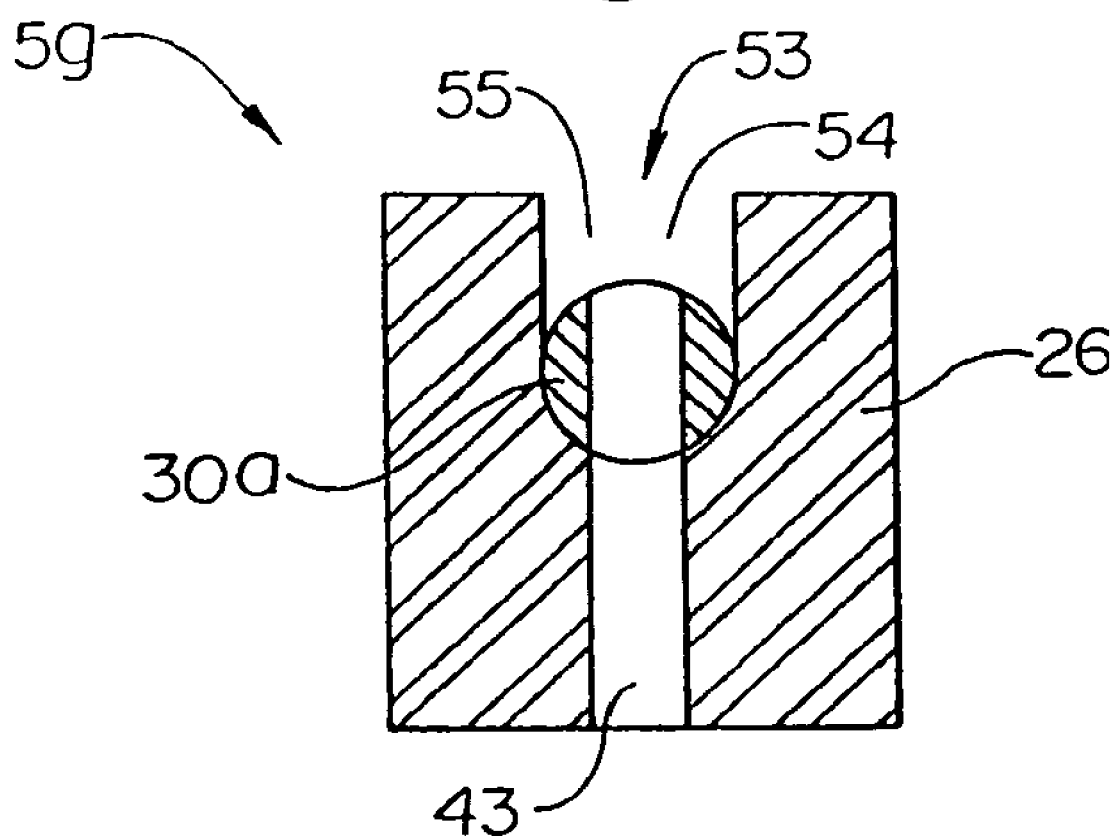
FIG. 26 is a schematic close-up partial cross-sectional view of an electrosurgical device according to another embodiment of the invention taken in accordance with line 22-22 of FIG. 21.

As shown in FIG. 26, electrode 30a of electrosurgical device 5g also comprises a circular cross-sectional shape, preferably with a constant diameter. Similar to electrosurgical device 5f, preferably wire conductor 38a of wire 21a also comprises electrode 30a. However, in contrast to electrosurgical device 5f, lateral flow passage 43 of device 5g extends through electrode 30a. In order to better facilitate the formation of lateral flow passage 43 through electrode 30a, preferably recess 53 is configured to receive and properly seat electrode 30a therein substantially without any side-to-side movement and prior to the formation of lateral flow passage 43. As shown, the seat for electrode 30a in recess 53 comprises a semi-circle of substantially the same width, more specifically diameter, as that of electrode 30a. Preferably electrode 30a is first seated in recess 53 without lateral flow passage 43 formed therein, then, once seated, lateral flow passage 43 is formed through electrode 30a and probe body 26 and liner 45 simultaneously. In a preferred embodiment, lateral flow passage 43 is formed by a laser acting directed at the outer surface of the electrode 30a.

Figure 27:
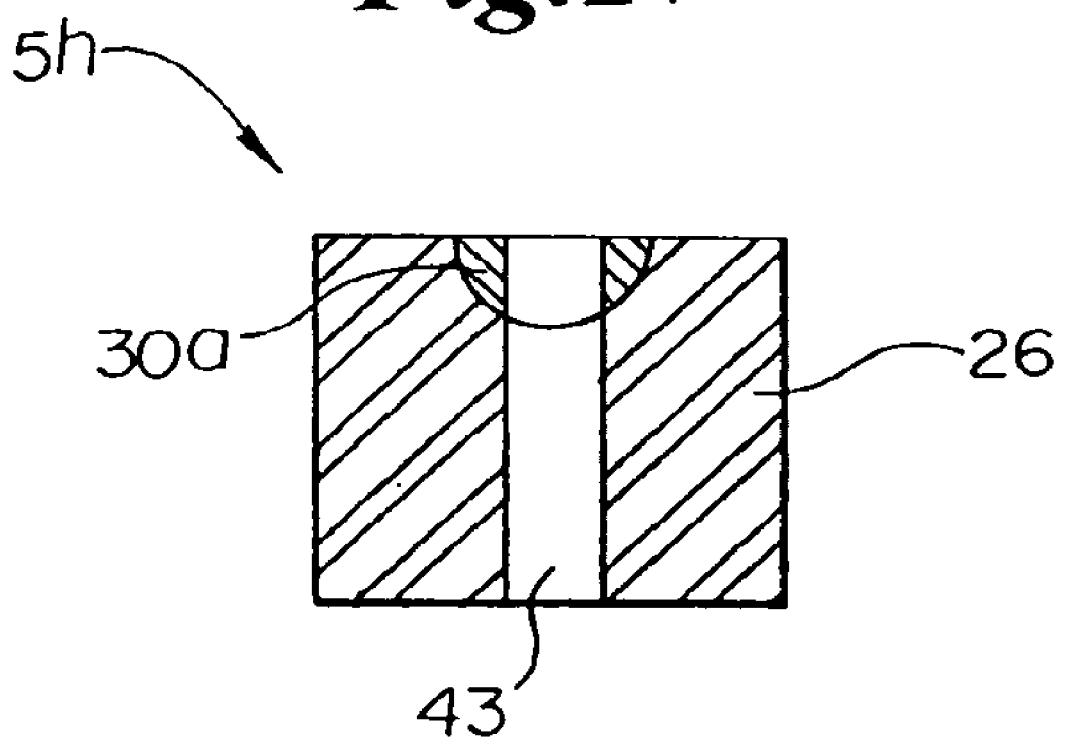
FIG. 27 is a schematic close-up partial cross-sectional view of an electrosurgical device according to another embodiment of the invention taken in accordance with line 22-22 of FIG. 21.

As shown in FIG. 27, electrode 30a and recess 53 of electrosurgical device 5h comprises a semi-circular cross-sectional shape and no fluid flow channel 54 is present. However, the seating of electrode 30a and the formation of lateral flow passage 43 is preformed similarly to that disclosed for electrosurgical device 5g.

Figure 28:
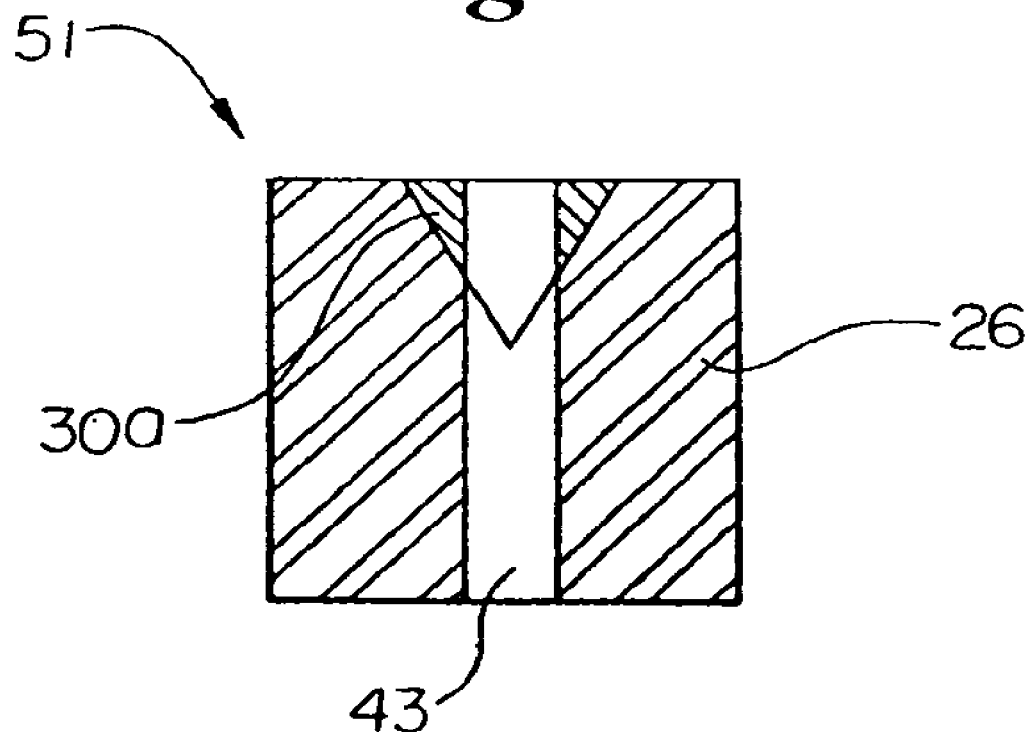
FIG. 28 is a schematic close-up partial cross-sectional view of an electrosurgical device according to another embodiment of the invention taken in accordance with line 22-22 of FIG. 21.

As shown in FIG. 28, electrode 30a and recess 53 of electrosurgical device 5i comprises a triangular cross-sectional shape and, similar to electrosurgical device 5h, no fluid flow channel 54 is present. However, as with electrosurgical device 5h, the seating of electrode 30a and the formation of lateral flow passage 43 is preformed similarly to that disclosed for electrosurgical device 5g. In other words, the seating portion of recess 53 comprises substantially the same size and shape as the seating portion of the electrode 30a.

Figure 29:
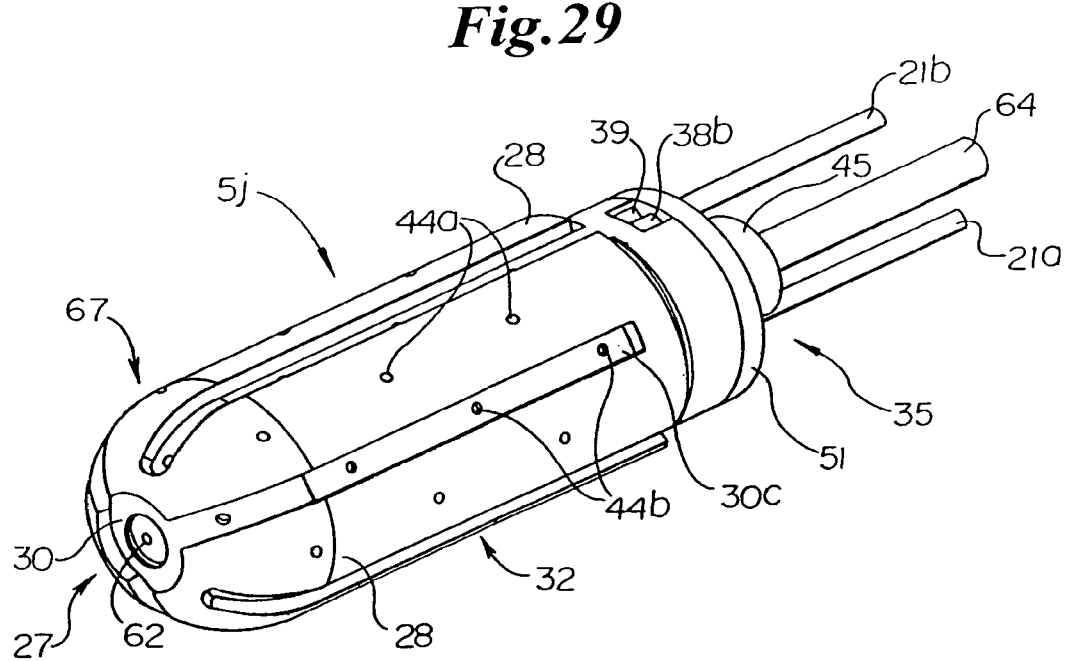
FIG. 29 is a schematic close-up front perspective view of an electrosurgical device according to another embodiment of the invention.
Figure 30:
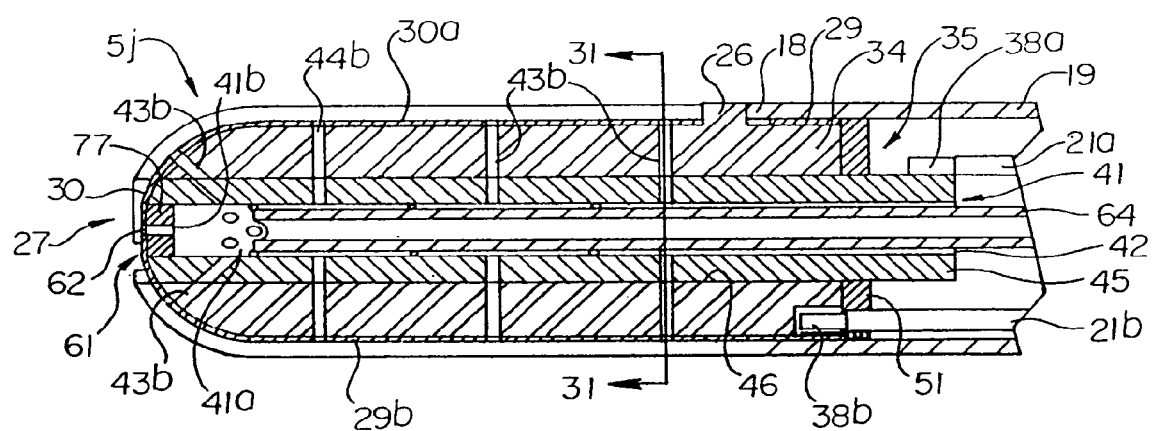
FIG. 30 is a schematic close-up cross-sectional view of the assembly of the electrosurgical device of FIG. 29 and tube 19 taken in accordance with line 12-12 of FIG. 13.
Figure 31:
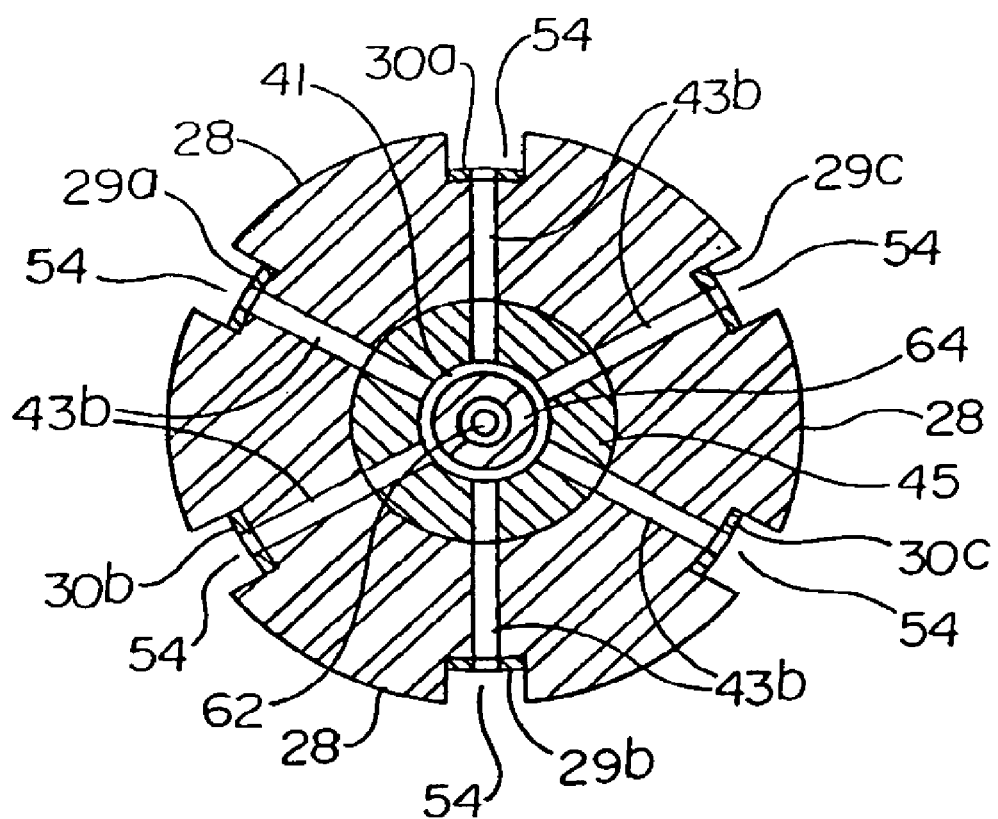
FIG. 31 is a schematic close-up cross-sectional view of the electrosurgical device of FIG. 29 taken in accordance with line 31-31 of FIG. 30.

Another exemplary electrosurgical device of the present invention which may be used in conjunction with the system of the present invention is shown at reference character 5j in FIG. 29, and more particularly in FIGS. 29-31. As best shown in FIG. 30, rather than an occlusion comprising wall section 25 of a liner 45 or a wall section 47 of conductor 30 defining at least a portion of the distal end of the central flow passage 41 as with earlier embodiments, the occlusion defining at least a portion of the distal end of the central flow passage 41 may comprise a wall section 77 of a separately formed plug 61.

As shown in FIG. 30, wall section 77 of plug 61 adjacent distal end 27 of the electrosurgical device 5j and probe body 26 partially defines the distal end of the wide proximal portion 41a of the central flow passage 41 (with the proximal end of the distal narrow portion 41b of the central flow passage 41 defining the remainder of the distal end of the wide portion 41a of the central flow passage 41 in this embodiment). Wall section 77 of plug 61 also narrows the central flow passage 41 from wide portion 41a to narrow portion 41b and defines a narrow central fluid passage exit opening 62. In the above manner, the wall section 77 inhibits fluid flow from wide portion 41a through the narrow portion 41b of the central flow passage 41. In other words, wall section 77 inhibits the amount of fluid 24 exiting from the central fluid passage exit opening 62 as compared to a situation where wall section 77 would not be used and the central flow passage 41 only would consist of wide portion 41a. In the above manner, at least a portion of the distal end of the central flow passage 41 is defined by an occlusion (i.e. wall section 77) formed by a portion of the electrosurgical device 5j.

As best shown in FIG. 30, plug 61 may occlude the distal portion of the liner 45 adjacent distal end 27 of the electrosurgical device 5j and probe body 26 by being at least partially contained within the liner 45 at the distal end 27 of the electrosurgical device 5j and probe body 26. Plug 61 may be fixed relative to probe body 26 and within liner 45 as a result of being mechanically connected, preferably interference fit (e.g. with compression of the plug 61) or otherwise fastened (e.g. adhesively bonded) against the wall surface 33 of the liner 45. Plug 61 preferably comprises an insulative deformable polymer material, such as a flexible elastomer and, in this embodiment, preferably comprises the geometry of a thin, flat, circular member.

As shown in FIG. 30, where central flow passage 41 continues through plug 61 and comprises narrowed portion 41b, narrowed portion 41b may also be configured for the passage an instrument 64 configured to treat tissue (e.g. injection needle, biopsy forceps, polypectomy snare). Preferably, in its nonuse or retracted position, as shown in FIG. 30, instrument 64 is contained within the wide portion 41a of the central flow passage 41 within probe body 26 and thereafter, with use, the instrument 64 is extended from the distal end 27 of the electrosurgical device 5j and probe body 26 when the instrument 64 is extended distally. The instrument 64 (shown as a hollow needle with an open, pointed tip) may be configured to penetrate tissue and enable injection therapy to tissue, such as the administration of a vasoconstrictor. sclerotic or topical anesthetic through the lumen of a needle.

Where instrument 64 comprises a hollow needle, preferably the needle extends proximally in the lumen of tube 45 and the lumen 23 of tube 19, towards the proximal end of tube 19 and exits the tube 19 through the sidewall thereof prior to the proximal end where it is then attached to an actuator assembly. Other instruments, such as the biopsy forceps, may be configured to retrieve tissue samples, such as for biopsy.

Figure 32:
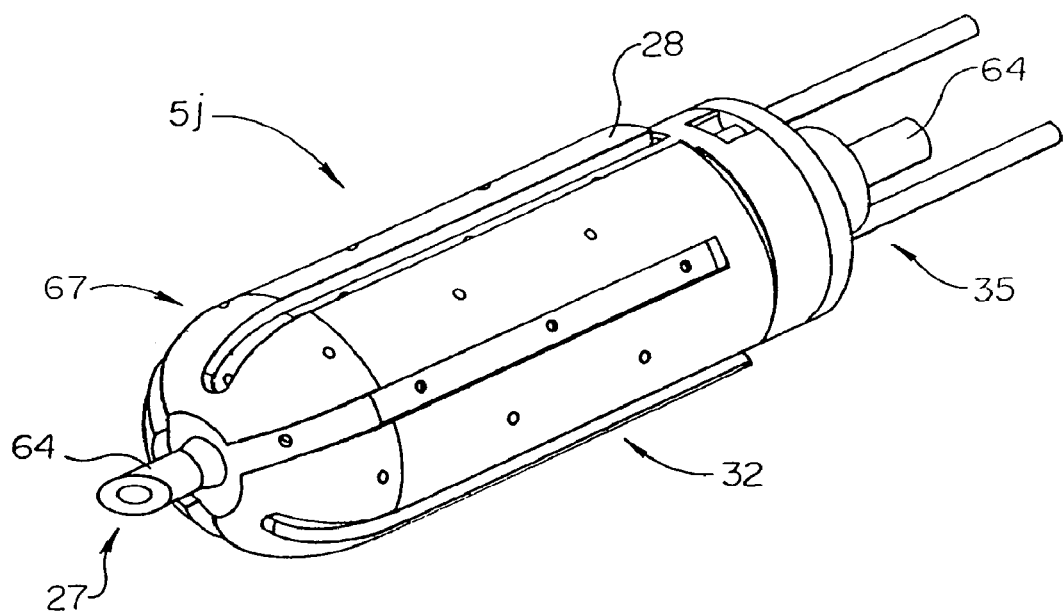
FIG. 32 is a schematic close-up front perspective view of the electrosurgical device of FIG. 29 with instrument 64 extended.
Figure 33:
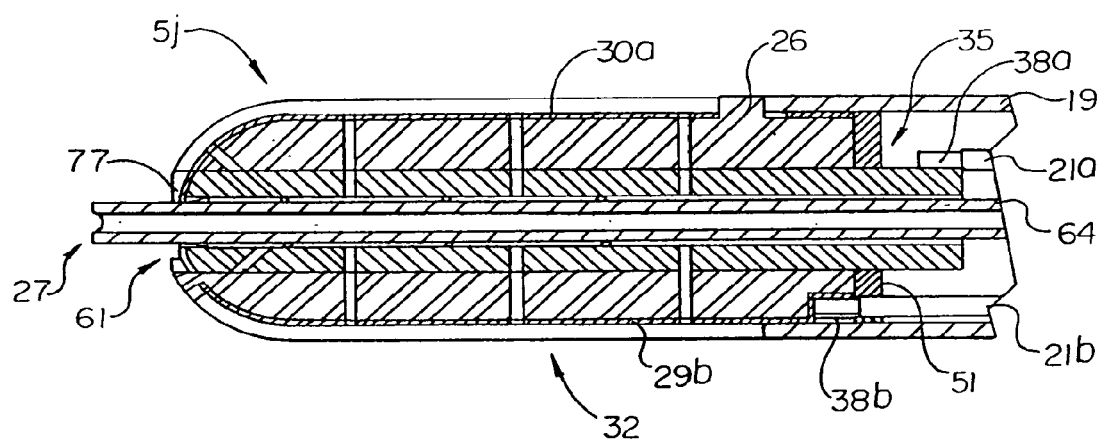
FIG. 33 is a schematic close-up cross-sectional view of the assembly of FIG. 30 with instrument 64 extended.

Referring to FIGS. 32 and 33, in order for instrument 64 to pass distally through the narrow portion 41b of central flow passage 41, depending on the relative size of the instrument 64 to the narrow portion 41b of central flow passage 41, wall section 77 plug 61 may be configured to deform to facilitate penetration of the plug 61 by the instrument 64 and, as a result, narrow portion 41b of central flow passage 41 may be configured to correspondingly increase its cross-sectional size of the through increasing diameter from a first cross-sectional area to a second cross-sectional-area. Furthermore, in order to inhibit the loss of fluid 24 through a narrow portion 41b of central flow passage 41 of increased size, a surface of the wall section 77 of the plug 61 may be configured to correspondingly at least partially seal narrow portion 41*b* and central fluid passage exit opening 62 against the outer wall surface of the instrument 64.

Conversely, once the instrument 64 is retracted proximally from plug 61, wall section 77 of plug 61 may be configured to return substantially to its pre-deformation configuration, and with the cross-sectional size of the narrow portion 41*b* of the central flow passage 41 returning substantially to its pre-deformation cross-sectional size.

Figure 34:
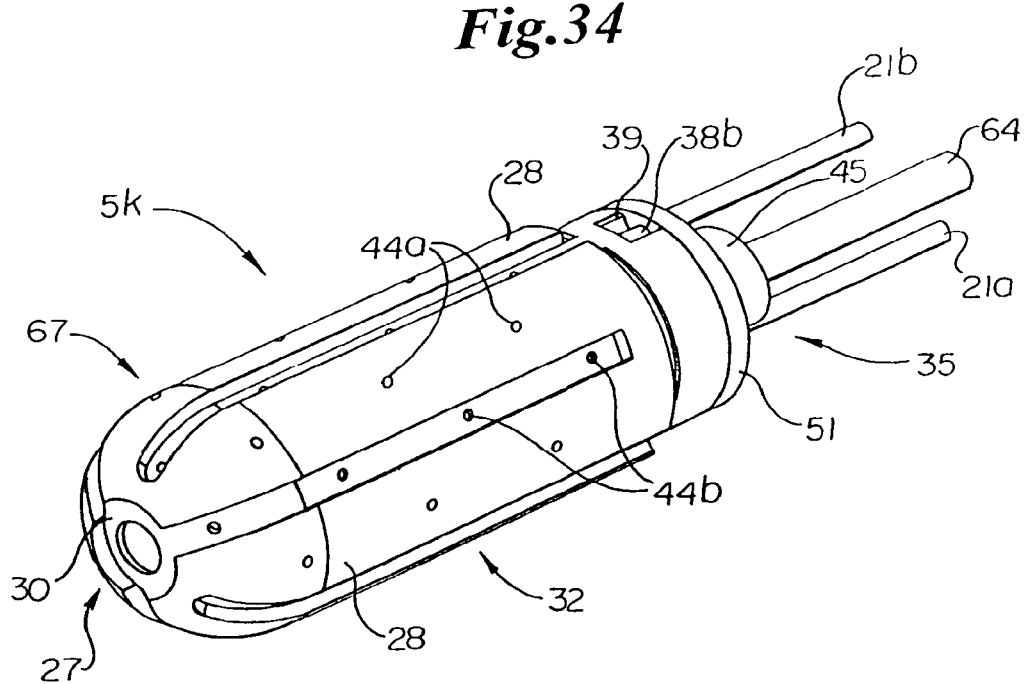
FIG. 34 is a schematic close-up front perspective view of an electrosurgical device according to another embodiment of the invention.
Figure 35:
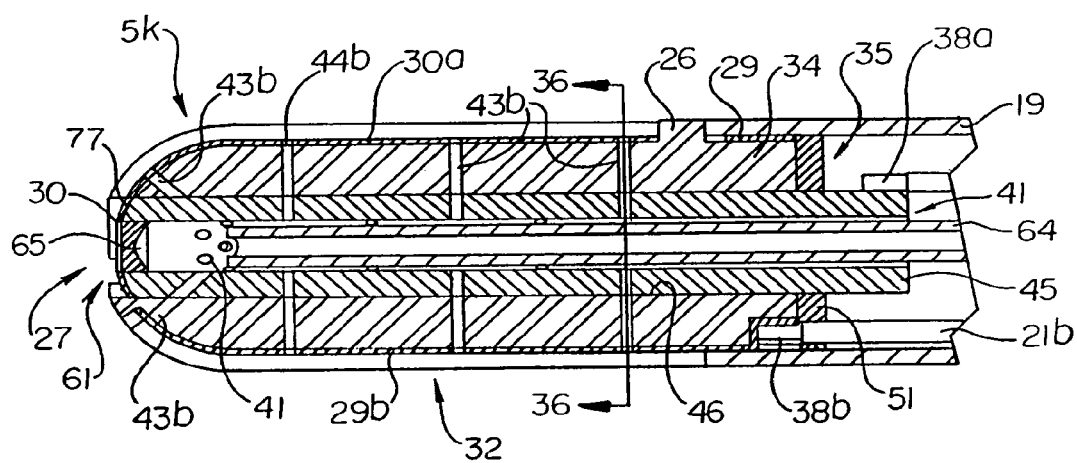
FIG. 35 is a schematic close-up cross-sectional view of the assembly of the electrosurgical device of FIG. 34 and tube 19 taken in accordance with line 12-12 of FIG. 13.
Figure 36:
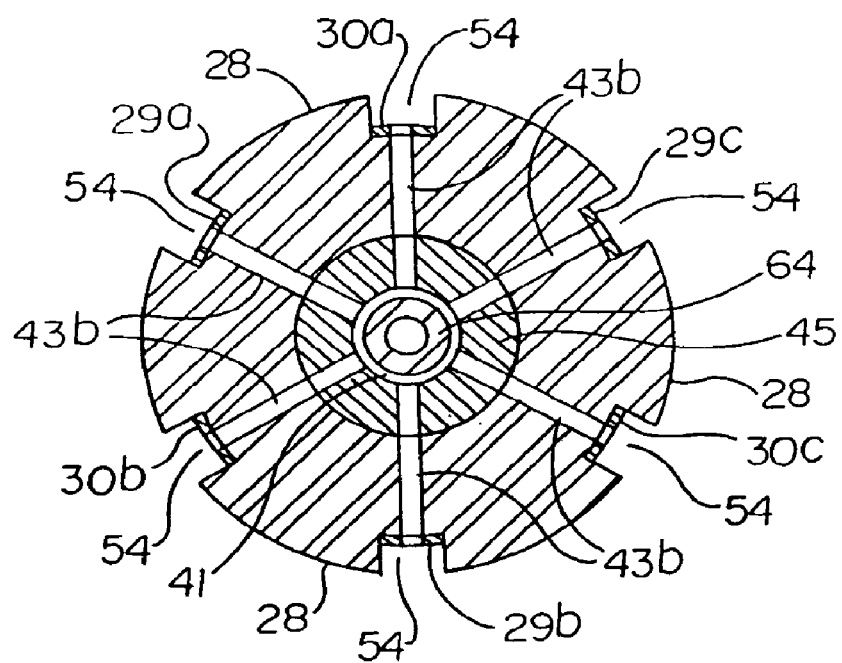
FIG. 36 is a schematic close-up cross-sectional view of the electrosurgical device of FIG. 34 taken in accordance with line 36-36 of FIG. 35.

Another exemplary electrosurgical device of the present invention which may be used in conjunction with the system of the present invention is shown at reference character 5*k* in FIG. 34, and more particularly in FIGS. 34-36. As best shown in FIG. 32, similar to embodiment 5*j*, rather than an occlusion comprising wall section 25 of a liner 45 or a wall section 47 of conductor 30 defining at least a portion of the distal end of the central flow passage 41 as with earlier embodiments, the occlusion defining at least a portion of the distal end of the central flow passage 41 may comprise a wall section 77 of a separately formed plug 61.

In contrast to embodiment 5*j*, rather than an occlusion formed by a portion of the electrosurgical device 5*k* defining at least a portion of the distal end of the central flow passage 41, an occlusion may completely define the distal end of the central flow passage 41. As shown in FIG. 32, wall section 77 of plug 61 completely defines the end of the central flow passage 41. In other words, central flow passage 41 only comprises wide portion 41*a* and does not comprise narrow portion 41*b* or a central fluid passage exit opening 62. In this manner, the central flow passage 41 is completely closed by a portion of the electrosurgical device structure forming the distal end of the central flow passage 41.

However, where central flow passage 41 does not continue through plug 61 as a pre-formed opening, an opening comprising narrow portion 41*b* and a central fluid passage exit opening 62 may be configured to be formed in plug 61 by the instrument 64 during extension of the instrument 64 through the plug 61. For example, plug 61 may be configured to be penetrated (e.g. pierced) by the instrument 64 when the instrument 64 extends distally to form an opening therein for the instrument 64 to extend and retract therethrough. Where the plug 61 is configured to be penetrated, the specific area of the plug 61 configured for penetration may include an area of mechanical weakness, such as an area of reduced thickness 65, to promote tearing and opening in a predetermined area. As shown, the area of reduced thickness 65 comprises a convex shaped recess formed in the proximal side of the plug 61.

Among other things, the configuration of electosurgical devices 5*j* and 5*k* provide that the devices may be used either simultaneously or independently with instrument 64. For example, once instrument 64, such as a hollow hypodermic needle with an open, pointed tip, penetrates plug 61 and extends distally from the distal end 27 of the electrosurgical devices 5*j* or 5*k*, as indicated above, a surface of the opening in the plug 61 penetrated by the needle, either formed prior or simultaneously with the use of the instrument 64, preferably seals against the perimeter outer wall surface of the needle to provide a gasket. At this time, electrical power and fluid used with electrosurgical devices 5*j* and 5*k* from lumen 23 of tube 19 and central and lateral fluid flow passages 41, 43 may be provided simultaneously to tissue with fluid from the lumen of instrument 64 (e.g. therapeutic hypodermic medication). Alternatively, when using the two functions independently, the electrical power to electrosurgical devices 5*j* and 5*k*, or both the electrical power and the conductive fluid to electrosurgical devices 5*j* and 5*k*, may be switched off when medication from instrument 64 is administered.

In addition, among other things, instrument 64 can function as an electrode extended distally from probe body 26. Where instrument 64 comprises an electrode, preferably the electrode comprises the same alternating electrical charge as electrodes 30*a-c* connected to conductor 30. An electrode which extends distally from probe body 26, such as instrument 64 is particularly useful to aid in treating tissue located distally end-on or oblique relative to probe body 26.

When instrument 64 comprises an electrode of the same alternating electrical charge as electrodes 30*a-c* connected to conductor 30, in addition to the electrical array which extends radially around longitudinal axis 31 between adjacent successive poles, an electrical array extends longitudinally between the instrument 64 comprising an electrode and electrodes 29*a-c*.

In other embodiments of the present invention, the instrument 64 comprising an electrode may alternatively be used in a monopolar configuration (without electrodes 29*a-c*, 30*a-c*) with the second electrode located on the patient being treated. In this embodiment, one of the wires going to the bipolar device would instead go to a ground pad dispersive electrode located on the patient's back or other suitable anatomical location.

Figure 37:
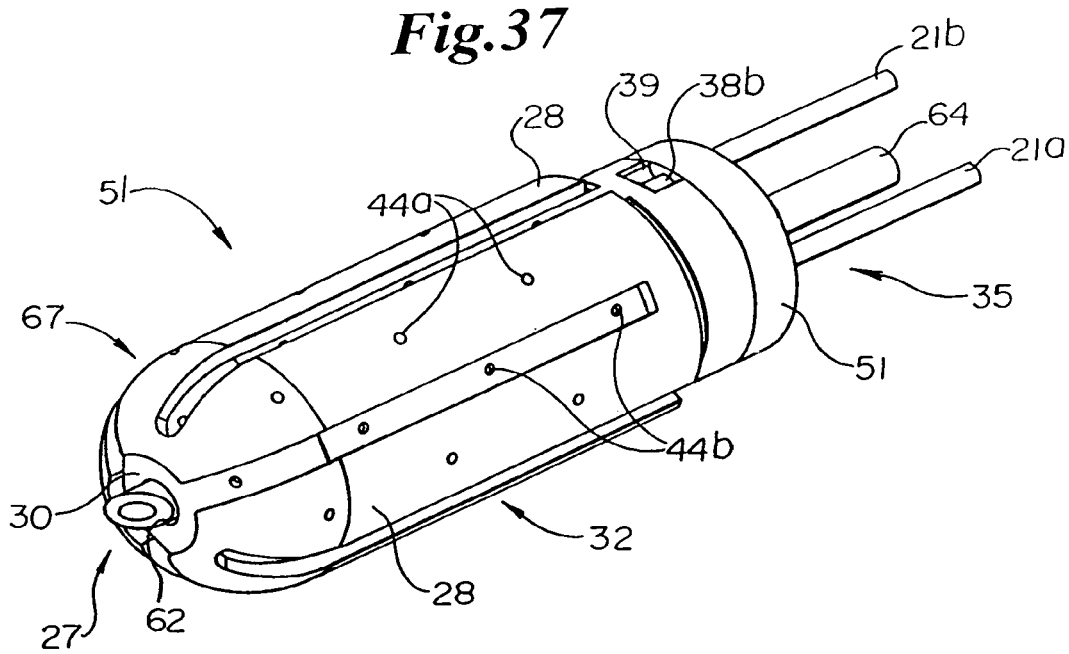
FIG. 37 is a schematic close-up front perspective view of an electrosurgical device according to another embodiment of the invention.
Figure 38:
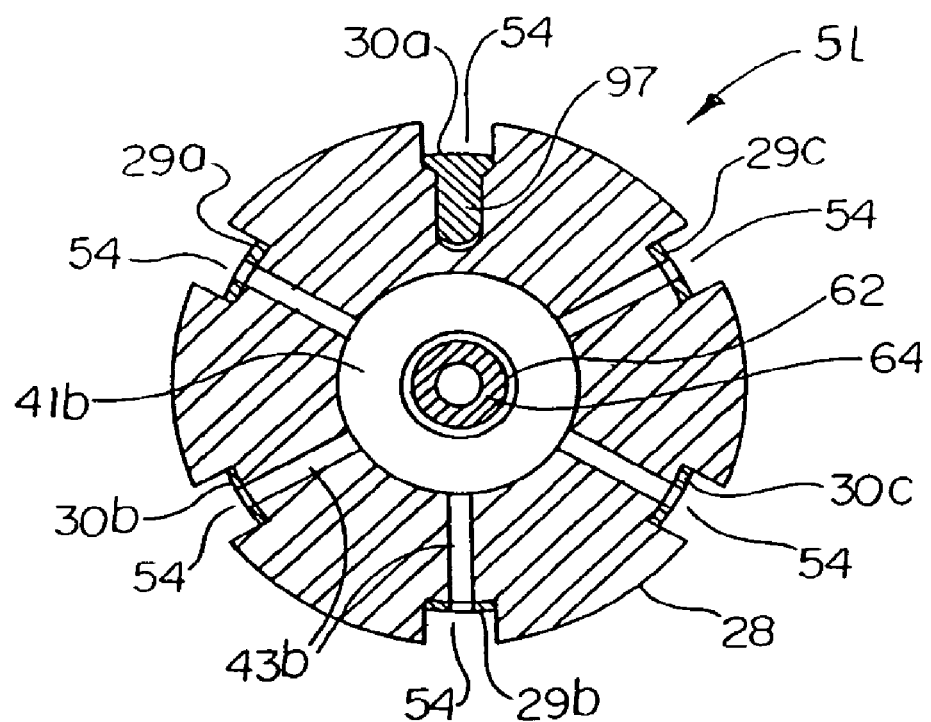
FIG. 38 is a schematic close-up cross-sectional view of the electrosurgical device of FIG. 37 taken in accordance with line 38-38 of FIG. 39.
Figure 39:
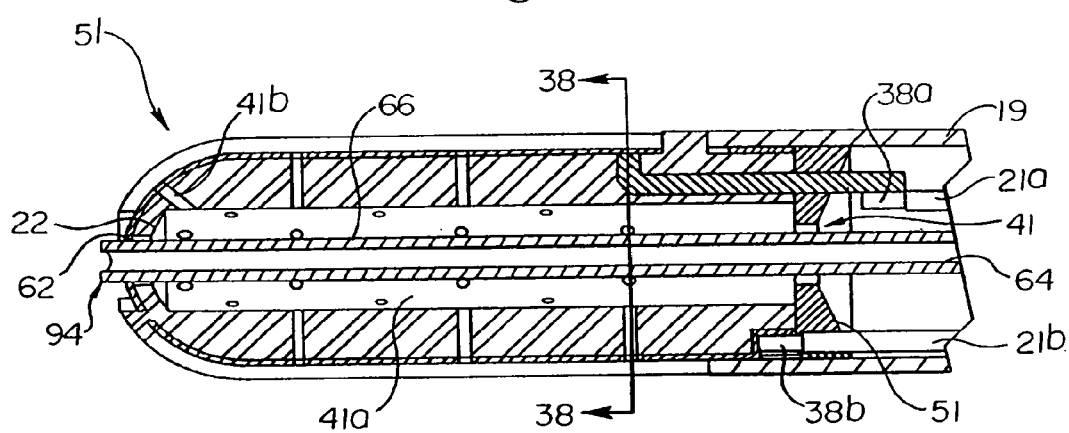
FIG. 39 is a schematic close-up cross-sectional view of the assembly of the electrosurgical device of FIG. 37 with instrument 64 and tube 19 taken in accordance with line 12-12 of FIG. 13.

Another exemplary electrosurgical device of the present invention which may be used in conjunction with the system of the present invention is shown at reference character 51 in FIG. 37, and more particularly in FIGS. 37-40. As best shown in FIG. 39, rather than an occlusion comprising wall section 25 of liner 45, or a wall section 47 of conductor 30 or a wall section 77 of plug 61 defining at least a portion of the distal end of the central flow passage 41 as with earlier embodiments, the occlusion defining at least a portion of the distal end of the central flow passage 41 may comprise a wall section 22 of the probe body 26. Also as shown in FIG. 36, liner 45 has been eliminated.

As shown in FIG. 39, distal wall section 22 of probe body 26 adjacent distal end 27 of the electrosurgical device 5*k* partially defines the distal end of the wide proximal portion 41*a* of the central flow passage 41. Distal wall section 22 of probe body 26 also narrows the central flow passage 41 from wide portion 41*a* to narrow portion 41*b* and defines a narrow central fluid passage exit opening 62. In the above manner, the distal wall section 22 inhibits fluid flow from wide portion 41*a* through the narrow portion 41*b* of the central flow passage 41. In other words, distal wall 22 inhibits the amount of fluid 24 exiting from the central fluid passage exit opening 62 as compared to a situation where distal wall 22 would not be used and the central flow passage 41 only would consist of wide portion 41*a*. In the above manner, at least a portion of the distal end of the central flow passage 41 is defined by an occlusion (i.e. wall section 22) formed by a portion of the electrosurgical device 51.

Similar to embodiments 5*j* and 5*k*, electrosurgical device 51 may be configured to receive and instrument 64 therein. As with embodiments 5*j* and 5*k*, instrument 64 may comprise a hollow hypodermic needle with an open, pointed tip, may be configured to treat tissue when extended distally from the distal end 27 of the electrosurgical device 51 and probe body 26. More specifically, the instrument 64 may be configured to penetrate tissue and provide injection therapy to tissue.

Also similar to embodiments 5*j* and 5*k*, instrument 64 is configured to pass distally through the narrow portion 41*b* of central flow passage 41 of device 51. Furthermore, similar to embodiment 5*j*, narrow portion 41*b* and central fluid passage exit opening 62 of device 51 is formed prior to the use of the instrument 64. However, unlike embodiments 5*j* and 5*k*, where a surface of narrow portion 41*b* of central flow passage 41 formed by wall section 77 of plug 61 preferably seals against the outer wall surface of the instrument 64, a surface of wall section 22 of probe 26 of device 51 does not seal against the outer side wall surface 66 of portion 94 of instrument 64. In this manner, fluid 24 may still exit from central fluid passage exit opening 62 during the use of instrument 64.

In order to enable the distal tissue treatment portion 94 of instrument 64 to pass through narrowed portion 41b of central flow passage 41 located at the distal end 27 of device 51, lateral narrow portion 41b of this exemplary embodiment preferably has a cross-sectional dimension (e.g. diameter) in the range between and including about 0.1 mm to 2 mm (to accommodate hypodermic needles in the range of 12 to 36 gauge) and more preferably has a diameter in the range between and including about 0.45 mm to 0.51 mm (to accommodate a hypodermic needle of 25 gauge).

Also similar to previous embodiments, the central flow passage 41 of device 51 is at least partially occluded distally by an occlusion. In other words, for example, in earlier embodiments the central flow passage 41 is at least partially occluded distally by wall section 25 of liner 45, wall section 77 of plug 61 or wall section 22 of probe body 26, with all three wall sections 25, 77 and 22 comprise a portion of their respective electrosurgical devices, Furthermore, all three wall sections form at least a portion of and define at least a portion of the distal end of the central flow passage 41.

Also similar to embodiments 5j and 5k, the narrow portion 41b of the central flow passage 41 of device 51 is occluded by an occlusion provided by a portion 94 of a separate instrument 64. However, as discussed above, for device 51, preferably fluid 24 may still exit from central fluid passage exit opening 62 during the use of instrument 64 while for devices 5i and 5j preferably it does not.

However, in distinct contrast from embodiments 5j and 5k, fluid 24 may be provided to device 51 from means other than lumen 23 of tube 19. Where instrument 64 comprises a hypodermic needle, preferably the electrosurgical function of device 51 is used independently of the function of instrument 64. With use, after instrument 64 has administered treated tissue, and its presence is no longer required, instrument 64 may be removed from the central flow passage 41 of electrosurgical device 51 by being withdrawn from electrosurgical device 51 proximally through lumen 23 of tube 19.

Figure 40:
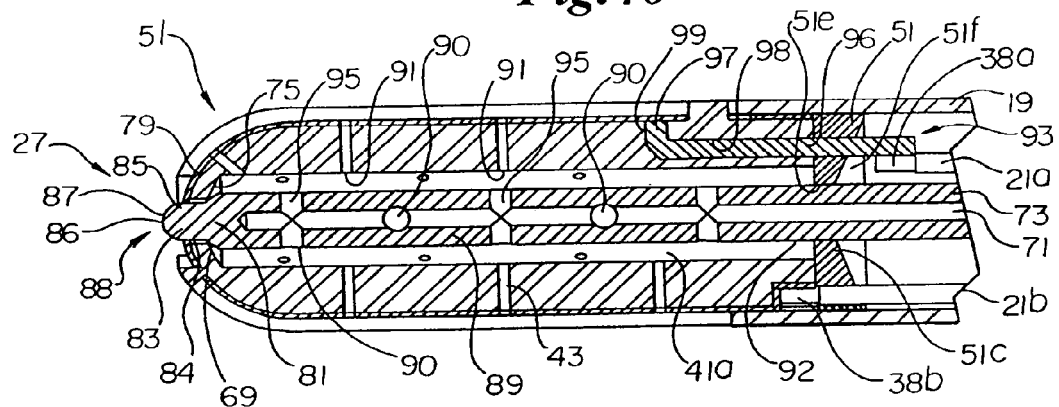
FIG. 40 is a schematic close-up cross-sectional view of the assembly of the electrosurgical device of FIG. 37 with instrument 73 and tube 19 taken in accordance with line 12-12 of FIG. 13.

After withdrawing instrument 64 from electrosurgical device 51, narrowed portion 41b of central flow passage 41 located at the distal end 27 of the device 51 may then be at least partially occluded by the distal portion 88 of a second instrument 73 inserted into electrosurgical device 51 through lumen 23 of tube 19. As shown in FIG. 40, second instrument 73 also comprises a hollow tube with a lumen therein.

Continuing with FIG. 40, preferably the distal portion of wide portion 41a comprises a narrowing transition portion over the length of which the cross-sectional dimension and area of the central flow channel 41 decreases from that of the wide portion 41a to that of narrow portion 41b. As shown, the diameter and corresponding cross-sectional area of wide portion 41a of central fluid flow passage 41 narrows to the diameter and corresponding cross-sectional area of narrowed portion 41b over the length of tapered portion 79 which, more particularly comprises a tapered concave conical surface 75. Returning to second instrument 73, the distal portion 88 preferably comprises at least one fluid flow restriction portion which is configured to occlude narrowed portion 41b of central flow passage 41 when second instrument 73 is used in conjunction with electrosurgical device 51, particularly probe body 26.

More particularly, as shown in FIG. 40, distal portion 88 of second instrument 73 comprises a fluid flow restriction portion 81 which, more particularly comprises a tapered convex conical surface 69. When instrument 73 is positioned for use, the surface 69 of tapered portion 81 of instrument 73 cooperates with the surface 75 of tapered portion 79 of probe body 26, preferably via at least partial contact, to at least partially occlude flow therebetween and the corresponding inhibit flow from central flow passage exit opening 62.

In addition to first flow restriction portion 81, the distal portion 88 of second instrument 73 preferably further comprises a second flow restriction portion 83 extending distally from fluid flow restriction portion 81 and configured to extend into narrowed portion 41b of central flow passage 41. As shown second flow restriction portion 83 comprises a cylindrical portion configured to restrict fluid flow through narrowed portion 41b when the outer surface 84 of the second flow restriction portion 83 cooperates, preferably via at least partial contact, with the wall surface 85 of narrowed portion 41b to at least partially occlude flow therebetween and the corresponding inhibit flow from central flow passage exit opening 62.

The distal portion 88 of second instrument 73 also preferably comprises a guide portion 86 which extends distally from second flow restriction portion 83. Guide portion 86 is preferably configured to guide the distal portion 88 of the second instrument 73 into the wide portion 41a of the central flow passage 41, but more particularly configured to guide the distal portion 88 of the second instrument 73 into narrowed portion 41b of the central flow passage 41. In addition, upon entering narrowed portion 41b, guide portion 86 is configured to position tapered portion 81 of second instrument 73 with tapered portion 79 of probe body 26 of electrosurgical device 17e in juxtaposed orientation relative to one another. As shown, preferably surface 69 of tapered portion 81 of second instrument 73 and surface 75 tapered portion 79 of probe body 26 comprise non-parallel surfaces such that the two surfaces, when in contact, contact and seal on a point.

As shown, guide portion 86 preferably comprises a generally cylindrical shape with the distal end 87 of the guide portion 86 preferably having a smooth, blunt contour surface, and preferably comprising a generally domed, hemispherical shape such as that of a semi-circle.

In addition to second instrument 73 comprising a guide portion 86, the tapered concave conical surface 75 of taper portion 79 of the probe body 26 also functions as a guide portion when it cooperates with guide portion 86 of second instrument 73 to guide the distal portion 88 of the second instrument 73 from the wide portion 41a of the central flow passage 41 into the narrowed portion 41b of central flow passage 41.

As shown in FIG. 40, in addition to the distal end 88 of the second instrument 73 preferably being occluded and providing for occluding narrowed portion 41b as outlined above, second instrument 73 also preferably comprises at least one fluid outlet passage 95 through the side wall 89 thereof. As shown, second instrument 73 comprises a plurality of fluid outlet passages 95 configured to provide fluid 24 to central flow passage 41 from lumen 71 of second instrument 73.

In order to inhibit the loss of fluid from central flow passage 41 to the lumen 23 of tube 19, preferably the proximal end of the central flow passage 41 of electrosurgical device 51 is also occluded such that central flow passage 41 preferably comprises a chamber. As shown in FIG. 40, the outer side wall surface 92 of the second instrument 73 cooperates, preferably via at least partial contact, with the sidewall surface portion 51e of member 51 to at least partially occlude flow and provide a seal therebetween and corresponding inhibit flow from central flow passage 41 back into lumen 23 of tube 19. More particularly, as shown in FIG. 40, gasket portion 51c which surrounds aperture 51d through which second instrument 73 extends to preferably form a gasket with the outer sidewall surface 92.

In order to guide instrument 64 or instrument 73 from the lumen 23 of tube 19 into central flow passage 41, preferably member 51 comprises a tapered portion 51f which, more particularly comprises a tapered concave conical surface.

Tapered portion 51*f* of member 51 particularly cooperates with guide portion 86 of second instrument 73 to guide the distal portion 88 of the second instrument 73 from the lumen 23 of tube 19 into the wide portion 41*a* of central flow passage 41.

In still other embodiments, the cross-sectional dimension (e.g. diameter) of the lumen 23 of tube 19 may be less than or equal to the cross-section dimension of the entrance opening to central flow passage 41 thus eliminating the need for tapered portion 51*f*.

In order to increase the uniformity of flow from central flow passage 41 to all the lateral fluid flow passages 43, preferably central flow passage 41 fills at least partially, and more preferably completely, with fluid 24 prior to expelling fluid 24 to the lateral fluid flow passages 43. Consequently, it may be desirable to inhibit fluid exiting fluid outlet passages 95 from entering any lateral fluid flow passages 43 directly as a result of the fluid exit openings 90 of fluid outlet passages 95 being aligned with the fluid entrance openings 91 of lateral fluid flow passages 43. Preferably when second instrument 73 is positioned for use, preferably the fluid exit openings 90 of fluid outlet passages 95 are at least partially offset (i.e. do not perfectly underlie) from the fluid entrance openings 91 of lateral fluid flow passages 43 such that at least a portion of the fluid provided from fluid outlet passages 95 must flow longitudinally prior to entering lateral fluid flow passages 43.

In the absence of liner 45 to conduct electricity to electrodes 30*a*-*c*, preferably electric connection between conductor 38*a* of wire 21*a* and electrodes 30*a*-*c* is preferably made via a conductor 93 which comprises a longitudinally directed portion 96 and a laterally directed portion 97 located with connected blind holes 98 and 99, respectively. Conductor 93 preferably comprises a wire conductor and is preferably connected at its proximal end to conductor 38*a* of wire 21*a* and at its distal end to one of the electrodes 30*a*-*c* joined by conductor 30.

Figure 41:
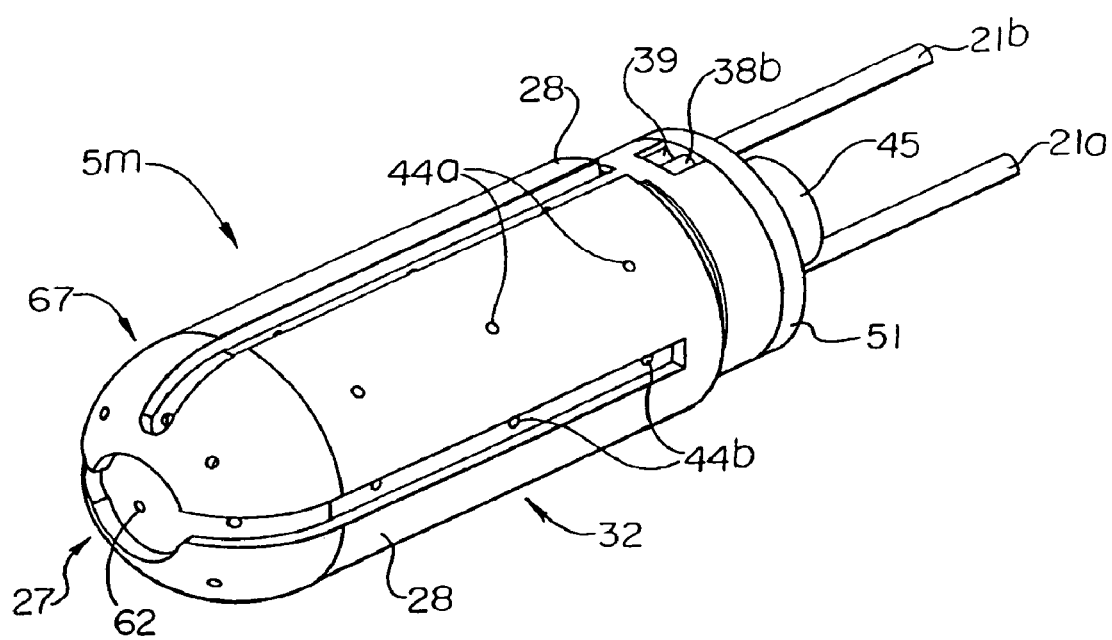
FIG. 41 is a schematic close-up front perspective view of an electrosurgical device according to another embodiment of the invention.
Figure 42:
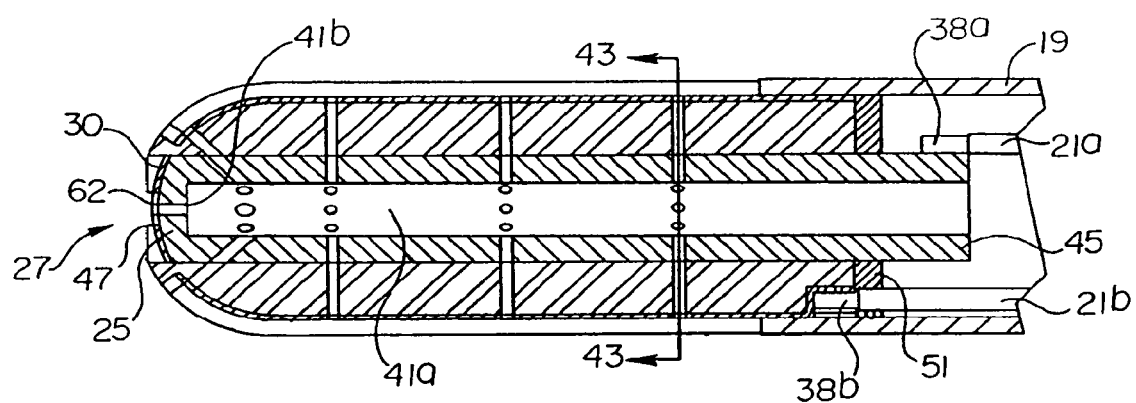
FIG. 42 is a schematic close-up cross-sectional view of the assembly of the electrosurgical device of FIG. 41 and tube 19 taken in accordance with line 12-12 of FIG. 13.
Figure 43:
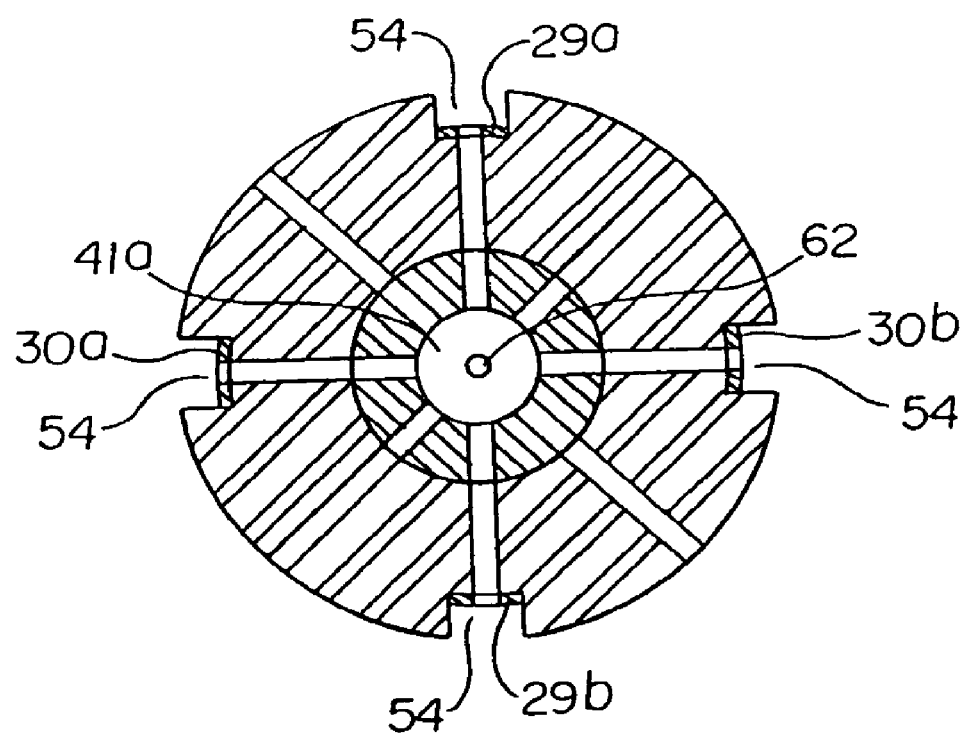
FIG. 43 is a schematic close-up cross-sectional view of the electrosurgical device of FIG. 42 taken in accordance with line 43-43 of FIG. 42.
Figure 44:
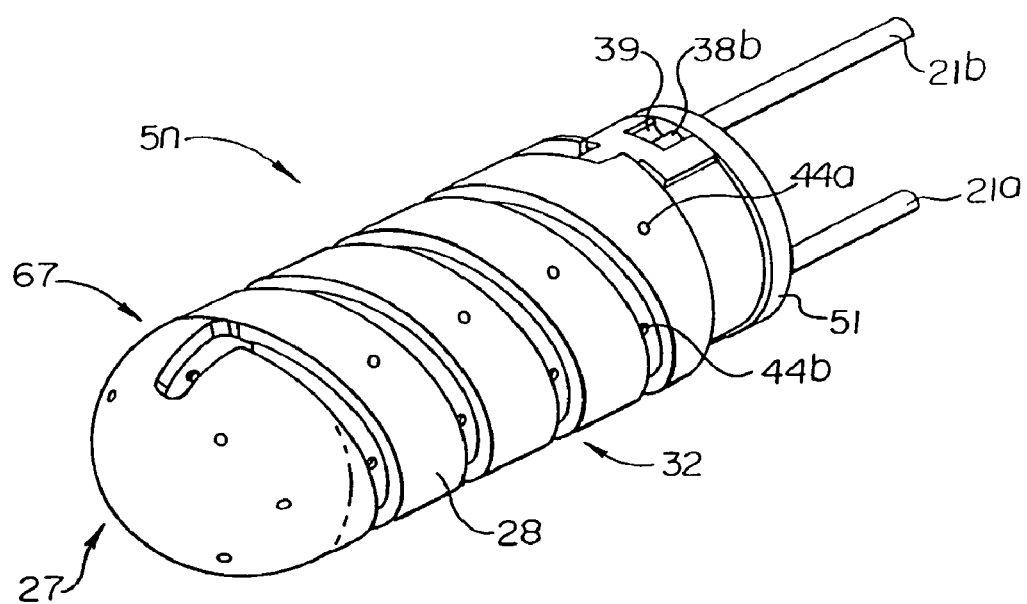
FIG. 44 is a schematic close-up front perspective view of an electrosurgical device according to another embodiment of the invention.
Figure 45:
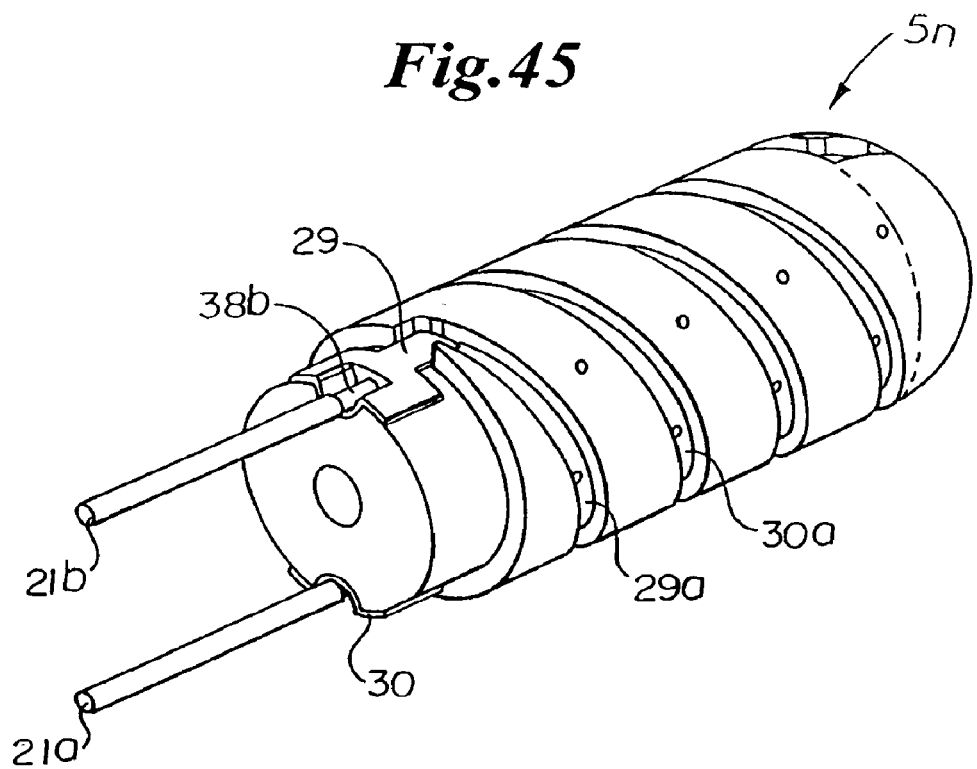
FIG. 45 is a schematic close-up rear perspective view of the electrosurgical device of FIG. 44 with member 51 removed.

In other embodiments of the invention, the electrosurgical device may comprise less or more than six electrodes. For example, as shown in FIGS. 41-43, for electrosurgical device 5*m* the conductors 29, 30 are preferably branched into sub-conductors with each comprising two elongated longitudinally directed strip electrodes 29*a*, 29*b*, and 30*a*, 30*b*, which will provide energy to treat tissue. As shown in FIGS. 41-42, the electrodes are preferably aligned generally parallel with the longitudinal axis 31 on the peripheral surface of the probe body 26 (comprising exposed probe body surfaces 28 and covered probe body surfaces 52) and are preferably angularly uniformly distributed, in this embodiment at angular intervals of 90 degrees.

Figure 46:
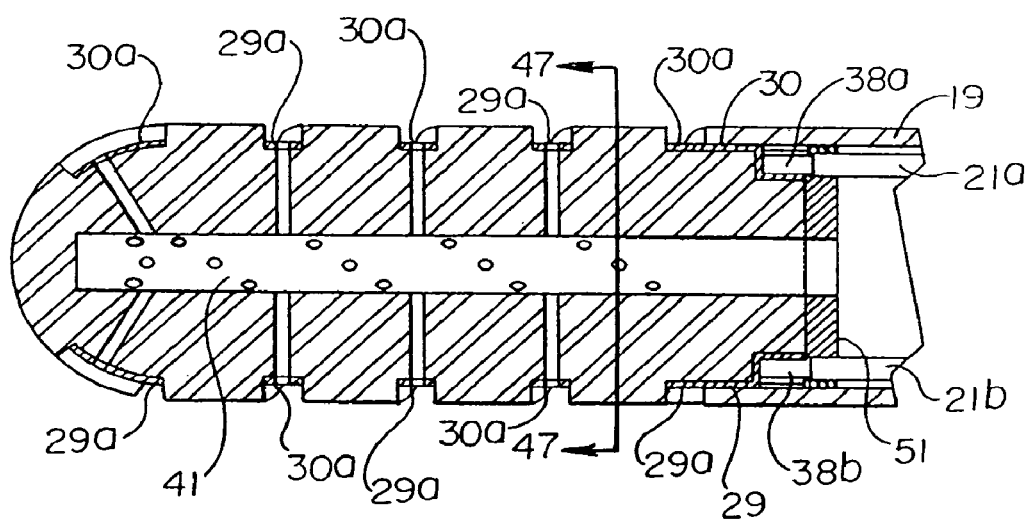
FIG. 46 is a schematic close-up cross-sectional view of the assembly of the electrosurgical device of FIG. 44 and tube 19 taken in accordance with line 12-12 of FIG. 13.
Figure 47:
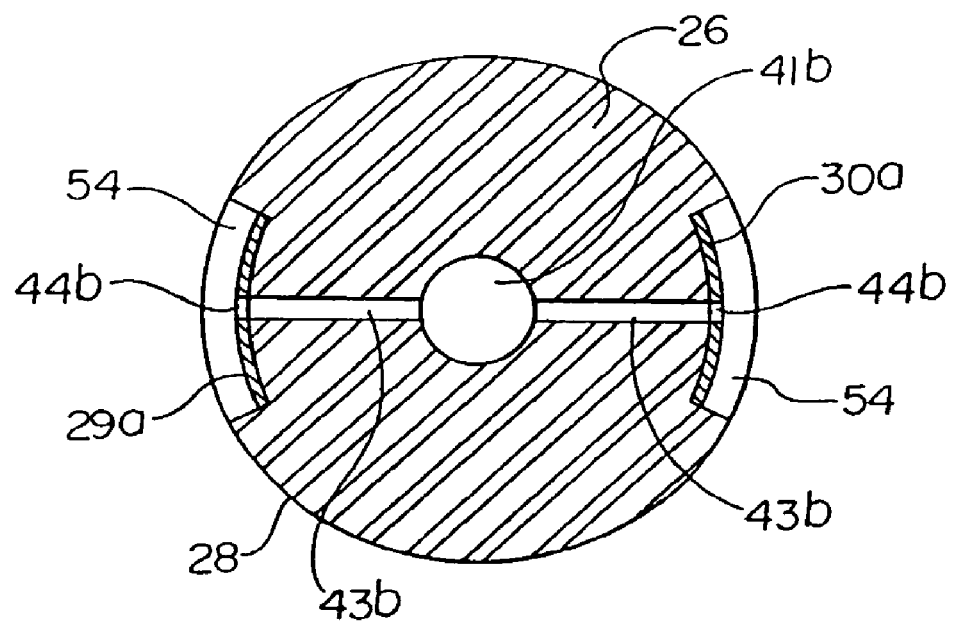
FIG. 47 is a schematic close-up cross-sectional view of the electrosurgical device of FIG. 44 taken in accordance with line 47-47 of FIG. 46.

In another embodiment of the invention as shown in FIGS. 44-47, for electrosurgical device 5*n* the conductors 29, 30 are not branched into an additional number of sub-conductors to provide energy to treat tissue, but rather the strip electrodes 29*a*, 29*b* are circumferentially directed and extend around the perimeter of the probe body 26 in a spiral configuration. In other words, as the circumferentially directed electrodes for device 5*n* extend around the perimeter of the probe body 26 they also simultaneously advance longitudinally on the probe body 26. Also as shown in FIG. 46, liner 45 has been eliminated, as well as narrow portion 41*b* of central flow passage 41 and central flow passage exit opening 62.

Figure 48:
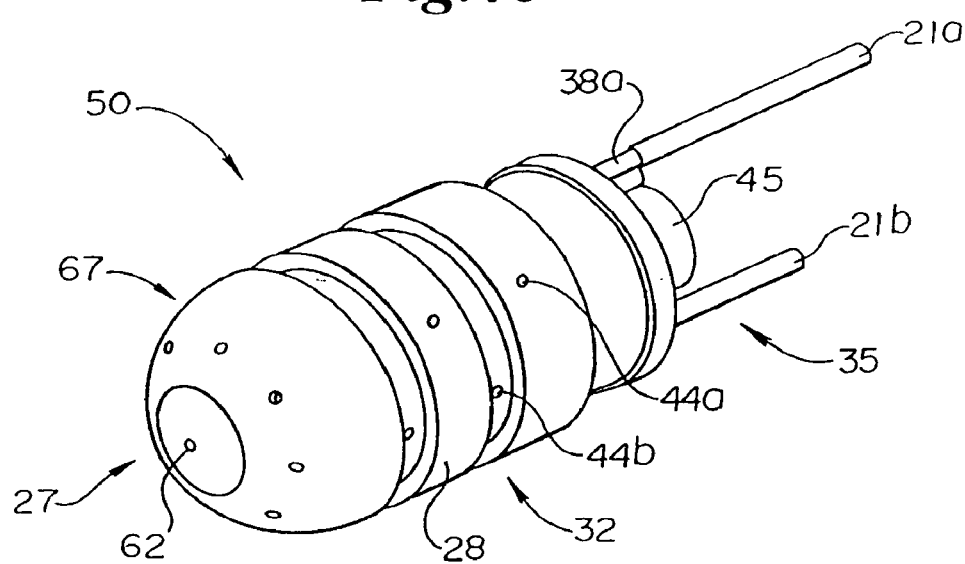
FIG. 48 is a schematic close-up front perspective view of an electrosurgical device according to another embodiment of the invention.
Figure 49:
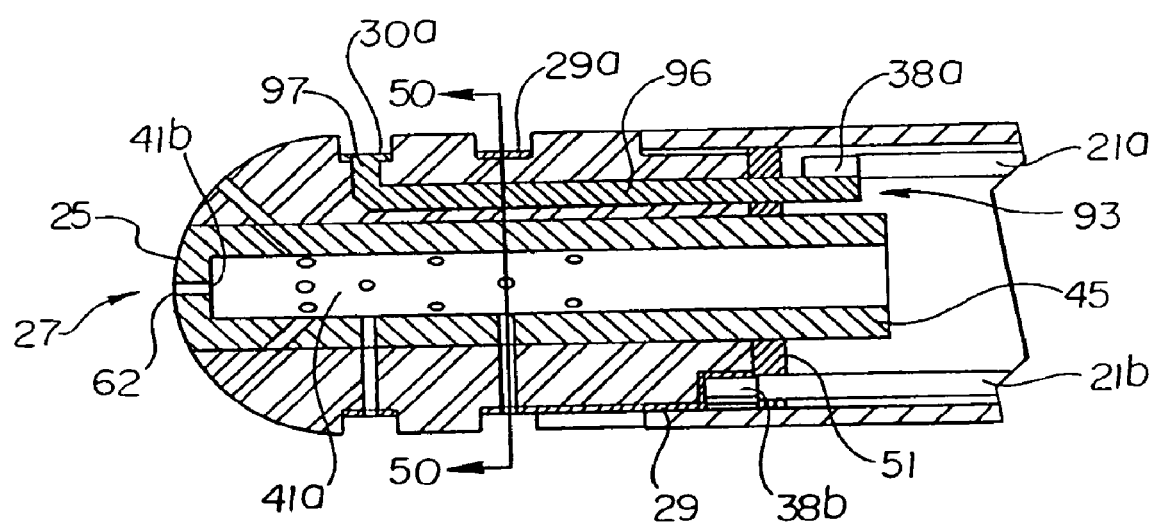
FIG. 49 is a schematic close-up cross-sectional view of the assembly of the electrosurgical device of FIG. 48 and tube 19 taken in accordance with line 12-12 of FIG. 13.
Figure 50:
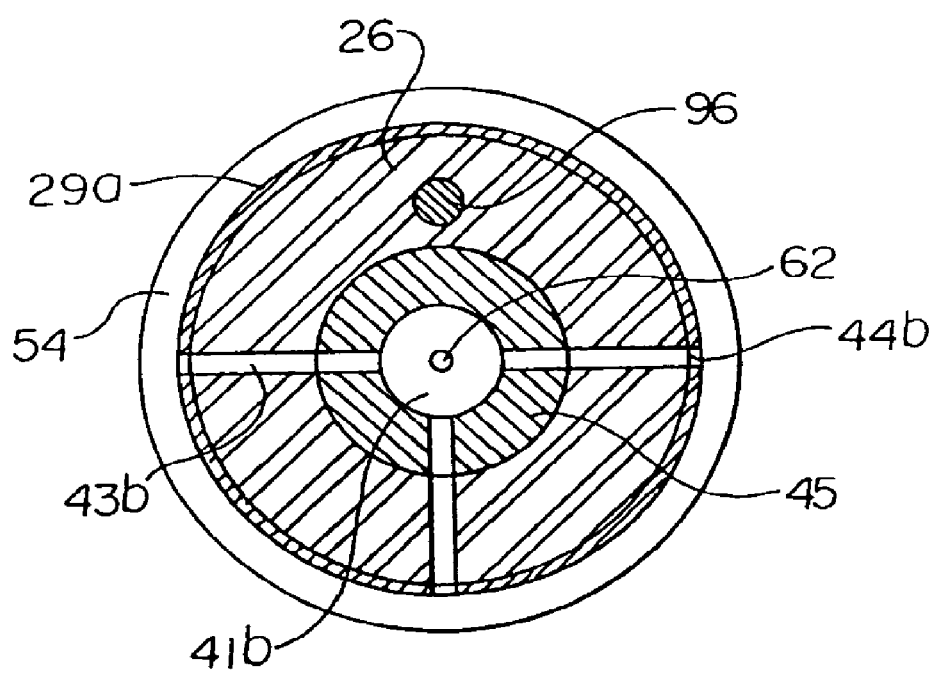
FIG. 50 is a schematic close-up cross-sectional view of the electrosurgical device of FIG. 48 taken in accordance with line 50-50 of FIG. 49.

In another embodiment of the invention as shown in FIGS. 48-50, similar to embodiment 5*n*, for electrosurgical device 5*o* the conductors 29, 30 are not branched into an additional number of sub-conductors to provide energy to treat tissue. However, rather the strip electrodes 29*a*, 29*b* circumferentially directed and extending around the circumference of the probe body 26 in a spiral configuration, electrodes 29*a*, 29*b* of embodiment 5*o* are circumferentially directed and extending around the perimeter of the probe body 26 in a closed circular hoop configuration. In other words, as the circumferentially directed electrodes for device 5*o* extend around the perimeter of the probe body 26 they do not advance longitudinally on the probe body 26.

Figure 51:
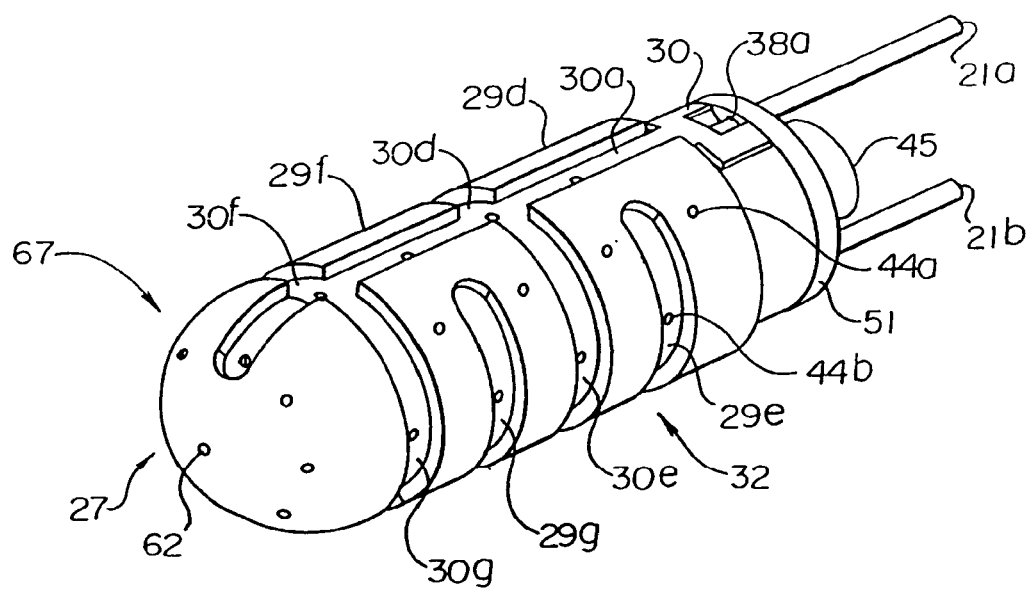
FIG. 51 is a schematic close-up front perspective view of an electrosurgical device according to another embodiment of the invention.
Figure 52:
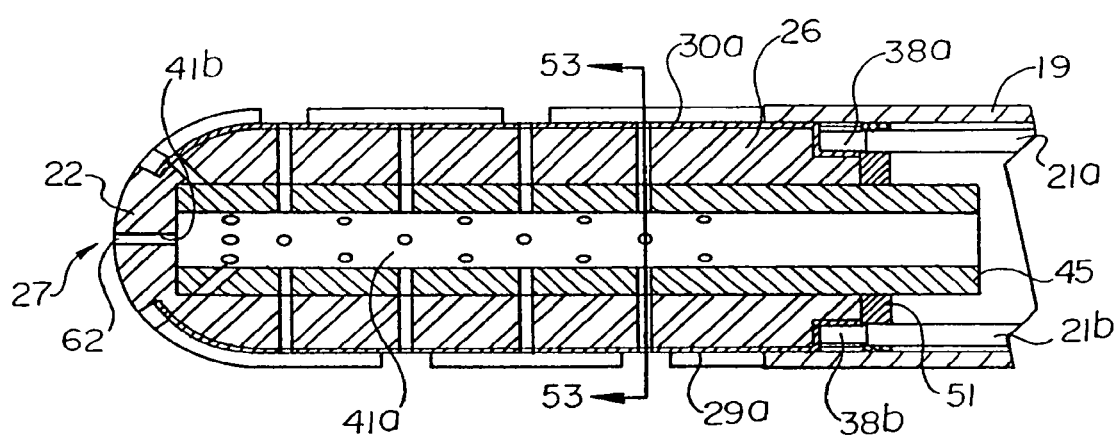
FIG. 52 is a schematic close-up cross-sectional view of the assembly of the electrosurgical device of FIG. 51 and tube 19 taken in accordance with line 12-12 of FIG. 13.
Figure 53:
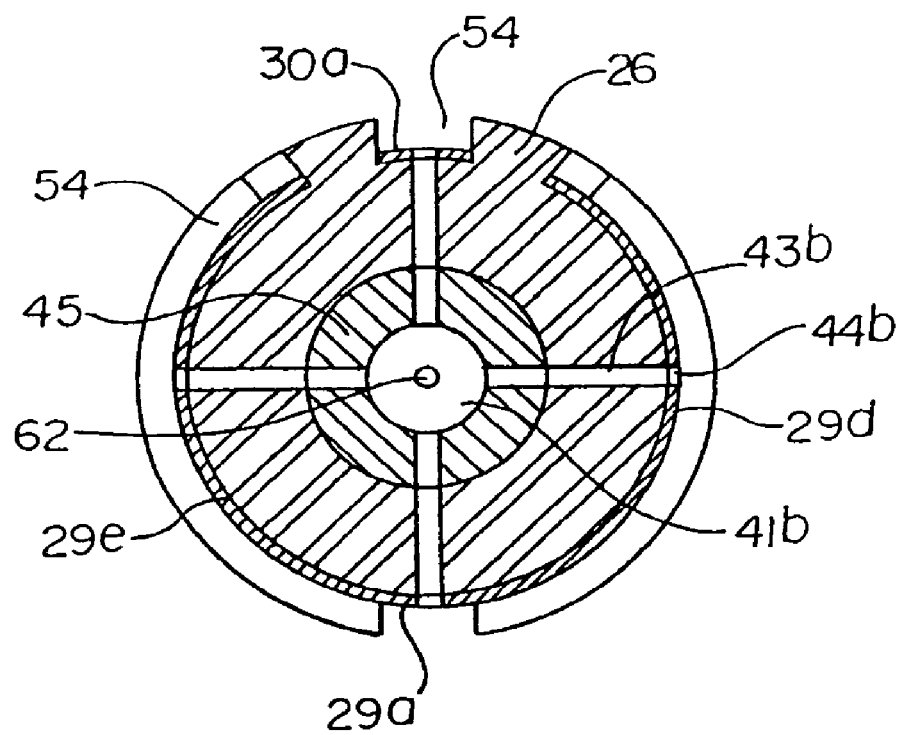
FIG. 53 is a schematic close-up cross-sectional view of the electrosurgical device of FIG. 51 taken in accordance with line 53-53 of FIG. 52.

In another embodiment of the invention as shown for device 5*p* in FIGS. 51-53, the electrode configuration comprises a combination of longitudinally directed electrodes and circumferentially directed electrodes. Furthermore, section 25 has been eliminated from liner 45.

As shown in FIGS. 51-53, longitudinally directed electrodes 29*a*, 30*a* are used in combination with circumferentially directed electrodes 29*d*-29*g* and 30*d*-30*g*, respectively. More particularly electrodes 29*d*-29*g* and 30*d*-30*g* comprise a partial or open circular hoop configuration. As shown each circular hoop configuration comprises a circular length corresponding to about 140 degrees around longitudinal axis 31. However, the circular hoop configuration may comprise a circular length corresponding to about 10 degrees to 170 degrees around longitudinal axis 31. Preferably the circular hoop configuration comprise a circular length corresponding to at least 80 degrees around longitudinal axis 31. Also as shown, electrodes 29*d*-29*g* and 30*d*-30*g* extend from electrodes 29*a*, 29*b* at substantially at right angle and on the outer tissue interacting surfaces 28 of the electrosurgical device 5*p* and terminate prior to intersection with the opposite longitudinally directed electrode.

Also as shown, preferably the circumferentially directed electrodes extend circumferentially around the probe body 26 from both opposing longitudinal sides of a longitudinally directed electrode. Furthermore, preferably the circumferentially directed electrodes on each side of the longitudinally directed electrode are aligned along the longitudinal length of the longitudinal electrode. For example, electrodes 30*d* and 30*e* extend circumferentially around the probe body 26 from both opposing longitudinal sides of a longitudinally directed electrode 30*a*. Furthermore, electrodes 30*d* and 30*e* are aligned along the longitudinal length of longitudinal electrode 30*a*.

In the above manner, preferably a single circular hoop configuration comprising a circular length double to the circular length of electrodes 30*d* and 30*e* individually is formed. In other words, the circular length of electrodes 30*d* and 30*e* combined corresponds to about 300 degrees around longitudinal axis 31 is formed. However, circular hoop configuration may comprise a circular length corresponding to about 20 degrees to 340 degrees around longitudinal axis 31. Preferably the circular hoop configuration comprise a circular length corresponding to at least 160 degrees around longitudinal axis 31.

Figure 54:
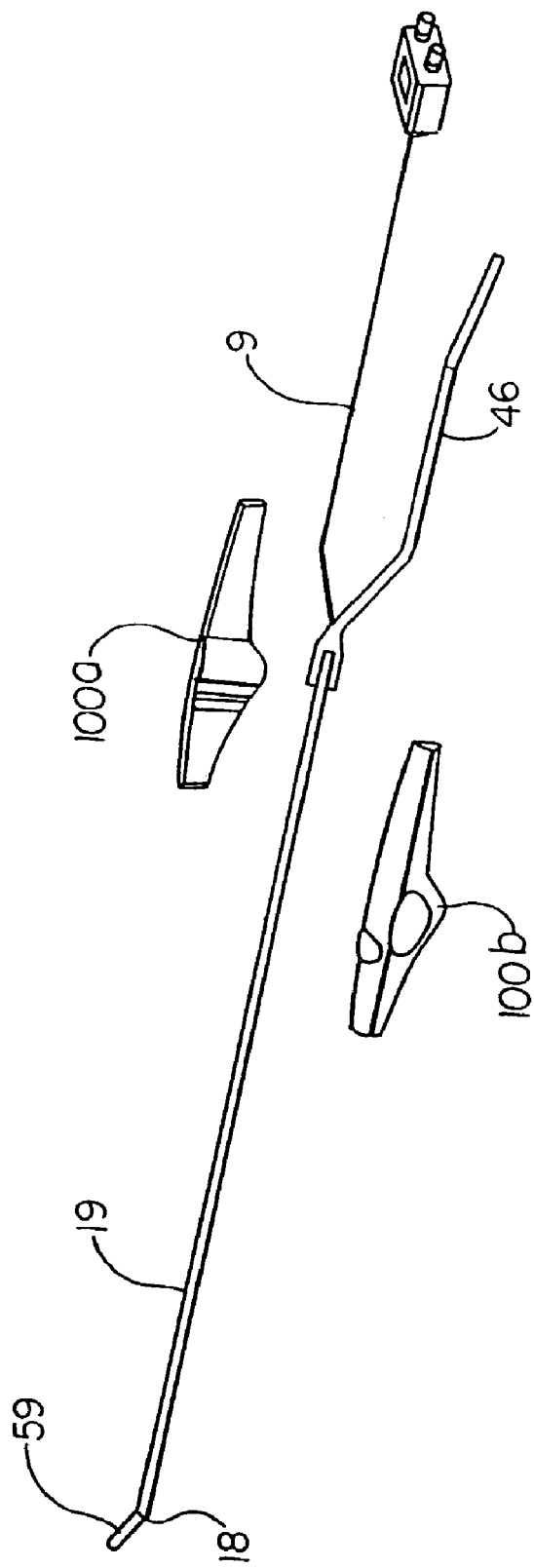
FIG. 54 is a schematic exploded perspective view of an assembly of an electrosurgical device according to another embodiment of the invention and a handle 100.

In contrast to the earlier disclosed embodiments, as shown in FIG. 54, electrosurgical device 5*q* is connected adjacent the distal end 18 of a rigid, self-supporting, hollow tube 19 (as opposed to the flexible tube of earlier disclosed embodiments) which form a shaft. Device 5*q* may comprise any of the electrosurgical devices (e.g. 5*a*-5*p*) disclosed herein. Also, as shown in FIG. 54, tube 19 is in turn connected to a proximal handle, preferably comprising two mating portions 100*a*, 100*b*. Handle 100*a*, 100*b* is preferably made of a sterilizable, rigid, and non-conductive material, such as a polymer (e.g. polycarbonate).

As with the other electrosurgical devices described within, a input fluid line 4*b* and a power source, preferably comprising generator 6 preferably providing RF power via cable 9, are preferably fluidly and electrically coupled, respectively, to the electrosurgical device 5*q*.

With respect to the fluid coupling, fluid 24 from the fluid source 1 for use with electrosurgical device 5*q* preferably is communicated from fluid source 1 through a flexible, polyvinylchloride (PVC) outlet fluid line 4*a* to a flexible, polyvinylchloride (PVC) inlet fluid line 4*b* connected to the electrosurgical device 5*q*. The outlet fluid line 4 and the inlet fluid line are preferably connected via a male and female mechanical fastener configuration, preferably comprising a Luer-Lok® connection from Becton, Dickinson and Company. The lumen of the inlet line is then preferably interference fit over the outside diameter of the tube 19 to provide a press fit seal there between. Additionally an adhesive may be disposed there between to strengthen the seal. Fluid is then communicated down the lumen 23 of the tube 19.

With respect to the electrical coupling, electrosurgical device 5*q* is preferably connected to the conductors 38*a*, 38*b* of insulated electrical wires 21*a*, 21*b*, respectively, which have been passed through lumen 23 of tube 19 after being spliced into the lumen of the polyvinylchloride (PVC) inlet fluid line as branches from cable 9 which is connected to generator 6.

As shown in FIG. 54, preferably the longitudinal axis 31 of electrosurgical device 5*q* is preferably configured at an angle relative to the longitudinal axis of tube 19. Preferably the longitudinal axis 31 of electrosurgical device 5*q* is configured at an angle of about 5 degrees to 90 degrees relative to the longitudinal axis of tube 19. More preferably, the longitudinal axis 31 of electrosurgical device 5*q* is configured at an angle of about 8 degrees to 45 degrees relative to the longitudinal axis of tube 19.

Figure 55:
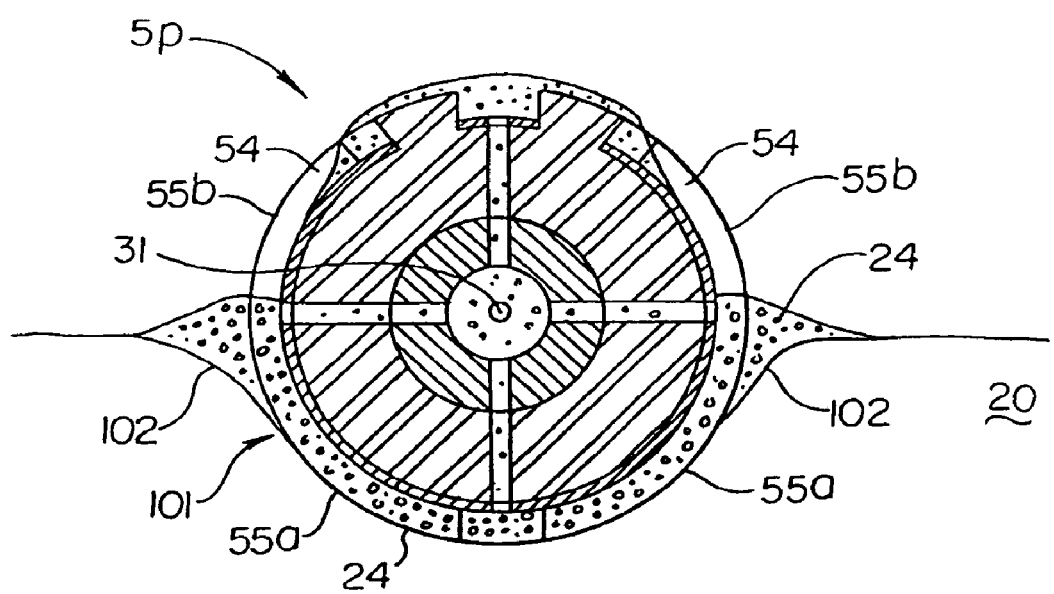
FIG. 55 is the schematic close-up up cross-sectional view of FIG. 53 shown with tissue 20 and with fluid 24.

In light of embodiments 5*a*-5*q*, the preferred electrosurgical device of the present invention may vary with application and use. For example, embodiments of devices with circumferentially directed fluid flow channels (e.g. 5*n*-5*p*) are generally preferred over embodiments predominately comprising longitudinally directed fluid flow channels (e.g. 5*a*-5*m*) when the longitudinal axis 31 of the devices are used in a substantially horizontal orientation. As shown in FIG. 55, device 5*p* is being used in a substantially horizontal orientation with cylindrical portion 32 the device 5*p* shown adjacent tissue 20 in a semi-circular tissue well 101, as shown encompassing about 180 degrees of the electrosurgical device 5*p*. However, in other embodiments, the semi-circular tissue well 101 may encompass more or less than 180 degrees of the electrosurgical device.

As shown in FIG. 55, a thin film of fluid 24 is provided from electrosurgical device 5*p* and exists between electrosurgical device 5*p* and tissue surface 102 near the bottom of well 101. However, tissue 20 overlies and occludes the portion 55*a* of the opening 55 of fluid flow channel 54 located within the well 101 adjacent tissue 20, while the fluid flow channel 54 itself remains unoccluded. Consequently, while tissue 20 inhibits fluid 24 from exiting fluid flow channel 54, it does not prevent fluid 24 in channel 54 from flowing within the confines of the channel 54. Thus, as the fluid flow channel 54 and opening 55 extend circumferentially around electrosurgical device 5*p*, with the portion 55*b* becoming unoccluded as the opening 55 emerges from well 100 and is no longer adjacent tissue 20, fluid 24 may then exit the fluid flow channel 54 at the tissue surface 102 adjacent the well 101.

Figure 56:
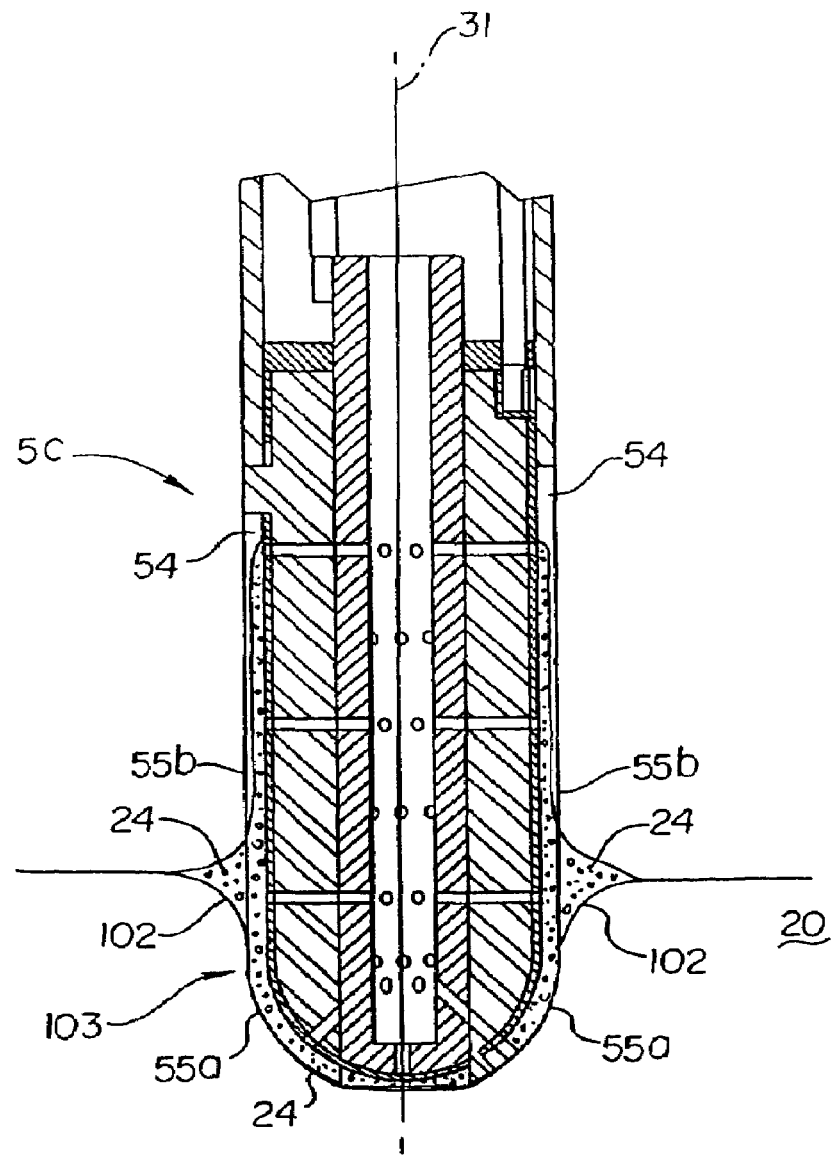
FIG. 56 is the schematic close-up up cross-sectional view of FIG. 21 shown with tissue 20 and with fluid 24.

Conversely, embodiments of devices with longitudinally directed fluid flow channels (e.g. 5*a*-5*m*) are generally preferred over embodiments predominately comprising circumferentially directed fluid flow channels (e.g. 5*o*) when the longitudinal axis 31 of the devices are used in a substantially vertical orientation. As shown in FIG. 56, device 5*c* is being used in a substantially vertical orientation with cylindrical portion 32 the device 5*c* shown adjacent tissue 20 in circular tissue well 102.

As shown in FIG. 56, tissue 20 overlies and occludes the portion 55*a* of the opening 55 of fluid flow channel 54 located within the circular well 103 adjacent tissue 20, while the fluid flow channel 54 itself remains unoccluded. Consequently, while tissue 20 inhibits fluid from exiting fluid flow channel 54, it does not prevent fluid 24 in channel 54 from flowing within the confines of the channel 54. Thus, as the fluid flow channel 54 and opening 55 extend circumferentially around electrosurgical device 5*c*, with the portion 55*b* becoming unoccluded as the opening 55 emerges from well 103 and is no longer adjacent tissue 20, fluid 24 may then exit the fluid flow channel 54 at the tissue surface 104 adjacent the well 103.

Recognizing that the electrosurgical devices of the present invention will potentially be used in both horizontal orientations and vertical orientations, as well as any orientation in between, during their use, the electrosurgical devices of embodiments 5*n* and 5*p* may be preferable to certain of the other embodiments disclosed herein.

Figure 57:
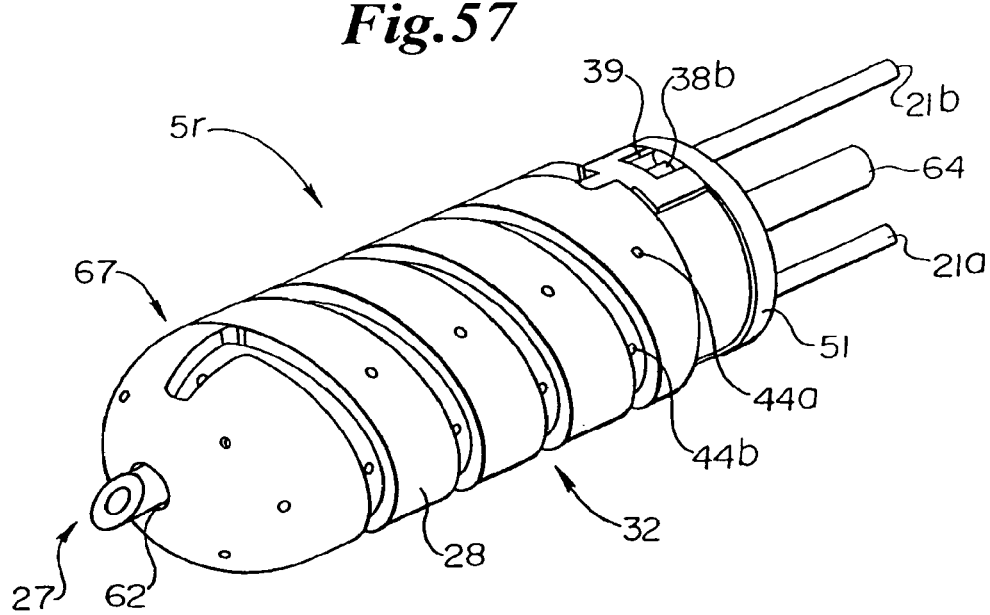
FIG. 57 is a schematic close-up front perspective view of an electrosurgical device according to another embodiment of the invention.
Figure 58:
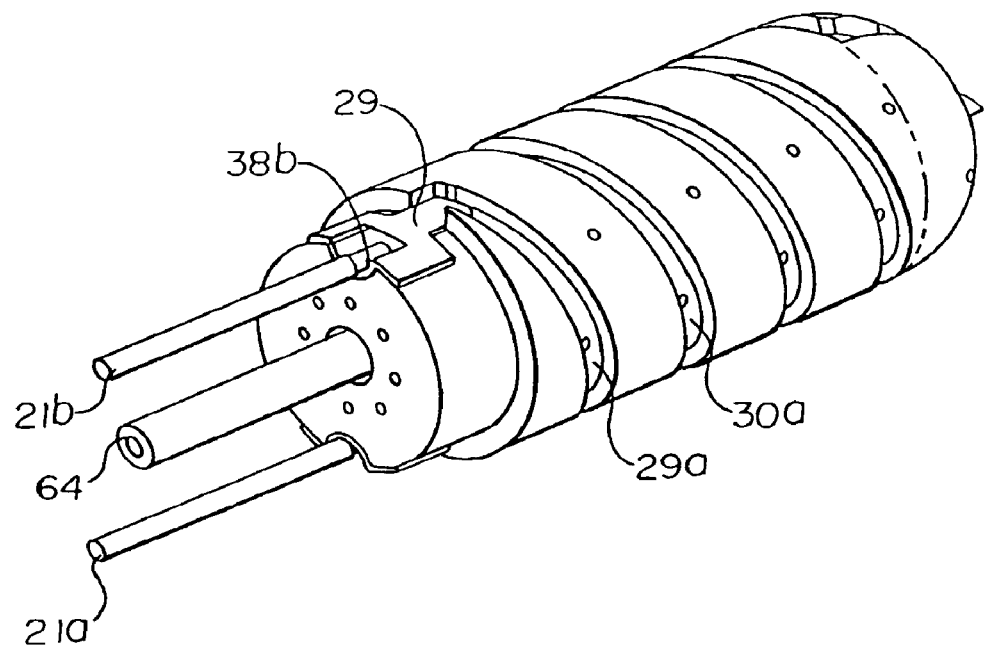
FIG. 58 is a schematic close-up rear perspective view of the electrosurgical device of FIG. 57 with member 51 removed.
Figure 59:
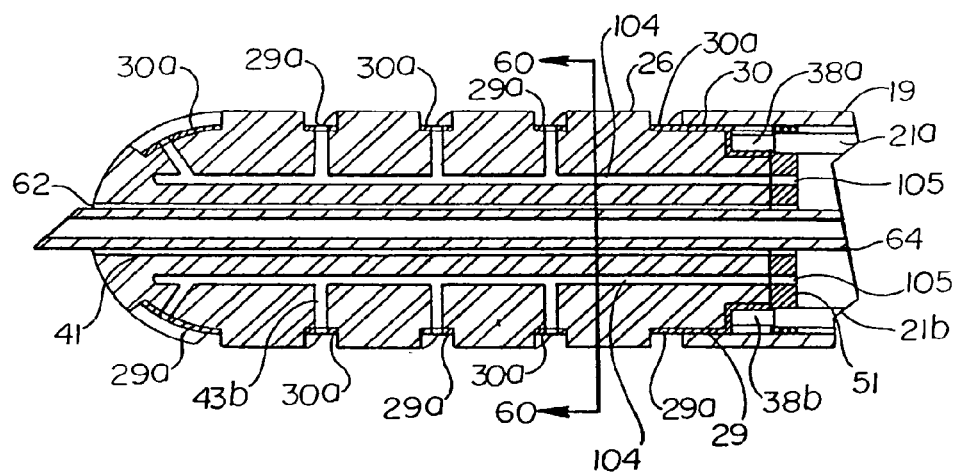
FIG. 59 is a schematic close-up cross-sectional view of the assembly of the electrosurgical device of FIG. 57 and tube 19 taken in accordance with line 12-12 of FIG. 13.
Figure 60:
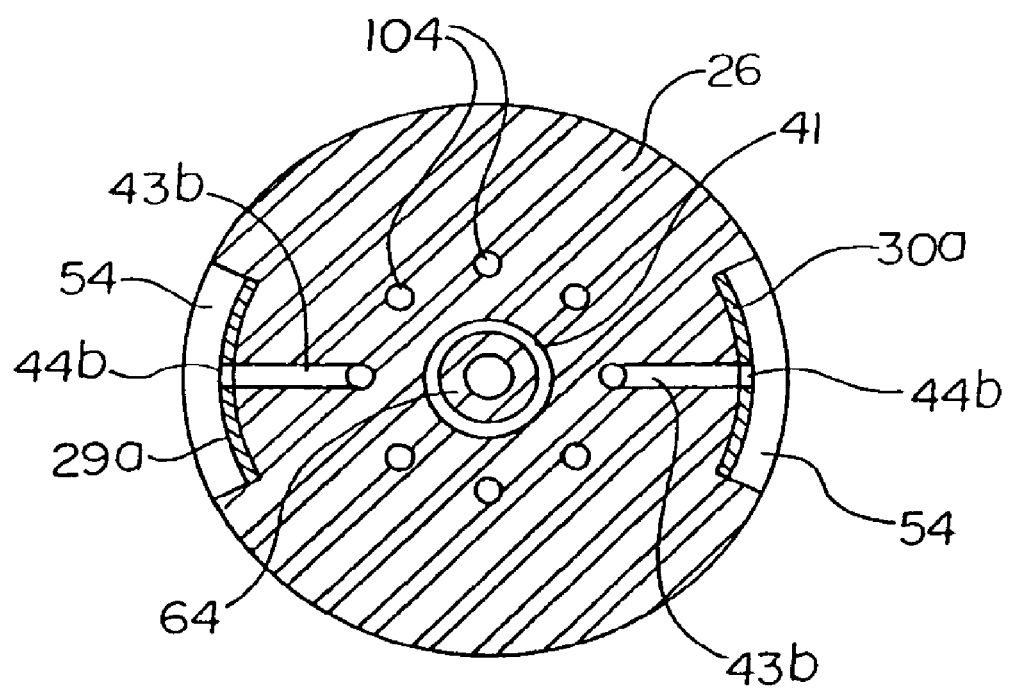
FIG. 60 is a schematic close-up cross-sectional view of the electrosurgical device of FIG. 57 taken in accordance with line 60-60 of FIG. 59.

Another exemplary electrosurgical device of the present invention which may be used in conjunction with the system of the present invention is shown at reference character 5*r* in FIG. 57, and more particularly in FIGS. 57-60. As best shown in FIG. 59, device 5*r* is used in conjunction with instrument 64. As with certain other embodiments disclosed herein, instrument 64 is contained within the central flow passage 41 within probe body 26 and thereafter, with use, the instrument 64 is extended from the distal end 27 of the electrosurgical device 5*r* and probe body 26 when the instrument 64 is extended distally. Also as disclosed with other embodiments, the instrument 64 (shown as a hollow needle with an open, pointed tip) may be configured to penetrate tissue and enable injection therapy to tissue, such as the administration of a vasoconstrictor. sclerotic or topical anesthetic through the lumen of a needle.

As shown in FIG. 59, central flow passage 41 comprises a lumen of substantially uniform cross-sectional area and diameter along its length. In addition to the above use for instrument 64 for device 5*r*, it serves as an occlusion for occluding central flow passage 41 while a portion of instrument 64 is contained therein. Unlike previous embodiments, central flow passage 41 of device 5*r* preferably does not provide fluid 24 from lumen 23 of tube 19 to lateral flow passage 43*a*, 43*b*. Rather, fluid 24 from lumen 23 of tube 19 is provided to lateral flow passages 43*a*, 43*b* through at least one off-center longitudinally directed passage 104 parallel with the longitudinal axis 31 and central flow passage 41. As shown, preferably passage 104 comprises a plurality of passages 104 angularly uniformly distributed about the longitudinal axis 31 and central flow passage 41.

With use of device 5*r*, fluid 24 provided from lumen 23 of tube 19 enters longitudinal flow passage fluid entrance opening 105 after the fluid flow is substantially inhibited from entering and flowing through central flow passage 41 due to the presence of instrument 64.

In certain medical procedures, it may be necessary to irrigate a tissue treatment site with a large volume of fluid either before, during or after tissue treatment with the electrosurgical device 5*r*. When such irrigation is required, instrument 64 may be retracted proximally from central flow passage 41, thus leaving central flow passage unoccluded by instrument 64. Consequently, in seeking the path of least resistance, fluid 24 from lumen 23 now predominately flows through central flow passage 41 and may be used, for example, to clean a tissue treatment site.

Figure 61:
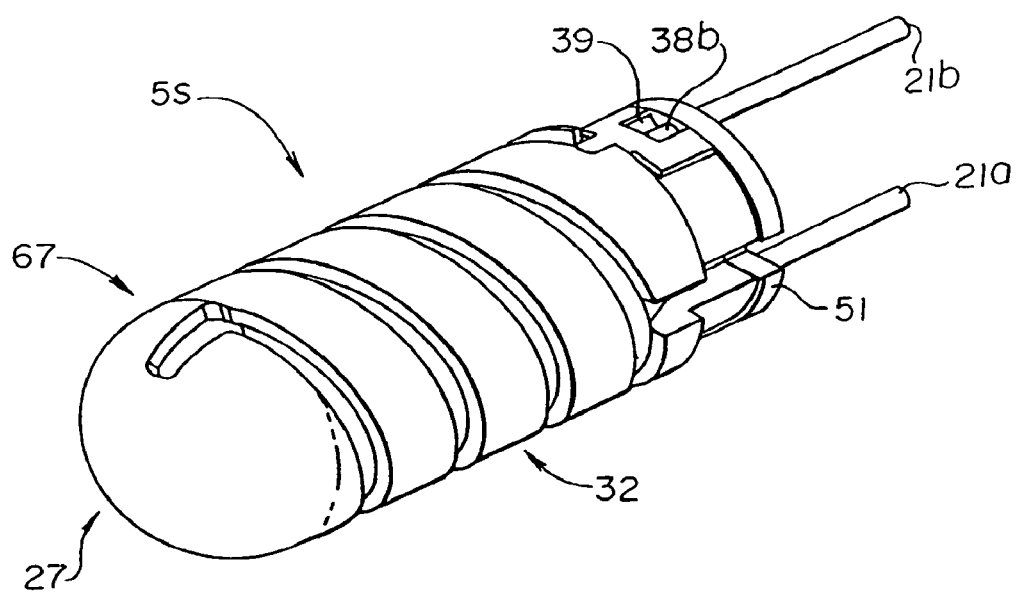
FIG. 61 is a schematic close-up front perspective view of an electrosurgical device according to another embodiment of the invention.
Figure 62:
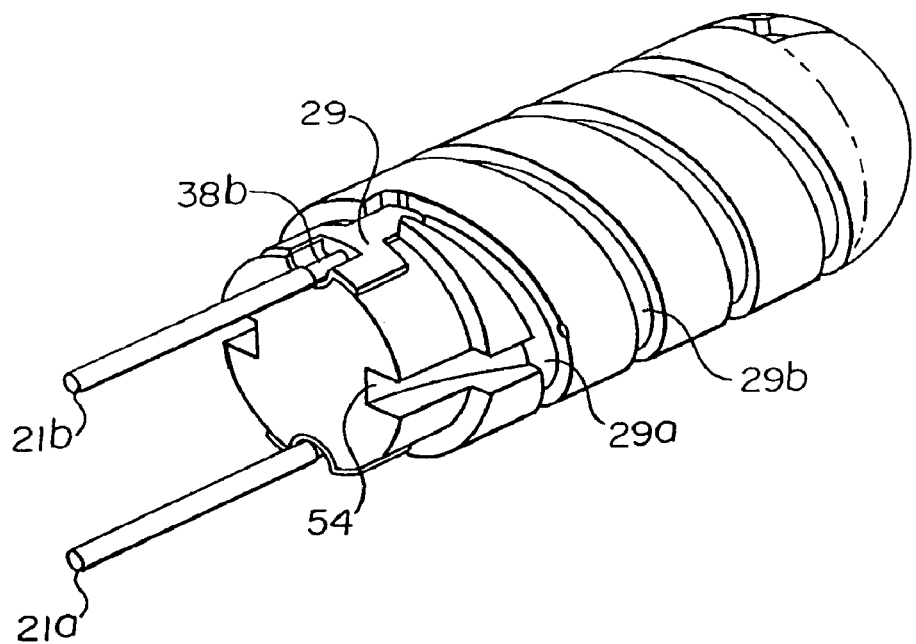
FIG. 62 is a schematic close-up rear perspective view of the electrosurgical device of FIG. 61 with member 51 removed.
Figure 63:
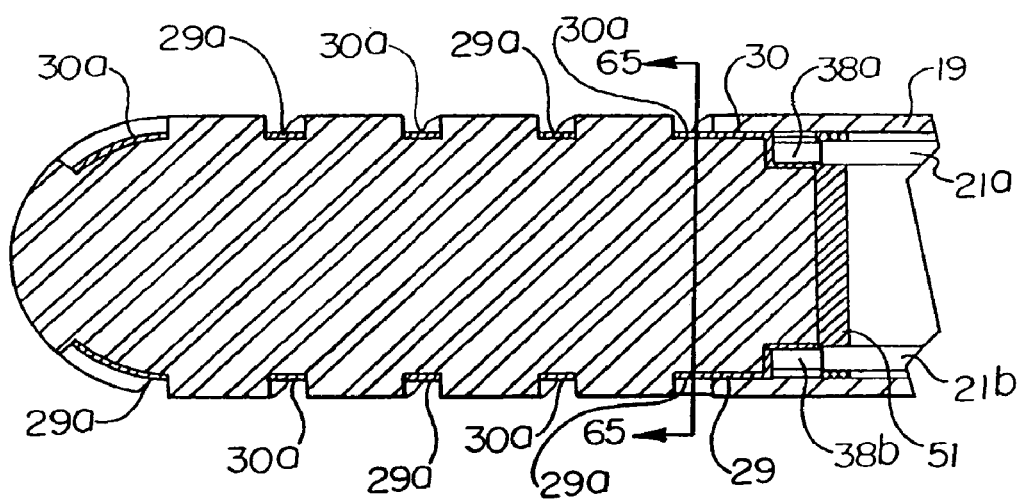
FIG. 63 is a schematic close-up cross-sectional view of the assembly of the electrosurgical device of FIG. 61 and tube 19 taken in accordance with line 12-12 of FIG. 13.
Figure 64:
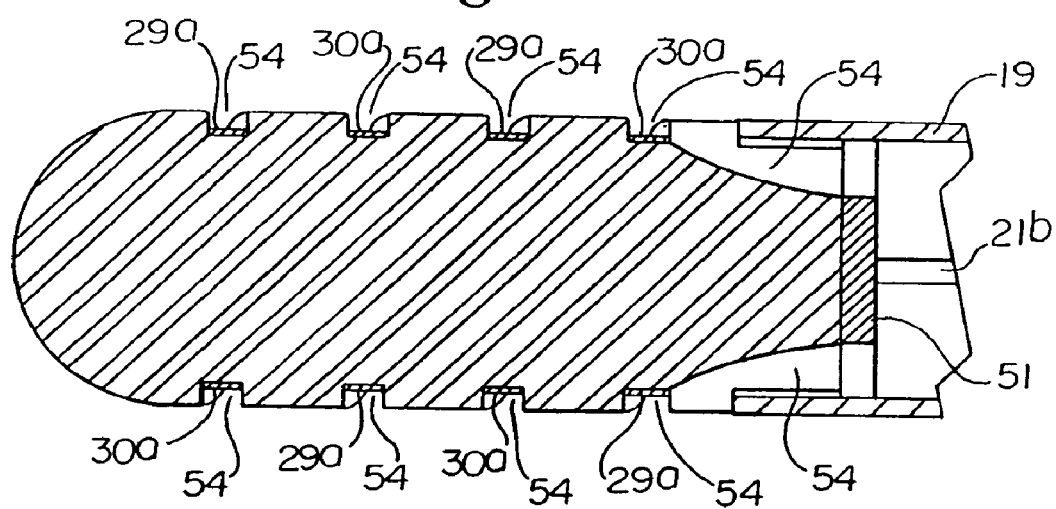
FIG. 64 is a schematic close-up cross-sectional view of the assembly of the electrosurgical device of FIG. 61 and tube 19 taken at 90 degrees to line 12-12 of FIG. 13.
Figure 65:
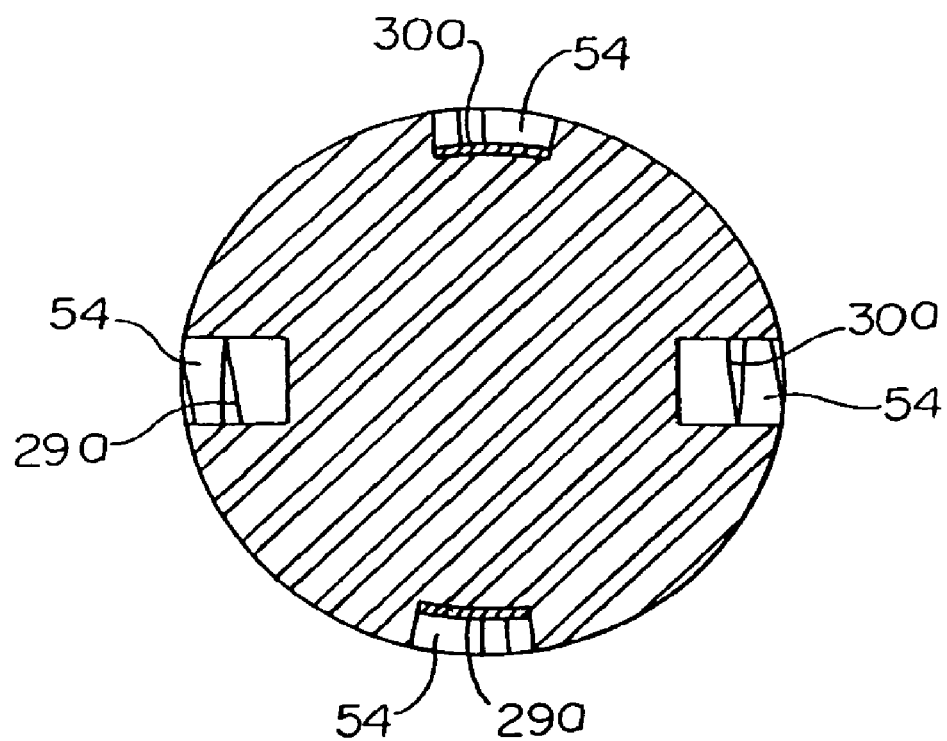
FIG. 65 is a schematic close-up cross-sectional view of the electrosurgical device of FIG. 61 taken in accordance with line 65-65 of FIG. 63.

Another exemplary electrosurgical device of the present invention which may be used in conjunction with the system of the present invention is shown at reference character 5*s* in FIG. 61, and more particularly in FIGS. 61-65. As shown in FIGS. 63-65, central flow passage 41 and lateral flow passages 43*a*, 43*b* have been eliminated. Thus, rather than fluid 24 from lumen 23 first flowing through central flow passage 41 and lateral flow passages 43*a*, 43*b* before reaching fluid flow channel 54, fluid 24 from lumen 23 of tube 19 flows directly into fluid flow channel 54. In other words, as shown in FIGS. 63-65, fluid flow channel 54 is in direct fluid communication with lumen 23 of tube 19.

As with other embodiments disclosed herein, fluid flow channels 54 and the electrodes 29a, 30a in recesses 53 are substantially coextensive. In other words, they substantially coincide or are equally extensive in location and boundaries on electrosurgical device 5s. As shown, in order to facilitate direct fluid communication of fluid flow channels 54 with lumen 23 of tube 19, preferably fluid flow channels 54 of device 5t are initiated within the confines of tube 19. In other words, within the lumen 23 of tube 19 proximal to distal end 18. As shown, for this embodiment, because the fluid flow channels are initiated within the confines of tube 19, preferably fluid flow channels 54 and electrodes 29a, 30a, are initiated at remote locations. In other words, do not overlie one another in the confines of tube 19. As shown, for a configuration of two electrodes and two flow channels, preferably the electrical connection for the electrodes and the initiation of the flow channels occurs approximately 90 degrees from one another on electrosurgical device 5s. In this manner, conductors 29/38b and 30/38a are configured to remain electrically insulated from one another (and inhibit a short circuit from there between in the presence of an electrically conductive fluid 24) by member 51 and the inner surface of the tube 19 which is preferably press fit against shoulder 34.

Preferably the relationship between the material for the probe body, electrodes and fluid throughout the various embodiments should be such that the fluid wets the surface of the probe body, plugs and/or electrodes to form a continuous thin coating thereon and does not form isolated rivulets or beads. Contact angle, θ, is a quantitative measure of the wetting of a solid by a liquid. It is defined geometrically as the angle formed by a liquid at the three phase boundary where a liquid, gas and solid intersect. In terms of the thermodynamics of the materials involved, contact angle θ involves the interfacial free energies between the three phases given by the equation $\gamma_{1v} \cos \theta = \gamma_{sv} - \gamma_{s1}$ where $\gamma_{1v}$, $\gamma_{sv}$ and $\gamma_{s1}$ refer to the interfacial energies of the liquid/vapor, solid/vapor and solid/liquid interfaces, respectively. If the contact angle θ is less than 90 degrees the liquid is said to wet the solid. If the contact angle is greater than 90 degrees the liquid is non-wetting. A zero contact angle represents complete wetting.

To effectively treat thick tissues, it can be advantageous to have the ability to pulse the RF power on and off. Under some circumstances, the temperature deep in tissue can rise quickly past the 100° C. desiccation point even though the electrode/tissue interface is boiling at 100° C. This manifests itself as "popping," as steam generated deep in the tissue boils too fast and erupts toward the surface. In one embodiment of the invention, a switch is provided on the control device or custom generator to allow the user to select a "pulse" mode of the RF power. Preferably, the RF power system in this embodiment is further controlled by software.

In some embodiments, it can be desirable to control the temperature of the conductive fluid before it is released from the electrosurgical device. In one embodiment, a heat exchanger is provided for the outgoing saline flow to either heat or chill the saline. The heat exchanger may be provided as part of the electrosurgical device or as part of another part of the system, such as within the enclosure 14. Pre-heating the saline to a predetermined level below boiling reduces the transient warm-up time of the device as RF is initially turned on, thereby reducing the time to cause coagulation of tissue. Alternatively, pre-chilling the saline is useful when the surgeon desires to protect certain tissues at the electrode/tissue interface and treat only deeper tissue. One exemplary application of this embodiment is the treatment of varicose veins, where it is desirable to avoid thermal damage to the surface of the skin. At the same time, treatment is provided to shrink underlying blood vessels using thermal coagulation. The temperature of the conductive fluid prior to release from the surgical device can therefore be controlled, to provide the desired treatment effect.

In another embodiment, the flow rate controller is modified to provide for a saline flow rate that results in greater than 100% boiling at the tissue treatment site. For example, the selection switch 12 of the flow rate controller 11 (shown in FIG. 1) can include settings that correspond to 110%, 120% and greater percentages of boiling. These higher settings can be of value to a surgeon in such situations as when encountering thick tissue, wherein the thickness of the tissue can increase conduction away from the electrode jaws. Since the basic control strategy neglects heat conduction, setting for 100% boiling can result in 80% of 90% boiling, depending upon the amount of conduction. Given the teachings herein, the switch of the flow rate controller can accommodate any desirable flow rate settings, to achieve the desired saline boiling at the tissue treatment site.

The invention can, in some embodiments, deliver fast treatment of tissue without using a temperature sensor built into the device or a custom special-purpose generator. In a preferred embodiment, there is no built-in temperature sensor or other type of tissue sensor, nor is there any custom generator. Preferably, the invention provides a means for controlling the flow rate to the device such that the device and flow rate controller can be used with a wide variety of general-purpose generators. Any general-purpose generator is useable in connection with the fluid delivery system and flow rate controller to provide the desired power; the flow rate controller will accept the power and constantly adjust the saline flow rate according to the control strategy. Preferably, the generator is not actively controlled by the invention, so that standard generators are useable according to the invention. Preferably, there is no active feedback from the device and the control of the saline flow rate is "open loop." Thus, in this embodiment, the control of saline flow rate is not dependent on feedback, but rather the measurement of the RF power going out to the device.

For purposes of the appended claims, the term "tissue" includes, but is not limited to, organs (e.g. liver, lung, spleen, gallbladder), highly vascular tissues (e.g. liver, spleen), soft and hard tissues (e.g. adipose, areolar, bone, bronchus-associated lymphoid, cancellous, chondroid, chordal, chromaffin, cicatricial, connective, elastic, embryonic, endothelial, epithelial, erectile, fatty, fibrous, gelatiginous, glandular, granulation, homologous, indifferent, interstitial, lymphadenoid, lymphoid, mesenchymal, mucosa-associated lymphoid, mucous, muscular, myeloid, nerve, osseous, reticular, scar, sclerous, skeletal, splenic, subcutaneous), tissue masses (e.g. tumors), etc.

While a preferred embodiment of the present invention has been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents. Furthermore, it should be understood that the appended claims do not necessarily comprise the broadest scope of the invention which the Applicant is entitled to claim, or the only manner(s) in which the invention may be claimed, or that all recited features are necessary.

All publications and patent documents cited in this application are incorporated by reference in their entirety for all purposes.

I claim:

1. A medical device comprising:
a catheter tube having a distal end and a lumen, the tube configured to assist in applying tamponage to a bleeding source in a gastrointestinal tract when flexed;
a catheter tip assembled with the tube adjacent the distal end of the tube, the catheter tip having a catheter tip outer surface and including:
a probe body comprising an electrically insulative material;
at least one electrode pair, the electrode pair comprising a first electrode spaced from a second electrode, the first electrode and the second electrode located on the probe body;
a fluid distribution manifold to direct a fluid from inside the probe body towards the tip outer surface, the manifold comprises a central passage within the probe body and a plurality of lateral passages which extend from the central passage towards the tip outer surface, the central passage narrowed at a distal end thereof; and
an injection needle housed within the central passage, the needle extendable from the central passage to provide treatment to tissue.

2. The medical device of claim 1 wherein a portion of the catheter tip is configured to be penetrated by a portion of the needle.

3. The medical device of claim 1 wherein a portion of the catheter tip is configured to open around a portion of the needle.

4. The medical device of claim 1 wherein a portion of the catheter tip is configured to least partially seal with a portion of the needle.

5. The medical device of claim 1 wherein a portion of the catheter tip is configured to electrically insulate the needle from the electrodes.

6. The medical device of claim 1 wherein a portion of the catheter tip provides a guide portion for guiding the needle from the lumen of the catheter tube to the central passage within the probe body.

7. The medical device of claim 1 wherein:
the central passage extends to a central passage outlet opening; and
a portion of the needle occludes at least a portion of the central passage outlet opening.

8. The medical device of claim 1 further comprising:
a first electrical connection to the catheter tip;
a second electrical connection to the catheter tip; and
a member comprising an electrically insulative portion, the electrically insulative portion electrically insulating the first electrical connection from the second electrical connection to inhibit a short circuit from forming between the two connections in the presence of an electrically conductive fluid.

9. The medical device of claim 1 wherein:
each electrode extends longitudinally along the probe body; and
the plurality of lateral passages are spaced longitudinally along the probe body.

10. The medical device of claim 9 wherein:
at least a portion of the plurality of lateral passages extend to an outlet opening located on the tip outer surface; and
the tip outer surface comprises an outer surface of at least one of the first and second electrodes.

11. The medical device of claim 1 wherein:
each electrode extends spirally around the probe body; and
the plurality of lateral passages are spaced spirally around the probe body.

12. The medical device of claim 11 wherein:
at least a portion of the plurality of lateral passages extend to an outlet opening located on the tip outer surface; and
the tip outer surface comprises an outer surface of at least one of the first and second electrodes.

13. The medical device of claim 1 wherein:
each electrode extends circularly around the probe body; and
the plurality of lateral passages are spaced circularly around the probe body.

14. The medical device of claim 13 wherein:
at least a portion of the plurality of lateral passages extend to an outlet opening located on the tip outer surface; and
the tip outer surface comprises an outer surface of at least one of the first and second electrodes.

15. The medical device of claim 1 wherein:
each electrode extends circumferentially around the probe body; and
the plurality of lateral passages are spaced circumferentially around the probe body.

16. The medical device of claim 15 wherein:
at least a portion of the plurality of lateral passages extend to an outlet opening located on the tip outer surface; and
the tip outer surface comprises an outer surface of at least one of the first and second electrodes.

17. The medical device of claim 1 wherein:
each electrode extends both longitudinally and circumferentially around the probe body; and
the plurality of lateral passages are spaced both longitudinally and circumferentially around the probe body.

18. The medical device of claim 17 wherein:
at least a portion of the plurality of lateral passages extend to an outlet opening located on the tip outer surface; and
the tip outer surface comprises an outer surface of at least one of the first and second electrodes.

19. The medical device of claim 1 wherein the at least one electrode pair comprises two electrode pairs.

20. The medical device of claim 1 wherein the at least one electrode pair comprises three electrode pairs.

* * * * *